United States Patent
Keler et al.

(10) Patent No.: US 10,865,244 B2
(45) Date of Patent: Dec. 15, 2020

(54) NUCLEIC ACIDS ENCODING AGONISTIC ANTIBODIES THAT BIND CD40

(71) Applicant: Celldex Therapeutics, Inc., Needham, MA (US)

(72) Inventors: Tibor Keler, Pipersville, PA (US); Joel Goldstein, Hopewell, NJ (US); Laura A. Vitale, Doylestown, PA (US); Lizhen He, Allentown, PA (US); Tom O'Neill, Washington, NJ (US); Andrea Crocker, New Hope, PA (US); Karuna Sundarapandiyan, Kendall Park, NJ (US); Lawrence J. Thomas, Easton, MA (US); Jenifer Widger, Alpha, NJ (US)

(73) Assignee: Celldex Therapeutics, Inc., Hampton, NJ (US)

( * ) Notice: Subject to any disclaimer, the term of this patent is extended or adjusted under 35 U.S.C. 154(b) by 119 days.

(21) Appl. No.: 15/490,589

(22) Filed: Apr. 18, 2017

(65) Prior Publication Data

US 2018/0066053 A1 Mar. 8, 2018

Related U.S. Application Data

(60) Provisional application No. 62/324,170, filed on Apr. 18, 2016.

(51) Int. Cl.

| | |
|---|---|
| *C12N 15/13* | (2006.01) |
| *C07K 16/28* | (2006.01) |
| *A61K 39/395* | (2006.01) |
| *C07K 14/54* | (2006.01) |
| *C07K 14/715* | (2006.01) |
| *C07K 14/705* | (2006.01) |
| *A61K 39/00* | (2006.01) |

(52) U.S. Cl.
CPC .... *C07K 16/2803* (2013.01); *A61K 39/39541* (2013.01); *C07K 14/54* (2013.01); *C07K 14/715* (2013.01); *C07K 16/2878* (2013.01); *A61K 2039/505* (2013.01); *C07K 14/70575* (2013.01); *C07K 2317/34* (2013.01); *C07K 2317/73* (2013.01); *C07K 2317/74* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| 5,182,368 A | 1/1993 | Ledbetter et al. |
|---|---|---|
| 9,102,737 B2 | 8/2015 | Chen et al. |
| 9,527,916 B2 | 12/2016 | Van Eenennaam et al. |
| 9,683,046 B2 | 6/2017 | Chen et al. |
| 2004/0110226 A1* | 6/2004 | Lazar ..................... C07K 16/00 435/7.1 |
| 2014/0112942 A1 | 4/2014 | Van Eenennaam et al. |
| 2016/0185870 A1 | 6/2016 | Van Eenennaam et al. |
| 2016/0194402 A1 | 7/2016 | Van Eenennaam et al. |
| 2017/0320957 A1 | 11/2017 | Chen et al. |
| 2019/0322743 A1 | 10/2019 | Keler et al. |

FOREIGN PATENT DOCUMENTS

| EP | 318 216 A1 | 5/1989 |
|---|---|---|
| WO | 1990/011089 A1 | 10/1990 |
| WO | 1994/001547 A2 | 1/1994 |
| WO | 1995/009653 A1 | 4/1995 |
| WO | 1995/017202 A1 | 6/1995 |
| WO | 1996/026735 A1 | 9/1996 |
| WO | 00/75348 A1 | 12/2000 |
| WO | 02090986 A1 | 11/2002 |
| WO | 2005/044294 A2 | 5/2005 |
| WO | 2005/044304 A2 | 5/2005 |
| WO | 2005/044305 A2 | 5/2005 |
| WO | 2005/044306 A2 | 5/2005 |
| WO | 2005/044854 A2 | 5/2005 |
| WO | 2005/044855 A2 | 5/2005 |
| WO | 2005044307 A2 | 5/2005 |
| WO | 2006/068953 A2 | 6/2006 |
| WO | 2008/054603 A2 | 5/2008 |
| WO | 2008/055206 A2 | 5/2008 |
| WO | 2009/026303 A1 | 2/2009 |
| WO | 2010/007533 A2 | 1/2010 |
| WO | 2010/032061 A1 | 3/2010 |
| WO | 2010/107752 A2 | 9/2010 |
| WO | 2010/108153 A2 | 9/2010 |
| WO | 2010/108154 A2 | 9/2010 |
| WO | 2012/096994 A2 | 7/2012 |
| WO | 2013/130981 A1 | 9/2013 |
| WO | 2013/166236 A1 | 11/2013 |
| WO | 2014/070934 A1 | 5/2014 |

(Continued)

OTHER PUBLICATIONS

Rudikoff et al, Proc Natl Acad Sci USA 79: 1979-1983 (1982). (Year: 1982).*
Colman, Research in Immunology 145: 33-36 (1994). (Year: 1994).*
Kussie et al., J. Immunol. 152: 146-152 (1994). (Year: 1994).*
Chen et al., EMBO J., 14: 2784-2794 (1995). (Year: 1995).*
D'Angelo et al. Many Routes to an Antibody Heavy-Chain CDR3: Necessary, Yet Insufficient, for Specific Binding (Frontiers in Immunology vol. 9, Article 395 Mar. 2018; doi: 10.3389/fimmu.2018. 00395), (Year: 2018).*

(Continued)

*Primary Examiner* — Phillip Gambel
(74) *Attorney, Agent, or Firm* — Nelson Mullins Riley & Scarborough LLP; Jane E. Remillard, Esq.; Jeanne M. DiGiorgio, Esq.

(57) ABSTRACT

Isolated monoclonal agonistic antibodies which bind to human CD40 and related antibody-based compositions and molecules are disclosed. Also disclosed are therapeutic and diagnostic methods for using the antibodies.

11 Claims, 40 Drawing Sheets

Specification includes a Sequence Listing.

(56) References Cited

FOREIGN PATENT DOCUMENTS

| WO | 2014/159010 A1 | 10/2014 |
|---|---|---|
| WO | 2014/159595 A2 | 10/2014 |
| WO | 2014/164959 A2 | 10/2014 |
| WO | 2017/079112 A1 | 5/2017 |
| WO | 2017/184619 A2 | 10/2017 |

OTHER PUBLICATIONS

Piche-Nicholas et al., Changes in complemetarity-determining regions significantly alter IgG binding to the neonatal Fc receptor (FcRN) and pharmacokinetics, MABS 2018, vol. 10, No. 1, 81-94, doi.org/10.1080/19420862.2017.1389355. (Year: 2018).*

International Preliminary Report on Patentability, PCT/US2017/028162, dated Oct. 23, 2018, 10 pages.

Bennett et al., "Help for cytotoxic-T-cell responses is mediated by CD40 signalling," Nature, vol. 393(6684):478-80(1998).

Braesch-Andersen et al., "Biochemical characteristics and partial amino acid sequence of the receptor-like human B Cell and carcinoma antigen CDw40," J Immunol., vol. 142(2):562-567 (1989).

Fransen et al., "Effectiveness of slow-release systems in CD40 agonistic antibody immunotherapy of cancer," Vaccine, vol. 32:1654-1660 (2014).

Khalil et al., "Anti-CD40 agonist antibodies: preclinical and clinical experience," Update Cancer Ther, vol. 2(2): 61-65 (2007).

Ranheim EA, et al., "Expression of CD27 and its ligand, CD70, on chronic lymphocytic leukemia B cells," Blood, vol. 85(12):3556-65 (1995).

Sandin et al., "Locally delivered CD40 agonist antibody accumulates in secondary lymphoid organs and eradicates experimental disseminated bladder cancer," Cancer Immunol Res, 2:80-90 (2014).

Tai et al., "Mechanisms by which SGN-40, a humanized anti-CD40 antibody, induces cytotoxicity in human multiple myeloma cells: clinical implications," Cancer Res, vol. 20 64(8):2846-2852 (2004).

Dronca, S. et al., "Immunomodulatory Antibody Therapy of Cancer: The Closer, the Better," Clinical Cancer Research, vol. 21 (5):944-946 (2014).

Invitation to Pay Additional Fees, and Where Applicable, Protest Fee, PCT/US2017/028162, dated Aug. 30, 2017, 17 pages.

Mangsbo, S. et al., "ADC-1013, an agonistic CD40 antibody optimized for local immunotherapy of cancer," Journal for Immunotherapy, vol. 1 (No. Suppl 1) p. P42 (2013).

Sandin, L.C. et al., "Locally Delivered CD40 Agonist Antibody Accumulates in Secondary Lymphoid Organs and Eradicates Experimental Disseminated Bladder Cancer," Cancer Immunology Research, vol. 2 (1):80-90(2014).

Vonderheide, R.H. et al., "Agonistic CD40 Antibodies and Cancer Therapy," Clinical Cancer Research, vol. 19 (5):1035-1043 (2013).

International Search Report and Written Opinion, PCT/US2017/028162, dated Nov. 23, 2017, 21 pages.

* cited by examiner

| Clone | KD (pM) | kon(1/Ms) | kdis(1/s) |
|---|---|---|---|
| 3C3 | 10.7 | 8.13E+05 | 8.67E-06 |
| 3G5 | 3.3 | 9.05E+05 | 2.97E-06 |
| 1B4 | 10.5 | 8.32E+05 | 8.76E-06 |
| 3B6 | 7.9 | 7.82E+05 | 6.14E-06 |
| 6H6 | 2.8 | 9.05E+05 | 2.49E-06 |

FIG. 1

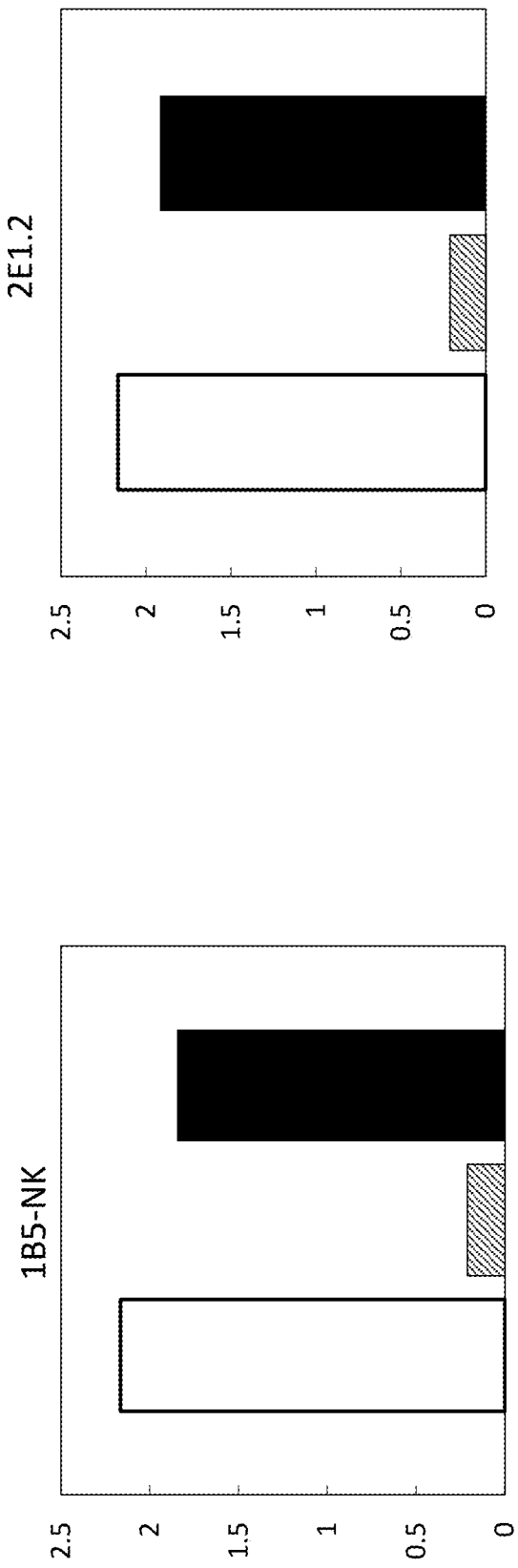

FIG. 7B
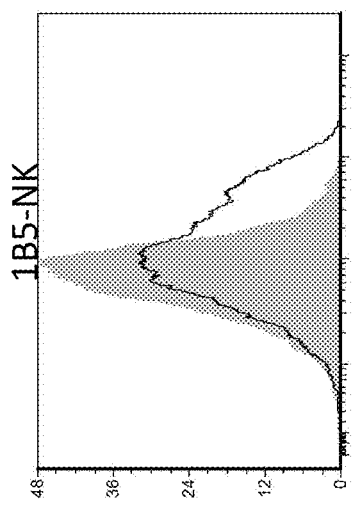
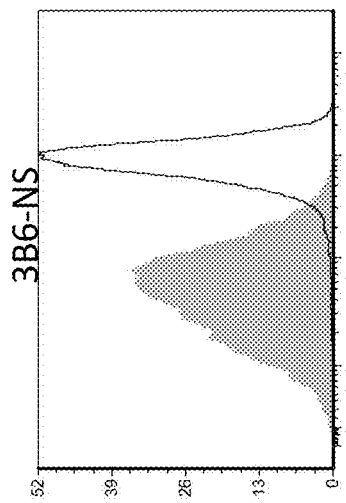
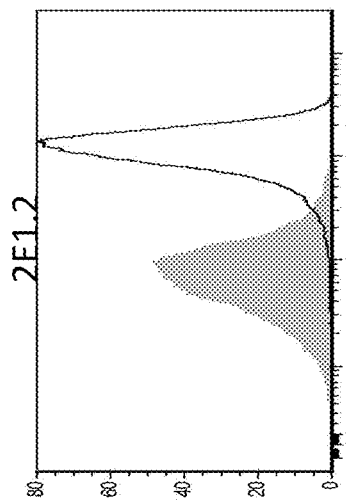

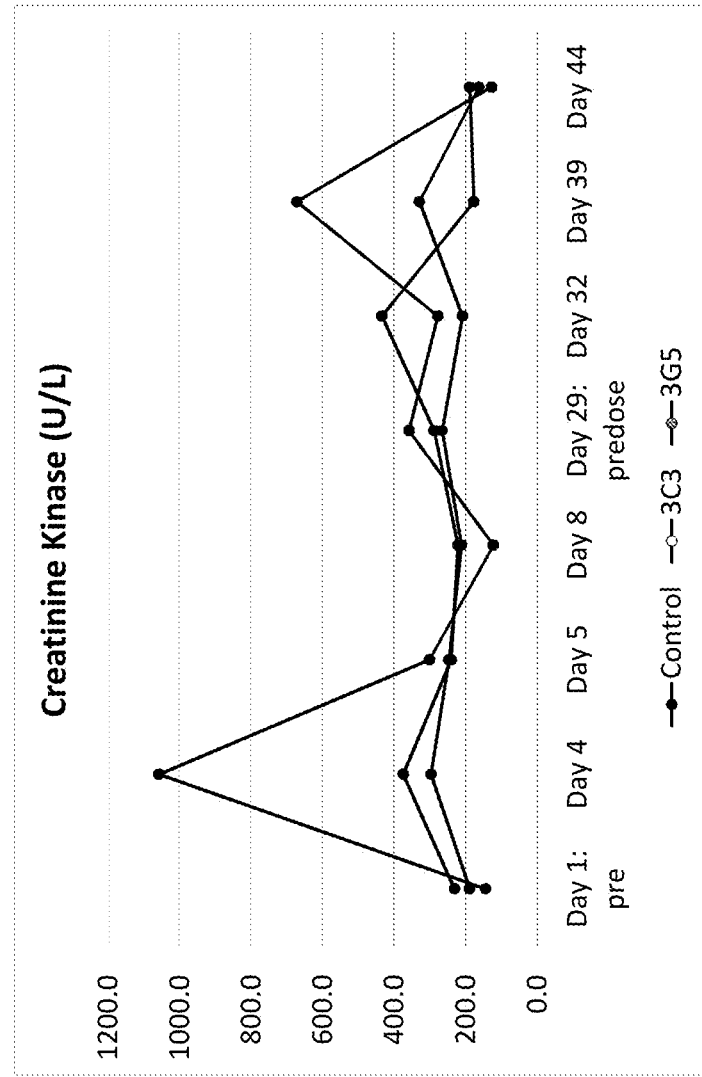

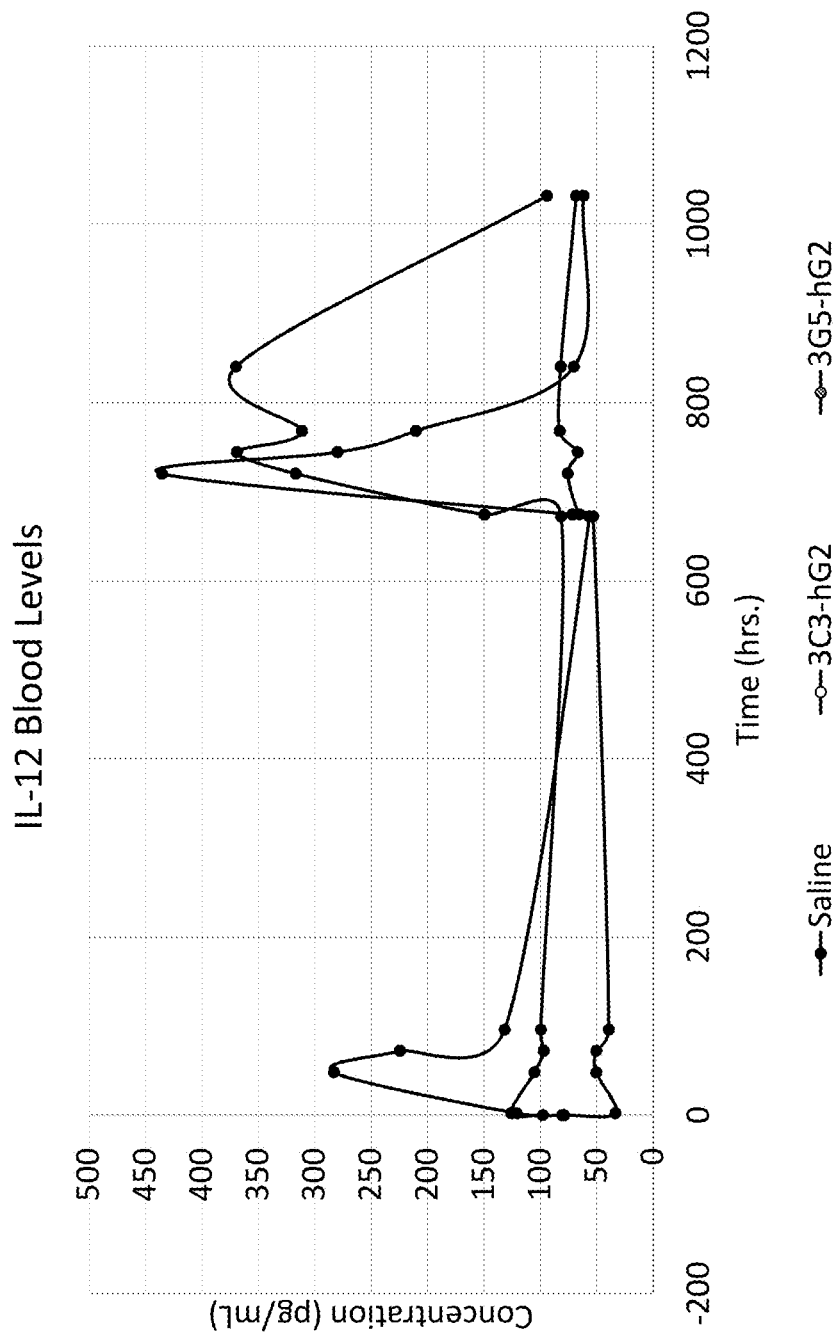

Cytokine response in whole blood assay

| | Donor 1 | Donor 2 | Donor 3 | Donor 4 | Donor 5 |
|---|---|---|---|---|---|
| IL-1β | | | | | |
| huIgG2 control | 0.2 | 1.4 | 1.6 | 13 | 4.5 |
| LPS | 682 | 697 | 885 | 882 | 858 |
| 3C3 | 0.1 | 1.3 | 1 | 11.3 | 5.6 |
| IL-6 | | | | | |
| huIgG2 control | 2.1 | 1 | 12.3 | 1.3 | 2.9 |
| LPS | 12.5 | 12.6 | 11.6 | 11.7 | 16 |
| 3C3 | 1.9 | 0.9 | 11 | 1.2 | 2.5 |
| TNFα | | | | | |
| huIgG2 control | 0.6 | 0.7 | 1.4 | 1 | 1.3 |
| LPS | 45.2 | 43.9 | 48.7 | 45.6 | 27.5 |
| 3C3 | 0.7 | 1.2 | 1.5 | 1.1 | 1.6 |
| IFNγ | | | | | |
| huIgG2 control | BD | BD | BD | BD | 0.5 |
| LPS | BD | BD | BD | 49.8 | BD |
| 3C3 | BD | BD | BD | BD | 1.3 |

FIG. 31

NUCLEIC ACIDS ENCODING AGONISTIC ANTIBODIES THAT BIND CD40

RELATED APPLICATION

This application claims priority to U.S. Provisional Application No. 62/324,170, filed Apr. 18, 2016. The contents of the aforementioned application is hereby incorporated by reference.

SEQUENCE LISTING

The instant application contains a Sequence Listing which has been submitted electronically in ASCII format and is hereby incorporated by reference in its entirety. Said ASCII copy, created on Nov. 6, 2017, is named Sequence-Listing_CDJ-393.txt and is 75,696 bytes in size.

BACKGROUND OF THE INVENTION

Interactions between T cells and antigen-presenting cells involve a variety of accessory molecules that facilitate the generation of an immune response. One such molecule is CD40, a member of the tumor necrosis factor receptor (TNF-R) superfamily which binds to CD40L (Ranheim E A, et al., *Blood.* 1995 Jun. 15; 85(12):3556-65). CD40 is a transmembrane 43-48 kDa glycoprotein composed of 277 amino acid residues (Braesch-Andersen et al., 1989). CD40 is expressed by antigen-presenting cells (APC) and engagement of its natural ligand (CD40L) on T cells activates APC including dendritic cells and B cells (Khalil and Vonderhide (2007) *Update Cancer Ther,* 2(2): 61-65), thus enhancing immune responses. CD40 is also expressed on many tumor cells and its ligation in this setting mediates a direct cytotoxic effect, e.g., engagement of CD40 on tumor cells results in apoptosis in vitro and impaired tumor growth in vivo (Tai et al. (2004) *Cancer Res,* 64(8):2846-52).

Monoclonal antibodies against CD40 provide a variety of potential therapeutic purposes including the treatment of cancers. For example, agonistic CD40 antibodies have been shown to substitute for T cell help provided by CD4+ lymphocytes in murine models of T cell-mediated immunity, and in tumor-bearing hosts CD40 agonists trigger effective immune responses against tumor-associated antigens (Bennett et al. (1998) *Nature,* 393(6684):478-80). In addition, CD40 antibodies hold great promise for use in vaccines (Fransen et al. (2014) *Vaccine* 32:1654-1660). However, there are potential adverse effects associated with agents that strongly modulate the immune system (Sandin et al. (2014) *Cancer Immunol Res,* 2:80-90). Accordingly, there is a need for further insight into the specific properties and mechanisms that make CD40 antibodies therapeutically effective, as well as improved therapeutic antibodies against CD40 that can be used to treat and/or preventing diseases.

SUMMARY OF THE INVENTION

The present invention provides isolated anti-CD40 antibodies having particular functional properties which can be linked with advantageous and desirable therapeutic effects. Specifically, agonistic anti-CD40 monoclonal antibodies capable of increasing an immune response to an antigen (e.g., an antigen expressed on a cell) have been generated and characterized. As used herein, the term "antibody" refers to full-length antibodies and antigen binding portions thereof.

In one embodiment, the anti-CD40 antibodies enhance immune responses against an antigen, e.g., by enhancing T cell-mediated immune responses, B-cell activation, and/or cytokine production. The antibodies can be administered alone or in combination therapies (e.g., with vaccine therapy and/or chemotherapy).

In another embodiment, the anti-CD40 antibodies are capable of increasing an immune response to an antigen without inducing antibody-dependent cellular cytotoxicity (ADCC) of CD40 expressing cells and/or complement dependent cellular cytotoxicity (CDC) of CD40 expressing cells.

In another embodiment, the antibodies comprise an effectorless constant region. In one embodiment, the constant region is an IgG2 isotype (e.g., human IgG2).

In yet another embodiment, the anti-CD40 antibodies exhibit one or more of the following properties:

(a) no blocking of binding of CD40L to human CD40, independent of Fc receptor binding;

(b) blocking of binding of CD40L to human CD40, independent of Fc receptor binding;

(c) activation of human CD40 expressed on an Antigen Presenting Cell (APC), independent of Fc receptor binding;

(d) induction of apoptisis of a tunore cell;

(e) T-cell stimulatory activity;

(f) enhanced B-cell activation; and/or (g) capable of synergising with CD40L.

Preferably the antibodies act independently of Fc receptor interaction. Preferably the antibodies are IgG2 isotype antibodies.

In one embodiment, the agonistic antibodies are capable of increasing an immune response independent of Fc receptor binding. For example, the antibodies may exhibit potent agonistic features without cross-linking with an Fc receptor, such as FcγR. These agonistic features include, e.g., an increase in T-cell activity and/or an increase in B cell activation as measured, e.g., by an increase in the expression of cell surface markers selected from the group consisting of HLA-DR V450, CD54 PE, CD86 APC, CD83 BV510, CD19 V500, CD54 PE, HLA-DR V450, CD23 PerCP-Cy5.5, CD69 APC, CD86 APC, CD38 and CD71 PE.

In another embodiment, the antibodies block binding of CD40 to CD40L (CD154) on CD40-expressing cells. In particular embodiments, the antibodies inhibit the binding of soluble CD40L to CD40 expressing cells by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. In a particular embodiment, the anti-CD40 antibody inhibits binding of CD40L by at least about 70% as measured, e.g., by FACS, bio-layer interferometry (BLI) or Biacore. In another embodiment, the anti-CD40 antibody inhibits binding of CD40L by at least about 80% as measured by e.g., by FACS, BLI or Biacore.

In another embodiment, the antibodies induce apoptosis of cells, as measured, e.g., by increased expression of CD95. The antibodies also can be constructed to include an Fc region which has specificity for a particular Fc receptor (e.g., FcγRI (CD64), FcγRIIA (CD32), FcγRIIB1 (CD32), FcγRIIB2 (CD32), FcγRIIIA (CD16a), FcγRIIIB (CD16b), FcεRI, FcεRII (CD23), FcαRI (CD89), Fcα/μR, and FcRn).

In another embodiment, the antibodies are capable of binding to human CD40 with an equilibrium dissociation constant Kd of $10^{-10}$ M or less, preferably $10^{-11}$ M or less and/or cross-reacting with cynomolgus CD40.

Particular anti-CD40 antibodies of the invention include antibodies 3C3, 3G5, 1B4, 3B6, 6H6, 2E1.2, 1B5-NK, 3B6-NS, and related embodiments described below.

In one embodiment, the antibodies comprise a heavy chain variable region CDR3 sequence selected from the group consisting of SEQ ID NOs: 9, 10, 23, 24, 37, 38, 51, 52, 65, 66, 65, 66, 79, 80, 93, 94, 107, 108, including conservative sequence modifications thereof (e.g., conservative amino acid substitutions). The antibodies may further comprise light chain variable region CDR3 sequence selected from the group consisting of SEQ ID NOs: 15, 16, 29, 30, 43, 44, 57, 58, 71, 72, 85, 86, 99, 100, 113, 114, including conservative sequence modifications thereof. In another embodiment, the heavy chain CDR2 and/or CDR1 sequences are selected from SEQ ID NOs: 7, 8, 21, 22, 35, 36, 49, 50, 63, 64, 77, 78, 91, 92, 105, 106, and SEQ ID NOs: 5, 6, 19, 20, 33, 34, 47, 48, 61, 62, 61, 62, 75, 76, 89, 90, 103, 104, respectively, including conservative sequence modifications thereof. In another embodiment, the light chain CDR2 and/or CDR1 sequences are selected from SEQ ID NOs: 13, 14, 27, 28, 41, 42, 55, 56, 69, 70, 84, 85, 97, 98, 111, 112, and SEQ ID NOs: 11, 12, 25, 26, 40, 41, 53, 54, 67, 68, 81, 82, 95, 96, 109, 110, respectively, including conservative sequence modifications thereof.

In another embodiment, the antibodies comprise a heavy chain variable region having an amino acid sequence selected from the group consisting of SEQ ID NOs: 3, 17, 31, 45, 59, 73, 87, 101, including conservative sequence modifications thereof. The antibodies may further comprise a light chain variable region having an amino acid sequence selected from the group consisting of SEQ ID NOs: 4, 18, 32, 46, 60, 74, 88, 102, including conservative sequence modifications thereof.

In another embodiment, antibodies comprise heavy and/or light chain variable regions respectively having the following amino acid sequences (including conservative sequence modifications):
(a) SEQ ID NOs: 3 and/or 4;
(b) SEQ ID NOs: 17 and/or 18;
(c) SEQ ID NOs: 31 and/or 32;
(d) SEQ ID NOs: 45 and/or 46;
(e) SEQ ID NOs: 59 and/or 60;
(f) SEQ ID NO: 73 and/or 74;
(g) SEQ ID NO: 87 and/or 88; or
(h) SEQ ID NO: 101 and/or 102.

Antibodies which include heavy and light chain variable regions having at least 80%, or at least 85%, or at least 90%, or at least 95%, or at least 96%, or at least 97%, or at least 98%, or at least 99%, or greater sequence identity to any of the above sequences also are included in the present invention. Ranges intermediate to the above-recited values, e.g., heavy and light chain variable regions having at least 80-85%, 85-90%, 90-95% or 95-100% sequence identity to any of the above sequences also are encompassed by the present invention.

In yet another embodiment, the antibodies bind to human CD40 and have the CDR sequences from the heavy and light chain variable regions respectively having the amino acid sequences as set forth in:
(a) SEQ ID NOs: 3 and 4;
(b) SEQ ID NOs: 17 and 18;
(c) SEQ ID NOs: 31 and 32;
(d) SEQ ID NOs: 45 and 46;
(e) SEQ ID NOs: 59 and 60; or
(f) SEQ ID NO: 73 and 74;
(g) SEQ ID NO: 87 and 88; or
(h) SEQ ID NO: 101 and 102
(in each case including one conservative sequence modification, two conservative sequence modifications, or up to three, up to four, or up to five conservative sequence modifications within one or more CDRs).

In another embodiment, the antibodies binds to human CD40 and have:
(a) heavy chain CDR1, CDR2, and CDR3 sequences comprising SEQ ID NOs: 5, 7, 9, respectively, and/or light chain CDR1, CDR2, and CDR3 sequences comprising SEQ ID NOs: 11, 13, 15, respectively;
(b) heavy chain CDR1, CDR2, and CDR3 sequences comprising SEQ ID NOs: 19, 21, 23, respectively, and/or light chain CDR1, CDR2, and CDR3 sequences comprising SEQ ID NOs: 25, 27, 29, respectively, respectively;
(c) heavy chain CDR1, CDR2, and CDR3 sequences comprising SEQ ID NOs: 33, 35, 37, respectively, and/or light chain CDR1, CDR2, and CDR3 sequences comprising SEQ ID NOs: 39, 41, 43, respectively;
(d) heavy chain CDR1, CDR2, and CDR3 sequences comprising SEQ ID NOs: 47, 49, 51, respectively, and/or light chain CDR1, CDR2, and CDR3 sequences comprising SEQ ID NOs: 53, 55, 57, respectively;
(e) heavy chain CDR1, CDR2, and CDR3 sequences comprising SEQ ID NOs: 61, 63, 65, respectively and/or light chain CDR1, CDR2, and CDR3 sequences comprising SEQ ID NOs: 67, 69, 71, respectively;
(f) heavy chain CDR1, CDR2, and CDR3 sequences comprising SEQ ID NOs: 75, 77, 79, respectively and/or light chain CDR1, CDR2, and CDR3 sequences comprising SEQ ID NOs: 81, 83, 85, respectively;
(g) heavy chain CDR1, CDR2, and CDR3 sequences comprising SEQ ID NOs: 89, 91, 93, respectively and/or light chain CDR1, CDR2, and CDR3 sequences comprising SEQ ID NOs: 95, 97, 99, respectively; or
(h) heavy chain CDR1, CDR2, and CDR3 sequences comprising SEQ ID NOs: 103, 105, 107, respectively and/or light chain CDR1, CDR2, and CDR3 sequences comprising SEQ ID NOs: 109, 111, 113, respectively, (in each case optionally including one conservative sequence modification, two conservative sequence modifications, or up to three, up to four, or up to five conservative sequence modifications within one or more of said CDRs).

In yet another embodiment, the antibodies binds to human CD40 and have:
(a) heavy chain CDR1, CDR2, and CDR3 sequences comprising SEQ ID NOs: 6, 8, 10, respectively, and/or light chain CDR1, CDR2, and CDR3 sequences comprising SEQ ID NOs: 12, 14, 16, respectively;
(b) heavy chain CDR1, CDR2, and CDR3 sequences comprising SEQ ID NOs: 20, 22, 24, respectively, and/or light chain CDR1, CDR2, and CDR3 sequences comprising SEQ ID NOs: 26, 28, 30, respectively, respectively;
(c) heavy chain CDR1, CDR2, and CDR3 sequences comprising SEQ ID NOs: 34, 36, 38, respectively, and/or light chain CDR1, CDR2, and CDR3 sequences comprising SEQ ID NOs: 40, 42, 44, respectively;
(d) heavy chain CDR1, CDR2, and CDR3 sequences comprising SEQ ID NOs: 48, 50, 52, respectively, and/or light chain CDR1, CDR2, and CDR3 sequences comprising SEQ ID NOs: 54, 56, 58, respectively;
(e) heavy chain CDR1, CDR2, and CDR3 sequences comprising SEQ ID NOs: 62, 64, 66, respectively and/or light chain CDR1, CDR2, and CDR3 sequences comprising SEQ ID NOs: 68, 70, 72, respectively; or
(f) heavy chain CDR1, CDR2, and CDR3 sequences comprising SEQ ID NOs: 76, 78, 80, respectively and/or light chain CDR1, CDR2, and CDR3 sequences comprising SEQ ID NOs: 82, 84, 86, respectively;

(g) heavy chain CDR1, CDR2, and CDR3 sequences comprising SEQ ID NOs: 90, 92, 94, respectively and/or light chain CDR1, CDR2, and CDR3 sequences comprising SEQ ID NOs: 96, 98, 100, respectively; or (h) heavy chain CDR1, CDR2, and CDR3 sequences comprising SEQ ID NOs: 104, 106, 108, respectively and/or light chain CDR1, CDR2, and CDR3 sequences comprising SEQ ID NOs: 110, 112, 114, respectively, (in each case optionally including one conservative sequence modification, two conservative sequence modifications, or up to three, up to four, or up to five conservative sequence modifications within one or more of said CDRs).

In another aspect, the invention provides antibodies which compete for binding to CD40 with the particular antibodies described above. In one embodiment, the antibody competes for binding to CD40 with an antibody comprising heavy and/or light chain variable regions comprising the amino acid sequences set forth in SEQ ID NOs: 3 and 4, SEQ ID NOs: 17 and 18, SEQ ID NOs: 31 and 32, SEQ ID NOs: 45 and 46, SEQ ID NOs: 59 and 60, SEQ ID NOs: 73 and 74, SEQ ID NO: 87 and 88, SEQ ID NO: 101 and 102, respectively.

In another aspect, the invention provides antibodies that bind to the same epitope as, or an epitope on CD40 recognized by, the particular antibodies described above. In one embodiment, the antibody binds to an epitope on CD40 recognized by an antibody comprising heavy and/or light chain variable regions comprising the amino acid sequences set forth in SEQ ID NOs: 3 and 4, SEQ ID NOs: 17 and 18, SEQ ID NOs: 31 and 32, SEQ ID NOs: 45 and 46, SEQ ID NOs: 59 and 60, SEQ ID NOs: 73 and 74, SEQ ID NO: 87 and 88, SEQ ID NO: 101 and 102, respectively. In some embodiments, the antibody binds to the same epitope as antibody 3C3 or 3G5.

In another aspect, the invention provides antibodies that bind to one or more residues within amino acid residues 1-5 and 33-36 of the extracellular domain (ECD) of human CD40 (SEQ ID NO: 133). In some embodiments, the antibodies further bind to one or more amino acid selected from the group consisting of amino acids 25, 26, 28 and 30 of the ECD of human CD40 (SEQ ID NO: 133). In some embodiments, the antibodies bind to one or more amino acids selected from the group consisting of amino acids 5, 33, 34 and 36 of the ECD of human CD40 (SEQ ID NO: 133). In some embodiments, the antibodies bind to amino acids 5, 33 and 36 of the ECD of human CD40 (SEQ ID NO: 133). In some embodiments, the antibodies bind to amino acids 5, 33, 34 and 36 of the ECD of human CD40 (SEQ ID NO: 133).

In any of the foregoing aspects, the invention provides antibodies wherein substitution of alanine with threonine at position 5 of the ECD of human CD40 (SEQ ID NO: 133) reduce binding of the antibodies by at least 30% relative to bind to the ECD of human CD40 (SEQ ID NO: 133). In some embodiments, substitution of alanine with threonine at position 5 of the ECD of human CD40 reduces binding of the antibodies by at least 50% relative to binding to the ECD of human CD40 (SEQ ID NO: 133). In some embodiments, substitution of alanine with threonine at position 5 of the ECD of human CD40 reduces binding of the antibodies by at least 80% relative to binding to the ECD of human CD40 (SEQ ID NO: 133).

In any of the foregoing aspects, the invention provides antibodies that exhibit a synergistic effect with CD40L which may be endogenous CD40L. In some embodiments, the synergistic effect is increased induction of CD95 expression when incubated with Ramos cells. In some embodiments, the synergistic effect is an increase in B cell proliferation when incubated with human B cells. In some embodiments, the synergistic effect is increased induction of IL12p40 expression when incubated with dendritic cells. In some embodiments, the synergistic effect is measured in terms of expression of CD95.

In another aspect, the invention provides antibodies that bind to one or more residues within amino acid residues 13-15 and 33-36 of the ECD of human CD40 (SEQ ID NO: 133). In some embodiments, the antibodies bind to one or more amino acids selected from the group consisting of amino acids 33, 34 and 36 of the ECD of human CD40 (SEQ ID NO: 133).

Antibodies of the invention can be full-length, for example, IgG1, IgG2, IgG3, IgG4, IgM, IgA1, IgA2, IgAsec, IgD, and IgE antibodies or sequence variants thereof. Alternatively, the antibodies can be fragments, such as a Fab, F(ab')$_2$, Fv, single chain Fv, isolated complementarity determining region (CDR) or a combination of two or more isolated CDRs. The antibodies can be any known type or species of antibody, including, but not limited to, fully human, humanized, and chimeric antibodies. Preferably the antibodies are IgG2 antibodies. It will be appreciated that certain modifications may be made to the IgG2 sequence within such as deletion of the N-terminal lysine and/or various other mutations known in the art. Thus an IgG2 antibody includes for example antibodies having constant domains with at least 90%, preferably at least 95%, preferably at least 97% and preferably at least 99% sequence identity to a native human IgG2 sequence.

The invention also provides molecular conjugates comprising an antibody of the invention linked to an antigen (including fragments, epitopes and antigenic determinants), such as a tumor antigen, an autoantigen, or a component of a pathogen. For example, the antigen may include a tumor antigen, such as βhCG, gp100 or Pmel17, CEA, gp100, TRP-2, NY-BR-1, NY-CO-58, MN (gp250), idiotype, Tyrosinase, Telomerase, SSX2, MUC-1, MAGE-A3, and high molecular weight-melanoma associated antigen (HMW-MAA) MART1, melan-A, NY-ESO-1, MAGE-1, MAGE-3, WT1, Her2, mesothelin or high molecular weight-melanoma associated antigen (HMW-MAA).

In another embodiment, the molecular complex further includes a therapeutic agent, such as a cytotoxic agent, an immunosuppressive agent, or a chemotherapeutic agent.

In another aspect, the invention provides bispecific molecules comprising antibodies of the invention linked to a second functional moiety having a different binding specificity. For example, in one embodiment, the second molecule may bind to a T cell receptor (e.g., CD3, CD40, or CTLA-4), an NK receptor (e.g., CD56), a B cell receptor (e.g., CD20), or another tumor necrosis factor receptor (e.g., CD95).

Compositions including antibodies, molecular conjugates, or bispecific molecules described herein, formulated with a pharmaceutically acceptable carrier, also are provided. The compositions may further include an adjuvant, immunostimulatory agent (e.g., CD40 ligand, FLT 3 ligand, cytokines, colony-stimulating factors, an anti-CTLA-4 antibody (including without limitation ipilimumab), anti-PD1 antibody (including without limitation MPDL3280A or durvalumab), anti-41BB antibody, anti OX-40 antibody, LPS (endotoxin), ssRNA, dsRNA, Bacille Calmette-Guerin (BCG), Levamisole hydrochloride, intravenous immune globulins and a Toll-like Receptor (TLR) agonist (e.g., TLR3 agonist such as Poly IC, a TLR4 agonist, a TLR5 agonist, a TLR7 agonist, a TLR8 agonist, and a TLR 9 agonist)), immunosuppressive agent, another antibody, or an antigen, or a STING agonist.

Tumor antigens which can be included in the molecular conjugates or compositions of the present invention (e.g., in a vaccine, used in combination with an anti-CD40 antibody of the invention) include any antigen or antigenic determinant which is present on (or associated with) a tumor cell and not typically on normal cells, or an antigen or antigenic determinant which is present on or associated with tumor cells in greater amounts than on normal (non-tumor) cells, or an antigen or antigenic determinant which is present on tumor cells in a different form than that found on normal (non-tumor) cells. Such antigens include tumor-specific antigens, including tumor-specific membrane antigens, tumor-associated antigens, including tumor-associated membrane antigens, embryonic antigens on tumors, growth factor receptors, growth factor ligands, and any other type of antigen that is associated with cancer. A tumor antigen may be, for example, an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. For example, the antigen may include a tumor antigen, such as βhCG, gp100 or Pmel17, CEA, gp100, TRP-2, NY-BR-1, NY-CO-58, MN (gp250), idiotype, Tyrosinase, Telomerase, SSX2, MUC-1, MAGE-A3, and high molecular weight-melanoma associated antigen (HMW-MAA) MART1, melan-A, EGFRvIII, NY-ESO-1, MAGE-1, MAGE-3, WT1, Her2, or mesothelin. Other antigens employed by the present invention (e.g., in a vaccine, used in combination with an anti-CD40 antibody of the invention) include antigens from infectious disease pathogens, such as viruses, bacteria, parasites and fungi, examples of which are disclosed herein.

Nucleic acid molecules encoding all or portions of the heavy and/or light chain variable regions of the antibodies of the invention also are provided, as well as expression vectors comprising these nucleic acids, and host cells comprising such expression vectors. In one embodiment, the nucleic acid sequences are selected from the group consisting of SEQ ID NOs: 87-112, respectively, or nucleic acid sequences having e.g., at least about 85%, 90% or 95% identity to these nucleic acid sequences.

The present invention also provides methods of enhancing an immune response (e.g., a T cell-mediated immune response, and/or an NK-mediated response and/or a B cell-mediated immune response) against an antigen in a subject using the agonistic antibodies described herein. In one embodiment, the antibodies bind to human CD40 (as expressed on a variety of immune cell types), thus triggering the cellular proliferation and activation of antigen-presenting cells (APCs), and activating B-cells, and effector and memory T-cells, which results in enhanced immune responses, e.g., against tumor cells. Accordingly, in one embodiment, the methods include administering an antibody (e.g., a full length antibody or antigen binding portion thereof), composition or bispecific molecule of the invention in an amount effective to induce or enhance an immune response against an antigen. In another embodiment, the methods further includes administering the antigen, e.g., simultaneously, separately or sequentially from the antibody, composition, or bispecific molecule.

Methods for inhibiting the growth of CD40 expressing cells (e.g., in the treatment of cancers) also are provided. For example, agonistic antibodies of the present invention have been shown to increase expression of cell-surface molecules that recruit immune effector cells which leads to cell death, e.g., apoptosis. Therefore, in another embodiment, the method includes administering or contacting the cells with the antibody (e.g., a full length antibody or antigen binding portion thereof), composition or bispecific molecule of the present invention in an amount effective to inhibit growth of CD40 expressing cells.

Further provided are methods for targeting an antigen to a cell, e.g., a cell capable of antigen presentation (such as peripheral blood mononuclear cells (PBMC), monocytes (such as THP-1), B lymphoblastoid cells (such as C1R.A2, 1518 B-LCL) and monocyte-derived DCs in a subject by administering a molecule which binds a receptor on the cell (e.g., the previously described CD40 antibodies) linked to an antigen.

The methods described herein are useful in treating a variety of disorders, particularly cancers (e.g., selected from the group consisting of leukemia, acute lymphocytic leukemia, acute myelocytic leukemia, myeloblasts promyelocyte myelomonocytic monocytic erythroleukemia, chronic leukemia, chronic myelocytic (granulocytic)leukemia, chronic lymphocytic leukemia, mantle cell lymphoma, primary central nervous system lymphoma, Burkitt's lymphoma, marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system). Particular cancers include CD40-expressing tumors selected from the group consisting of chronic lymphocytic leukemia, mantle cell lymphoma, primary central nervous system lymphoma, Burkitt's lymphoma and marginal zone B cell lymphoma.

In another embodiment, the methods can be used to treat or prevent a bacterial, fungal, viral or parasitic infection CD40 expressing cells include any and all cells the express CD40, including, but not limited to antigen-presenting cells (APCs), including dendritic cells (DCs), B-cells, macrophages, and monocytes. CD40 is also expressed on other cell types such as epithelial cells, endothelial cells, and platelets. CD40 expression has been demonstrated on various tumor cells, including B cell lymphoma and renal cancer cells. In a particular embodiment, the CD40 expressing cells include cell lines such as Jurkat cells, Raji cells, Ramos cells and Daudi cells. In another embodiment, the CD40 expressing cells are tumor cells or cancer cells. In another embodiment, CD40-expressing cells include B cells, NK cells, T cells that are found infiltrating tumor or cancer cells, also called tumor infiltrating lymphocytes.

In another embodiment, the invention provides for the use of an antibody, composition or bispecific molecule described herein in the manufacture of a medicament for inducing or enhancing an immune response against an antigen (e.g., a tumor antigen) in a subject. In further embodiments, the invention provides for the use of an antibody or composition described herein in the manufacture of a medicament for (1) increasing an immune response to an antigen, (2) inhibiting growth of CD40 expressing cells, and/or (3) targeting an antigen to an APC.

The present invention also provides methods for detecting the presence or absence of CD40 in a biological sample by (1) contacting a biological sample with an antibody described herein (wherein the antibody is labeled with a detectable substance) and (2) detecting the antibody bound to CD40.

Also provided are kits comprising the compositions (e.g., antibodies and/or bispecific molecules) of the invention and, optionally, instructions for use. The kit can further contain a least one additional reagent, such as a cytokine or complement, or one or more additional antibodies of the invention.

Other features and advantages of the instant invention will be apparent from the following detailed description and claims.

BRIEF DESCRIPTION OF THE DRAWINGS

FIG. 1 provides the values for the equilibrium dissociation constants ($K_D$) and the kinetic association rate constants ($k_{on}$) and dissociation rate constants ($k_{off}$) for antibodies 3C3, 3G5, 1B4, 3B6, and 6H6 as determined by bio-layer interferometry (BLI) using an Octet™ QK$^e$ instrument (Pall ForteBio, Menlo Park, Calif.) according to the manufacturer's guidelines.

FIGS. 4A and 4B are graphs showing the effect of human CD40 antibodies on the binding of soluble CD40 ligand (sCD40L) to CD40 protein by ELISA.

FIGS. 7A and 7B are graphs showing the induction of CD95 on Ramos cells by human CD40 antibodies.

FIGS. 23A-23C are graphs showing levels of separate aminotransferase (AST; 23A), alanine aminotransferase (ALT; 23B) and creatinine kinase (23C) measured in monkeys before and after treatment with CD40 antibodies 3C3 or 3G5 at indicated time points.

FIG. 24 is a graph showing levels of IL-12 (pg/mL) measured in blood from monkeys treated with CD40 antibodies 3C3 or 3G5 at indicated time points.

FIG. 31 provides a table showing cytokine responses in whole blood when this was incubated with the anti-CD40 mAb 3C3.

DETAILED DESCRIPTION OF THE INVENTION

Figure 2:
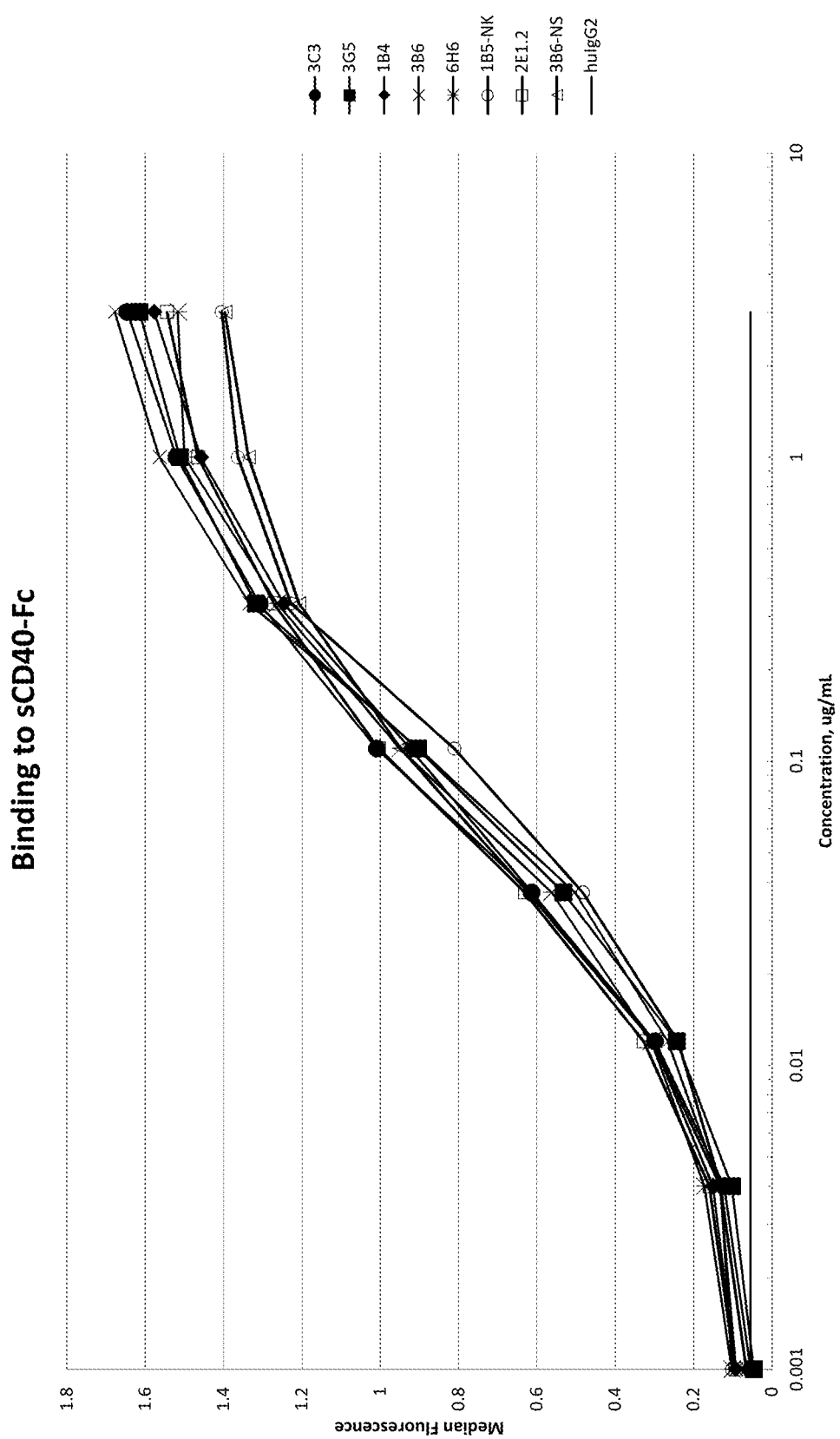
FIG. 2 is a graph showing the binding of human CD40 antibodies (including 3C3, 3G5, 1B4, 3B6, and 6H6) to recombinant purified human CD40 coated microtiter plates using absorbance ($OD_{450}$) in an ELISA as a function of antibody concentration.

The present invention provides anti-CD40 antibodies that exhibit particular functional properties correlating with significant therapeutic benefits involving upregulation of immune function (e.g. T cell mediated immune responses as in vaccine therapies, NK activation in cancer therapies), inhibition of cell growth (e.g., in cancer therapy), and/or enhanced processing and presentation of an antigen by APCs (e.g., in vaccine therapy). These functional features include, for example, an increased immune response to an antigen independent of Fc receptor binding, and/or without induction of antibody-dependent cellular cytotoxicity (ADCC) or complement dependent cellular cytotoxicity (CDC). Additional functional features include, for example, (1) inhibition of (e.g., complete or partial blocking) binding of CD40L (CD154) to CD40 expressing cells by at least 50%, at least 60% or at least 70% (2) blockage of binding of CD40L to human CD40 independent of Fc receptor binding, (3) induction of cellular apoptosis (e.g., as measured by an increase in the expression of CD95), (4) increased T-cell stimulatory activity (e.g., as measured by an increase in the expression of IL-12p40), and/or (5) increased B-cell activation (e.g., as measured by an increase in the expression of at least one cell-surface marker selected from the group consisting of HLA-DR V450, CD54 PE, CD86 APC, and CD83 BV510, CD19 V500, CD54 PE, HLA-DR V450, CD23 PerCP-Cy5.5, CD69 APC, CD86 APC, CD38 PerCP-Cy5.5 and CD71 PE).

In order that the present invention may be more readily understood, certain terms are first defined. Additional definitions are set forth throughout the detailed description.

The term "CD40" (also referred to as "CD40 molecule," "Bp50," "CDW40," "TNFRSF5," "p50," "B cell surface antigen CD40," "B cell-associated molecule," "CD40 antigen," "TNF receptor superfamily member 5," "CD40 type II isoform," "CD40L receptor," "nerve growth factor receptor-related B-lymphocyte activation molecule," or "tumor necrosis factor receptor superfamily member 5") refers to a receptor that is a member of the TNF-receptor superfamily, which binds to ligand CD40L (also referred to as CD154). CD40 is mediates a broad variety of immune and inflammatory responses including T cell-dependent immunoglobulin class switching, and memory B cell development. The term "CD40" includes any variants or isoforms of CD40 which are naturally expressed by cells (e.g., human CD40 deposited with GENBANK® having accession no. P25942). Accordingly, antibodies of the invention may cross-react with CD40 from species other than human. Alternatively, the antibodies may be specific for human CD40 and may not exhibit any cross-reactivity with other species. CD40 or any variants and isoforms thereof, may either be isolated from cells or tissues which naturally express them or be recombinantly produced using well-known techniques in the art and/or those described herein. Preferably the antibodies are targeted to hCD40 which has a normal glycosylation pattern. Genbank® (Accession No. P25942) reports the amino acid sequence of human CD40 as follows (SEQ ID NO:1):

```
MVRLPLQCVL WGCLLTAVHP EPPTACREKQ YLINSQCCSL

CQPGQKLVSD CTEFTETECL PCGESEFLDT WNRETHCHQH

KYCDPNLGLR VQQKGTSETD TICTCEEGWH CTSEACESCV

LHRSCSPGFG VKQIATGVSD TICEPCPVGF FSNVSSAFEK

CHPWTSCETK DLVVQQAGTN KTDVVCGPQD RLRALVVIPI

IFGILFAILL VLVFIKKVAK KPTNKAPHPK QEPQEINFPD

DLPGSNTAAP VQETLHGCQP VTQEDGKESR ISVQERQ
```

The term "CD40L" (also referred to as "CD40 ligand," "CD407L," or "CD154") refers to the ligand for CD40 (see, for example, Schonbeck and Libby (2001) *Cell Mol Life Sci*, 58(1):4-43). CD40L is primarily expressed on activated T cells and is a member of the TNF superfamily of molecules. It binds to CD40 on antigen-presenting cells (APC), which leads to many effects depending on the target cell type (Parham, Peter (2004). *The Immune System* ($2^{nd}$ ed.). Garland Science. Pp. 169-173).

Genbank® (Accession No. NP_000065) reports the amino acid sequence of human CD40L as follows (SEQ ID NO: 2):

```
MIETYNQTSP RSAATGLPIS MKIFMYLLTV FLITQMIGSA

LFAVYLHRRL DKIEDERNLH EDFVFMKTIQ RCNTGERSLS

LLNCEEIKSQ FEGFVKDIML NKEETKKENS FEMQKGDQNP

QIAAHVISEA SSKTTSVLQW AEKGYYTMSN NLVTLENGKQ

LTVKRQGLYY IYAQVTFCSN REASSQAPFI ASLCLKSPGR

FERILLRAAN THSSAKPCGQ QSIHLGGVFE LQPGASVFVN

VTDPSQVSHG TGFTSFGLLK
```

The term "antibody" as referred to herein includes whole antibodies and any antigen binding fragment (i.e., "antigen-binding portion") or single chain thereof. An "antibody" refers, in one preferred embodiment, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., human CD40). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated cmplementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) *Nature Biotech.* 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci* 764:536-546). However, the term "human antibody" does not include antibodies in which CDR sequences derived from the germline of another mammalian species, such as a mouse, have been grafted onto human framework sequences (i.e., humanized antibodies).

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody," as used herein, is intended to refer to an antibody which is substantially free of other antibodies having different antigenic specificities (e.g., an isolated antibody that specifically binds to human CD40 is substantially free of antibodies that specifically bind antigens other than human CD40). An isolated antibody that specifically binds to an epitope of may, however, have cross-reactivity to other CD40 proteins from different species. However, the antibody preferably always binds to human CD40. In addition, an isolated antibody is typically substantially free of other cellular material and/or chemicals. In one embodiment of the invention, a combination of "isolated" antibodies having different CD40 specificities is combined in a well defined composition.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from CD40 are tested for reactivity with the given anti-CD40 antibody. Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

Accordingly, antibodies that bind to the same epitope, or an epitope on CD40 which comprises all or a portion of an epitope recognized by the particular antibodies described herein (e.g., the same or an overlapping region or a region between or spanning the region) also are provided by the invention. Antibodies that bind to the same epitope, or an epitope which comprises all or a portion of an epitope recognized by particular antibody can be identified using routine techniques. Such techniques include, for example, epitope mapping methods, such as, x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

Also provided are antibodies that compete for binding to human CD40 with the antibodies described herein. Antibodies that compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as CD40. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-7}$ M, such as approximately less than $10^{-8}$ M, $10^{-9}$ M or $10^{-10}$ M or even lower when determined by bio-layer interferometry (BLI) using an Octet™ QK$^e$ instrument or by surface plasmon resonance (SPR) technology in a BIACORE 2000 instrument using recombinant human CD40 as the analyte and the antibody as the ligand and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

Also, encompassed by the present invention are antibodies that bind to human CD40 and are capable of increasing an immune response independent of Fc receptor binding. For example, such antibodies exhibit potent agonistic features without cross-linking with an Fc receptor, such as FcγR. These agonistic features include, for example, an increase in T-cell activity and/or an increase in B cell activation as measured, e.g., by an increase in the expression of cell surface markers.

The term "$K_D$," as used herein, is intended to refer to the dissociation equilibrium constant of a particular antibody-antigen interaction. Typically, the human antibodies of the invention bind to CD40 with a dissociation equilibrium constant ($K_D$) of approximately $10^{-8}$ M or less, such as less than $10^{-9}$ M, $10^{-10}$ M, $10^{-11}$ M, or $10^{-12}$ M, or even lower when determined by bio-layer interferometry (BLI) using an Octet™ QK$^e$ instrument or by surface plasmon resonance (SPR) technology in a BIACORE 2000 instrument using recombinant human CD40 as the analyte and the antibody as the ligand.

The term "kd" as used herein, is intended to refer to the off rate constant for the dissociation of an antibody from the antibody/antigen complex.

The term "ka" as used herein, is intended to refer to the on rate constant for the association of an antibody with the antigen.

The term "EC50," as used herein, refers to the concentration of an antibody or an antigen-binding portion thereof, which induces a response, either in an in vitro or an in vivo assay, which is 50% of the maximal response, i.e., halfway between the maximal response and the baseline.

As used herein, "isotype" refers to the antibody class (e.g., IgM or IgG1) that is encoded by heavy chain constant region genes. In one embodiment, a human monoclonal antibody of the invention is of the IgG1 isotype. In another embodiment, a human monoclonal antibody of the invention is of the IgG2 isotype.

The term "binds to immobilized CD40," refers to the ability of a human antibody of the invention to bind to CD40, for example, expressed on the surface of a cell or which is attached to a solid support.

The term "cross-reacts," as used herein, refers to the ability of an antibody of the invention to bind to CD40 from a different species. For example, an antibody of the present invention which binds human CD40 may also bind another species of CD40. As used herein, cross-reactivity is measured by detecting a specific reactivity with purified antigen in binding assays (e.g., SPR, ELISA) or binding to, or otherwise functionally interacting with, cells physiologically expressing CD40. Methods for determining cross-reactivity include standard binding assays as described herein, for example, by bio-layer interferometry (BLI) using an Octet™ QK$^e$ instrument or by Biacore™ surface plasmon resonance (SPR) analysis using a Biacore™ 2000 SPR instrument (Biacore AB, Uppsala, Sweden), or flow cytometric techniques.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human a and human $\Sigma_\mu$ ($\delta$-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a µ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., $V_H$, $V_L$, CDR3) that bind to CD40, is intended to refer to a nucleic acid molecule in which the nucleotide sequences encoding the antibody or antibody portion are free of other nucleotide sequences encoding antibodies or antibody portions that bind antigens other than CD40, which other sequences may naturally flank the nucleic acid in human genomic DNA.

The present invention also encompasses "conservative sequence modifications" of the sequences set forth in SEQ ID Nos: 3-132, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into SEQ ID Nos: 3-148 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CD40 antibody is preferably replaced with another amino acid residue from the same side chain family. Methods of identifying nucleotide and amino acid conservative substitutions which do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997)).

Conservative substitutions maybe made, for example, according to the Table below. For example, amino acids in the same block in the second column and preferably in the same line in the third column may be substituted for each other.

| Aliphatic | Non-Polar | GAP |
| | | ILV |
| | Polar-uncharged | CSTM |
| | | NQ |
| | Polar-charged | DE |
| | | KR |
| Aromatic | | HFWY |

Alternatively, in another embodiment, mutations can be introduced randomly along all or part of an anti-CD40 antibody coding sequence, such as by saturation mutagenesis, and the resulting modified anti-CD40 antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS*, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997)*Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "antigen" refers to any natural or synthetic immunogenic substance, such as a protein, peptide, or hapten. Suitable antigens for use in the present invention (e.g., in a vaccine in combination with an anti-CD40 antibody of the invention) include, for example, infectious disease antigens and tumor antigens, against which protective or therapeutic immune responses are desired, e.g., antigens expressed by a tumor cell or a pathogenic organism or infectious disease antigens. For example, suitable antigens include tumor-associated antigens for the prevention or treatment of cancers. Examples of tumor-associated antigens include, but are not limited to, sequences comprising all or part of the sequences of βhCG, gp100 or Pmel17, HER2/neu, WT1, mesothelin, CEA, gp100, MART1, TRP-2, melan-A, NY-ESO-1, NY-BR-1, NY-CO-58, MN (gp250), idiotype, MAGE-1, MAGE-3, MAGE-A3, Tyrosinase, Telomerase, SSX2 and MIUC-1 antigens, and germ cell derived tumor antigens. Tumor associated antigens also include the blood group antigens, for example, $Le^a$, $Le^b$, LeX, LeY, H-2, B-1, B-2 antigens. Alternatively, more than one antigen can be included within the antigen-antibody constructs of the invention. For example, a MAGE antigen can be combined with other antigens such as melanin A, tyrosinase, and gp100 along with adjuvants such as GM-CSF or IL-12, and linked to an anti-APC antibody.

Other suitable antigens include viral antigens for the prevention or treatment of viral diseases. Examples of viral antigens include, but are not limited to, HIV-1 gag, HIV-1 env, HIV-1 nef, HBV (surface or core antigens), HPV, FAS, HSV-1, HSV-2, p17, ORF2 and ORF3 antigens. Examples of bacterial antigens include, but are not limited to, *Toxoplasma gondii* or *Treponema pallidum*. The antibody-bacterial antigen conjugates of the invention can be in the treatment or prevention of various bacterial diseases such as Anthrax, Botulism, Tetanus, *Chlamydia*, Cholera, Diphtheria, Lyme Disease, Syphilis and Tuberculosis. Other suitable antigens from infectious disease pathogens, such as viruses, bacteria, parasites and fungi are disclosed below.

Sequences of the foregoing antigens are well known in the art. For example, an example of a MAGE-3 cDNA sequence is provided in U.S. Pat. No. 6,235,525 (Ludwig Institute for Cancer Research); examples of NY-ESO-1 nucleic acid and protein sequences are provided in U.S. Pat. Nos. 5,804,381 and 6,069,233 (Ludwig Institute for Cancer Research); examples of Melan-A nucleic acid and protein sequences are provided in U.S. Pat. Nos. 5,620,886 and 5,854,203 (Ludwig Institute for Cancer Research); examples of NY-BR-1 nucleic acid and protein sequences are provided in U.S. Pat. Nos. 6,774,226 and 6,911,529 (Ludwig Institute for Cancer Research) and examples of NY-CO-58 nucleic acid and protein sequences are provided in WO 02090986 (Ludwig Institute for Cancer Research); an example of an amino acid sequence for the HER-2/neu protein is available at GENBANK® Accession No. AAA58637; and a nucleotide sequence (mRNA) for human carcinoembryonic antigen-like 1 (CEA-1) is available at GENBANK® Accession No. NM_020219.

An HPV antigen that may be used in the compositions and the methods of the invention may include, for example an HPV-16 antigen, an HPV-18 antigen, an HPV-31 antigen, an HPV-33 antigen and/or an HPV-35 antigen; and is suitably an HPV-16 antigen and/or an HPV-18 antigen. A genome of HPV-16 is described in Virology, 145:181-185 (1985) and DNA sequences encoding HPV-18 are described in U.S. Pat. No. 5,840,306, the disclosures of which are incorporated by reference herein in their entirety. HPV-16 antigens (e.g., seroreactive regions of the E1 and/or E2 proteins of HPV-16) are described in U.S. Pat. No. 6,531,127, and HPV-18 antigens (e.g., seroreactive regions of the L1 and/or L2 proteins of HPV-18) are described in U.S. Pat. No. 5,840,306, the disclosures of which are incorporated by reference herein. Similarly, a complete genome for HBV is available at GENBANK® Accession No. NC_003977, the disclosure of which is incorporated herein. The genome of HCV is described in European Patent Application No. 318 216, the disclosure of which is incorporated herein. PCT/US90/01348, incorporated by reference herein, discloses sequence information of clones of the HCV genome, amino acid sequences of HCV viral proteins and methods of making and using such compositions for HCV vaccines comprising HCV proteins and peptides derived there from.

Antigenic peptides of proteins (i.e., those containing T cell epitopes) can be identified in a variety of manners well known in the art. For example, T cell epitopes can be predicted by analyzing the sequence of the protein using web-based predictive algorithms (BIMAS & SYFPEITHI) to generate potential MHC class I and II-binding peptides that match an internal database of 10,000 well characterized MHC binding peptides previously defined by CTLs. High scoring peptides can be ranked and selected as "interesting" on the basis of high affinity to a given MHC molecule.

Another method for identifying antigenic peptides containing T cell epitopes is by dividing the protein into non-overlapping peptides of desired length or overlapping peptides of desired lengths which can be produced recombinantly, synthetically, or in certain limited situations, by chemical cleavage of the protein and tested for immunogenic properties, e.g., eliciting a T cell response (i.e., proliferation or lymphokine secretion).

In order to determine precise T cell epitopes of the protein by, for example, fine mapping techniques, a peptide having T cell stimulating activity and thus comprising at least one T cell epitope, as determined by T cell biology techniques, can be modified by addition or deletion of amino acid residues at either the amino or carboxy terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. Peptides are selected based on various factors, including the strength of the T cell response to the peptide (e.g., stimulation index). The physical and chemical properties of these selected peptides (e.g., solubility, stability) can then be examined to determine whether the peptides are suitable for use in therapeutic compositions or whether the peptides require modification.

The term "antigen presenting cell" or "APC" is a cell that displays foreign antigen complexed with MHC on its surface. T-cells recognize this complex using T-cell receptor (TCR). Examples of APCs include, but are not limited to, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

Examples of APC receptors include, but are not limited to C-type lectins, such as, the human Dendritic and Epithelial Cell 205 receptor (DEC-205), and the human macrophage mannose receptor.

The term "antigen presentation" refers to the process by which APCs capture antigens and enables their recognition by T-cells, e.g., as a component of an MHC-I and/or MHC-II conjugate.

"MHC molecules" include two types of molecules, MHC class I and MHC class II. MHC class I molecules present antigen to specific CD8+ T cells and MHC class II molecules present antigen to specific CD4+ T cells. Antigens delivered exogenously to APCs are processed primarily for association with MHC class II. In contrast, antigens delivered endogenously to APCs are processed primarily for association with MHC class I.

As used herein, the term "immunostimulatory agent" includes but is not limited to compounds capable of stimulating APCs, such as DCs and macrophages. For example, suitable immunostimulatory agents for use in the present invention are capable of stimulating APCs, so that the maturation process of the APCs is accelerated, the proliferation of APCs is increased, and/or the recruitment or release of co-stimulatory molecules (e.g., CD80, CD86, ICAM-1, MHC molecules and CCR7) and pro-inflammatory cytokines (e.g., IL-10, IL-6, IL-12, IL-15, and IFN-γ) is upregulated. Suitable immunostimulatory agents are also capable of increasing T cell proliferation. Such immunostimulatory agents include, but are not be limited to, CD27 ligand; FLT 3 ligand; cytokines, such as IFN-α, IFN-β, IFN-γ and IL-2; colony-stimulating factors, such as G-CSF (granulocyte colony-stimulating factor) and GM-CSF (granulocyte-macrophage colony-stimulating factor); an anti-CTLA-4 antibody, anti-PD1 antibody, anti-41BB antibody, or anti-OX-40 antibody; LPS (endotoxin); ssRNA; dsRNA; Bacille Calmette-Guerin (BCG); Levamisole hydrochloride; and intravenous immune globulins. In one embodiment an immunostimulatory agent may be a Toll-like Receptor (TLR) agonist. For example the immunostimulatory agent may be a TLR3 agonist such as double-stranded inosine:cytosine polynucleotide (Poly I:C, for example available as Ampligen™ from Hemispherx Bipharma, PA, US or Poly IC:LC from Oncovir) or Poly A:U; a TLR4 agonist such as monophosphoryl lipid A (MPL) or RC-529 (for example as available from GSK, UK); a TLR5 agonist such as flagellin; a TLR7 or TLR8 agonist such as an imidazoquinoline TLR7 or TLR 8 agonist, for example imiquimod (e.g., Aldara™) or resiquimod and related imidazoquinoline agents (for example as available from 3M Corporation); or a TLR 9 agonist such as a deoxynucleotide with unmethylated CpG motifs (so-called "CpGs", for example as available from Coley Pharmaceutical). A preferred immunostimulatory agent is a TLR3 agonist, preferably Poly I:C. Such immunostimulatory agents may be administered simultaneously, separately or sequentially with the antibodies and constructs of the present invention and may also be physically linked to the antibodies and constructs.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, the term antigen "cross-presentation" refers to presentation of exogenous protein antigens to T cells via MHC class I and class II molecules on APCs.

As used herein, the term "T cell-mediated response" refers to any response mediated by T cells, including effector T cells (e.g., CD8+ cells) and helper T cells (e.g., CD4+ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by CD8+ T cells.

As used herein, the terms "inhibits" or "blocks" (e.g., referring to inhibition/blocking of binding of CD40L to CD40 on cells) are used interchangeably and encompass both partial and complete inhibition/blocking. The inhibition/blocking of CD40L preferably reduces or alters the normal level or type of activity that occurs when CD40L binding occurs without inhibition or blocking. Inhibition and blocking are also intended to include any measurable decrease in the binding affinity of CD40L when in contact with an anti-CD40 antibody as compared to CD40L not in contact with an anti-CD40 antibody, e.g., inhibits binding of CD40L by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. In a particular embodiment, the anti-CD40 antibody inhibits binding of CD40L by at least about 70% as measured, e.g., by a BLI or SPR (Biacore) assay. In another embodiment, the anti-CD40 antibody inhibits binding of CD40L by at least about 80%.

As used herein, the term "inhibits growth" (e.g., referring to cells) is intended to include any measurable decrease in the growth of a cell, e.g., the inhibition of growth of a cell by at least about 10%, 20%, 30%, 40%, 50%, 60%, 70%, 80%, 90%, 99%, or 100%.

The terms "inducing an immune response," "increasing an immune response," and "enhancing an immune response" are used interchangeably and refer the stimulation of an immune response (i.e., either passive or adaptive) to a particular antigen.

The terms "induce" and "increase" as used with respect to inducing CDC or ADCC refer to the stimulation of particular direct cell killing mechanisms. For example, in one embodiment, the antibody induces at least about 20, 25, 30, 35, 40, 45, 50, 55, or 60% lysis via CDC of CD40 expressing cells at a concentration of 10 μg/ml. In a preferred embodiment, the antibody induces at least about 40% lysis via CDC of CD40 expressing cells at a concentration of 10 g/ml. In another embodiment, the antibody induces at least about 20, 25, 30, 35, 40, 45, 50, 55, 60, 65, 70, 75, 80, or 85% lysis via ADCC (i.e., specific lysis) of CD40 expressing cells at a concentration of 10 μg/ml. In one embodiment, the antibody induces at least about 40% lysis via ADCC of CD40 expressing cells at a concentration of 10 μg/ml.

The terms "treat," "treating," and "treatment," as used herein, refer to therapeutic or preventative measures described herein. The methods of "treatment" employ administration to a subject, in need of such treatment, a human antibody of the present invention, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

As used herein, the term "synergistic" means that administration of two drugs produce a greater effect when used in combination than would be expected from adding the individual effects of the two components, for example greater than two times, greater than three times, greater than five times or greater than ten times what would be expected from adding the individual effects of the two components. For example, drug interactions can be analyzed using the commercial software package Calcusyn, which is based on the median effect model of Chou and Talalay (Chou, T. C. & Talalay, P. (1984) Adv. Enzyme Regul. 22, 27-55. Quantatative analysis of dose-effect relationships: the combined effects of multiple drugs or enzyme inhibitors). A Combination Index (C.I.) of 1 indicated an additive drug interaction, whereas a C.I. greater than 1 was antagonistic and a score lower than 1 was synergistic. The CI value definitions are as follows: 1.45-1.2 is moderately antagonistic, 1.2-1.1 is slightly antagonistic, 1.1-0.9 is additive, 0.9-0.85 is slightly synergistic, 0.85-0.7 is moderately synergistic and 0.7-0.3 is synergistic.

The term "patient" includes human and other mammalian subjects that receive either prophylactic or therapeutic treatment.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

Various aspects of the invention are described in further detail in the following subsections.

I. Production of Antibodies to CD40

Anti-CD40 antibodies of the invention can be produced using a variety of known techniques, such as the standard somatic cell hybridization technique described by Kohler and Milstein, Nature 256: 495 (1975). Although somatic cell hybridization procedures can be used, in principle, other techniques for producing monoclonal antibodies also can be employed, e.g., viral or oncogenic transformation of B lymphocytes, phage display technique using libraries of human antibody genes.

In a particular (exemplified) embodiment, a mouse (e.g., an H2L2 strain of Harbour® transgenic mice) or other appropriate host animal is immunized with a suitable antigen in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell (Goding, Monoclonal Antibodies: Principles and Practice, pp. 59-103 (Academic Press, 1986)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Goding, Monoclonal Antibodies:Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In another embodiment, antibodies directed against CD40 are generated using transgenic or transchromosomal mice carrying parts of the human immune system rather than the mouse system. In one embodiment, the invention employs transgenic mice, referred to herein as "HuMAb mice" which contain a human immunoglobulin gene miniloci that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg, N. et al. (1994) Nature 368(6474): 856-859). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. Vol. 13: 65-93, and Harding, F. and Lonberg, N. (1995) Ann. N.Y. Acad. Sci 764:536-546). The preparation of HuMAb mice is described in detail in Section II below and in Taylor, L. et al. (1992) Nucleic Acids Research 20:6287-6295; Chen, J. et al. (1993) International Immunology 5: 647-656; Tuaillon et al. (1993) Proc. Nat. Acad. Sci USA 90:3720-3724; Choi et al. (1993) Nature Genetics 4:117-123; Chen, J. et al. (1993) EMBO J. 12: 821-830; Tuaillon et al. (1994) J Immunol. 152:2912-2920; Lonberg et al., (1994) Nature 368(6474): 856-859; Lonberg, N. (1994) Handbook of Experimental Pharmacology 113:49-101; Taylor, L. et al. (1994) International Immunology 6: 579-591; Lonberg, N. and Huszar, D. (1995) Intern. Rev. Immunol. Vol. 13: 65-93; Harding, F. and Lonberg, N. (1995) Ann. N.Y. Acad. Sci 764:536-546; Fishwild, D. et al. (1996) Nature Biotechnology 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992.

In another embodiment, antibodies that bind human CD40 can be isolated from antibody phage libraries generated using the techniques described in, for example, McCafferty et al., Nature, 348:552-554 (1990). Clackson et al., Nature, 352:624-628 (1991), Marks et al., J. Mol. Biol., 222:581-597 (1991) and Hoet et al (2005) Nature Biotechnology 23, 344-348; U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Additionally, production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)) may also be used.

In a particular embodiment, the antibody that binds human CD40 is produced using the phage display technique described by Hoet et al., supra. This technique involves the generation of a human Fab library having a unique combination of immunoglobulin sequences isolated from human donors and having synthetic diversity in the heavy-chain CDRs is generated. The library is then screened for Fabs that bind to human CD40.

The preferred animal system for generating hybridomas which produce antibodies of the invention is the murine system. Hybridoma production in the mouse is well known in the art, including immunization protocols and techniques for isolating and fusing immunized splenocytes.

Generation of Transfectomas Producing Monoclonal Antibodies to CD40

Antibodies of the invention also can be produced in a host cell transfectoma using, for example, a combination of recombinant DNA techniques and gene transfection methods as is well known in the art (Morrison, S. (1985) Science 229:1202).

For example, in one embodiment, the gene(s) of interest, e.g., human antibody genes, can be ligated into an expression vector such as a eukaryotic expression plasmid such as used by GS gene expression system disclosed in WO 87/04462, WO 89/01036 and EP 338 841 or other expression systems well known in the art. The purified plasmid with the cloned antibody genes can be introduced in eukaryotic host cells such as CHO-cells or NSO-cells or alternatively other eukaryotic cells like a plant derived cells, fungi or yeast cells. The method used to introduce these genes could be methods described in the art such as electroporation, lipofectine, lipofectamine or other. After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively these cloned antibody genes can be expressed in other expression systems such as *E. coli* or in complete organisms or can be synthetically expressed.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, *Nature* 332:323-327; Jones, P. et al., 1986, *Nature* 321:522-525; and Queen, C. et al., 1989, *Proc. Nat. Acad. See. U.S.A.* 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266: 19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors were constructed so that PCR amplified V heavy and V kappa light chain cDNA sequences could be used to reconstruct complete heavy and light chain minigenes. These plasmids can be used to express completely human IgG$_1$κ or IgG$_4$κ antibodies. Fully human and chimeric antibodies of the present invention also include IgG2, IgG3, IgE, IgA, IgM, and IgD antibodies. Similar plasmids can be constructed for expression of other heavy chain isotypes, or for expression of antibodies comprising lambda light chains.

Thus, in another aspect of the invention, structural features of anti-CD40 antibodies of the invention are used to create structurally related anti-CD40 antibodies that retain at least one functional property of the antibodies of the invention, such as, for example, (a) inducing or enhancing an immune response to an antigen independent of Fc receptor binding;

(b) inducing or enhancing an immune response to an antigen without inducing antibody-dependent cellular cytotoxicity (ADCC) of CD40 expressing cells;

(c) inducing or enhancingan immune response to an antigen without inducing complement dependent cellular cytotoxicity (CDC) of CD40 expressing cells; and/or (d) capable of synergising with CD40L; and/or Additional features may include, for example:

(d) no inhibiting or no blocking binding of CD40L;

(e) inhibiting or blocking binding of CD40L;

(f) inhibiting or blocking binding of CD40L to human CD40 independent of Fc receptor binding;

(g) inducing or enhancing cellular apoptosis of a tumor cell;

(h) inducing or enhancing T-cell stimulatory activity of a cell (e.g., as measured by an increase in the expression of IL-12p40); and/or (i) inducing or enhancing B-cell activation (e.g., as measured by an increase in the expression of at least one cell-surface marker selected from the group consisting of HLA-DR V450, CD54 PE, CD86 APC, and CD83 BV510, CD19 V500, CD54 PE, HLA-DR V450, CD23 PerCP-Cy5.5, CD69 APC, CD86 APC, CD38 PerCP-Cy5.5 and CD71 PE).

In one embodiment, one or more CDR regions of antibodies of the invention can be combined recombinantly with known framework regions and CDRs to create additional, recombinantly-engineered, anti-CD40 antibodies of the invention. The heavy and light chain variable framework regions can be derived from the same or different antibody sequences. The antibody sequences can be the sequences of naturally occurring antibodies or can be consensus sequences of several antibodies. See Kettleborough et al., *Protein Engineering* 4:773 (1991); Kolbinger et al., *Protein Engineering* 6:971 (1993) and Carter et al., WO 92/22653.

Accordingly, in another embodiment, the invention provides a method for preparing an anti-CD40 antibody including: preparing an antibody including (1) heavy chain framework regions and heavy chain CDRs, where at least one of the heavy chain CDRs includes an amino acid sequence selected from the amino acid sequences of CDRs shown in SEQ ID NOs:5, 6, 7, 8, 9, 10, 19, 20, 21, 22, 23, 24, 33, 34, 35, 36, 37, 38, 47, 48, 49, 51, 52, 61, 62, 63, 64, 65, 66, 75, 76, 77, 78, 79, 80, 89, 90, 91, 92, 93, 94, 103, 104, 105, 106, 107, 108; and (2) light chain framework regions and light chain CDRs, where at least one of the light chain CDRs includes an amino acid sequence selected from the amino acid sequences of CDRs shown in SEQ ID NOs:11, 12, 13, 14, 15, 16, 25, 26, 27, 28, 29, 30, 39, 40, 41, 42, 43, 44, 53, 54, 55, 56, 57, 58, 67, 68, 69, 70, 71, 72, 81, 82, 83, 84, 85, 86, 95, 96, 97, 98, 99, 100, 109, 110, 111, 112, 113, 114; where the antibody retains the ability to bind to CD40. The ability of the antibody to bind CD40 can be determined using standard binding assays, such as those set forth in the Examples (e.g., an ELISA or a FLISA).

It is well known in the art that antibody heavy and light chain CDR3 domains play a particularly important role in the binding specificity/affinity of an antibody for an antigen (see, Hall et al., *J Imunol.*, 149:1605-1612 (1992); Polymenis et al., *J Immunol.*, 152:5318-5329 (1994); Jahn et al., *Immunobiol.*, 193:400-419 (1995); Klimka et al., *Brit. J. Cancer,* 83:252-260 (2000); Beiboer et al., *J Mol. Biol,* 296:833-849 (2000); Rader et al., *Proc. Natl. Acad. Sci. USA,* 95:8910-8915 (1998); Barbas et al., *J. Am. Chem. Soc.,* 116:2161-2162 (1994); Ditzel et al., *J. Immunol.,* 157:739-749 (1996)). Accordingly, the recombinant antibodies of the invention prepared as set forth above preferably comprise the heavy and/or light chain CDR3s of antibodies 3C3, 3G5, 1B4, 3B6, 6H6, 2E1.2, 1B5-NK, and 3B6-NS. The antibodies further can comprise the CDR2s of antibodies 3C3, 3G5, 1B4, 3B6, 6H6, 2E1.2, 1B5-NK, and 3B6-NS. The antibodies further can comprise the CDR1s of antibodies 3C3, 3G5, 1B4, 3B6, 6H6, 2E1.2, 1B5-NK, and 3B6-NS. The antibodies can further comprise any combinations of the CDRs.

Accordingly, in another embodiment, the invention further provides anti-CD40 antibodies comprising: (1) heavy chain framework regions, a heavy chain CDR1 region, a heavy chain CDR2 region, and a heavy chain CDR3 region, wherein the heavy chain CDR3 region is selected from the CDR3s of 3C3, 3G5, 1B4, 3B6, 6H6, 2E1.2, 1B5-NK, or 3B6-NS, and (2) light chain framework regions, a light chain CDR1 region, a light chain CDR2 region, and a light chain CDR3 region, wherein the light chain CDR3 region is selected from the CDR3s of 3C3, 3G5, 1B4, 3B6, 6H6, 2E1.2, 1B5-NK, or 3B6-NS, wherein the antibody binds CD40. The antibody may further include the heavy chain CDR2 and/or the light chain CDR2 of antibodies 3C3, 3G5, 1B4, 3B6, 6H6, 2E1.2, 1B5-NK, or 3B6-NS. The antibody may further comprise the heavy chain CDR1 and/or the light chain CDR1 of antibodies 3C3, 3G5, 1B4, 3B6, 6H6, 2E1.2, 1B5-NK, or 3B6-NS.

Generation of Antibodies Having Modified Sequences

In another embodiment, the variable region sequences, or portions thereof, of the anti-CD40 antibodies of the invention are modified to create structurally related anti-CD40 antibodies that retain binding (i.e., to the same epitope as the unmodified antibody) and, thus, are functionally equivalent. Methods for identifying residues that can be altered without removing antigen binding are well-known in the art (see, e.g., Marks et al. (*Biotechnology* (1992) 10(7):779-83 (monoclonal antibodies diversification by shuffling light chain variable regions, then heavy chain variable regions with fixed CDR3 sequence changes), Jespers et al. (1994) Biotechnology 12(9):899-903 (selection of human antibodies from phage display repertoires to a single epitope of an antigen), Sharon et al. (1986) *PNAS USA* 83(8):2628-31 (site-directed mutagenesis of an invariant amino acid residue at the variable-diversity segments junction of an antibody); Casson et al. (1995) *J. Immunol.* 155(12):5647-54 (evolution of loss and change of specificity resulting from random mutagenesis of an antibody heavy chain variable region).

Accordingly, in one aspect of the invention, the CDR1, 2, and/or 3 regions of the engineered antibodies described above can comprise the exact amino acid sequence(s) as those of antibodies 3C3, 3G5, 1B4, 3B6, 6H6, 2E1.2, 1B5-NK, or 3B6-NS disclosed herein. However, in other aspects of the invention, the antibodies comprise derivatives from the exact CDR sequences of 3C3, 3G5, 1B4, 3B6, 6H6, 2E1.2, 1B5-NK, or 3B6-NS, yet still retain the ability of to bind CD40 effectively. Such sequence modifications may include one or more amino acid additions, deletions, or substitutions, e.g., conservative sequence modifications as described above. Sequence modifications may also be based on the consensus sequences described above for the particular CDR1, CDR2, and CDR3 sequences of antibodies 3C3, 3G5, 1B4, 3B6, 6H6, 2E1.2, 1B5-NK, or 3B6-NS.

Accordingly, in another embodiment, the engineered antibody may be composed of one or more CDRs that are, for example, 90%, 95%, 98% or 99.5% identical to one or more CDRs of antibodies 3C3, 3G5, 1B4, 3B6, 6H6, 2E1.2, 1B5-NK, or 3B6-NS. Ranges intermediate to the above-recited values, e.g., CDRs that are 90-95%, 95-98%, or 98-100% identical identity to one or more of the above sequences are also intended to be encompassed by the present invention.

In another embodiment, one or more residues of a CDR may be altered to modify binding to achieve a more favored on-rate of binding, a more favored off-rate of binding, or both, such that an idealized binding constant is achieved. Using this strategy, an antibody having ultra high binding affinity of, for example, $10^{10}$ $M^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

In addition to or instead of modifications within the CDRs, modifications can also be made within one or more of the framework regions, FR1, FR2, FR3 and FR4, of the heavy and/or the light chain variable regions of a antibody, so long as these modifications do not eliminate the binding affinity of the antibody. For example, one or more non-germline amino acid residues in the framework regions of the heavy and/or the light chain variable region of a antibody of the invention, is substituted with a germline amino acid residue, i.e., the corresponding amino acid residue in the human germline sequence for the heavy or the light chain variable region, which the antibody has significant sequence identity with. For example, an antibody chain can be aligned to a germline antibody chain which it shares significant sequence identity with, and the amino acid residues which do not match between antibody framework sequence and the germline chain framework can be substituted with corresponding residues from the germline sequence. When an amino acid differs between a antibody variable framework region and an equivalent human germline sequence variable framework region, the antibody framework amino acid should usually be substituted by the equivalent human germline sequence amino acid if it is reasonably expected that the amino acid falls within one of the following categories:

(1) an amino acid residue which noncovalently binds antigen directly, (2) an amino acid residue which is adjacent to a CDR region, (3) an amino acid residue which otherwise interacts with a CDR region (e.g., is within about 3-6 Å of a CDR region as determined by computer modeling), or (4) an amino acid reside which participates in the VL-VH interface.

Residues which "noncovalently bind antigen directly" include amino acids in positions in framework regions which have a good probability of directly interacting with amino acids on the antigen according to established chemical forces, for example, by hydrogen bonding, Van der Waals forces, hydrophobic interactions, and the like. Accordingly, in one embodiment, an amino acid residue in the framework region of a antibody of the invention is substituted with the corresponding germline amino acid residue which noncovalently binds antigen directly.

Residues which are "adjacent to a CDR region" include amino acid residues in positions immediately adjacent to one or more of the CDRs in the primary sequence of the antibody, for example, in positions immediately adjacent to a CDR as defined by Kabat, or a CDR as defined by Chothia (see e.g., Chothia and Lesk *J. Mol. Biol.* 196:901 (1987)). Accordingly, in one embodiment, an amino acid residue within the framework region of an antibody of the invention is substituted with a corresponding germline amino acid residue which is adjacent to a CDR region.

Residues that "otherwise interact with a CDR region" include those that are determined by secondary structural analysis to be in a spatial orientation sufficient to affect a CDR region. Such amino acids will generally have a side chain atom within about 3 angstrom units (A) of some atom in the CDRs and must contain an atom that could interact with the CDR atoms according to established chemical forces, such as those listed above. Accordingly, in one embodiment, an amino acid residue within the framework region of an antibody of the invention is substituted with the corresponding germline amino acid residue which otherwise interacts with a CDR region.

The amino acids at several positions in the framework are known to be important for determining CDR confirmation (e.g., capable of interacting with the CDRs) in many antibodies (Chothia and Lesk, supra, Chothia et al., supra and Tramontano et al., J. Mol. Biol. 215:175 (1990), all of which are incorporated herein by reference). These authors identified conserved framework residues important for CDR conformation by analysis of the structures of several known antibodies. The antibodies analyzed fell into a limited number of structural or "canonical" classes based on the conformation of the CDRs. Conserved framework residues within members of a canonical class are referred to as "canonical" residues. Canonical residues include residues 2, 25, 29, 30, 33, 48, 64, 71, 90, 94 and 95 of the light chain and residues 24, 26, 29, 34, 54, 55, 71 and 94 of the heavy chain. Additional residues (e.g., CDR structure-determining residues) can be identified according to the methodology of Martin and Thorton (1996) *J. Mol. Biol.* 263:800. Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. Additional residues which may effect conformation of the CDRs can be identified according to the methodology of Foote and Winter (1992) *J. Mol. Biol.* 224:487. Such residues are termed "vernier" residues and are those residues in the framework region closely underlying (i.e., forming a "platform" under) the CDRs.

Residues which "participate in the VL-VH interface" or "packing residues" include those residues at the interface between VL and VH as defined, for example, by Novotny and Haber, *Proc. Natl. Acad. Sci. USA,* 82:4592-66 (1985) or Chothia et al, supra.

Occasionally, there is some ambiguity about whether a particular amino acid falls within one or more of the above-mentioned categories. In such instances, alternative variant antibodies are produced, one of which has that particular substitution, the other of which does not. Alternative variant antibodies so produced can be tested in any of the assays described herein for the desired activity, and the preferred antibody selected.

Additional candidates for substitution within the framework region are amino acids that are unusual or "rare" for an antibody at that position. These amino acids can be substituted with amino acids from the equivalent position of the human germline sequence or from the equivalent positions of more typical antibodies. For example, substitution may be desirable when the amino acid in a framework region of the antibody is rare for that position and the corresponding amino acid in the germline sequence is common for that position in immunoglobulin sequences; or when the amino acid in the antibody is rare for that position and the corresponding amino acid in the germline sequence is also rare, relative to other sequences. It is contemplated that by replacing an unusual amino acid with an amino acid from the germline sequence that happens to be typical for antibodies, the antibody may be made less immunogenic. Substitution may also be desirable, for example in cases of unpaired cysteine residues or putative N-linked glycosylation sites.

The term "rare", as used herein, indicates an amino acid occurring at that position in less than about 20%, preferably less than about 10%, more preferably less than about 5%, even more preferably less than about 3%, even more preferably less than about 2% and even more preferably less than about 1% of sequences in a representative sample of sequences, and the term "common", as used herein, indicates an amino acid occurring in more than about 25% but usually more than about 50% of sequences in a representative sample. For example, all light and heavy chain variable region sequences are respectively grouped into "subgroups" of sequences that are especially homologous to each other and have the same amino acids at certain critical positions (Kabat et al., supra). When deciding whether an amino acid in an antibody sequence is "rare" or "common" among sequences, it will often be preferable to consider only those sequences in the same subgroup as the antibody sequence.

In general, the framework regions of antibodies are usually substantially identical, and more usually, identical to the framework regions of the human germline sequences from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting immunoglobulin. Thus, in one embodiment the variable framework region of the antibody shares at least 85% sequence identity to a human germline variable framework region sequence or consensus of such sequences. In another embodiment, the variable framework region of the antibody shares at least 90%, 95%, 96%, 97%, 98% or 99% sequence identity to a human germline variable framework region sequence or consensus of such sequences.

In addition to simply binding CD40, an antibody may be selected for its retention of other functional properties of antibodies of the invention, such as, for example:

(a) inducing or enhancing an immune response to an antigen independent of Fc receptor binding;

(b) inducing or enhancing an immune response to an antigen without inducing antibody-dependent cellular cytotoxicity (ADCC) of CD40 expressing cells;

(c) inducing or enhancingan immune response to an antigen without inducing complement dependent cellular cytotoxicity (CDC) of CD40 expressing cells; and/or (d) capable of synergising with CD40L.

Additional features may include, for example:

(e) no blocking of binding of CD40L to human CD40 independent of Fc receptor binding;

(f) blocking of binding of CD40L to human CD40 independent of Fc receptor binding;

(g) activation of human CD40 expressed on an APC, independent of Fc receptor binding;

(h) induction of apoptosis of a tumor cell;

(i) T-cell stimulatory activity; and/or (j) enhanced B-cell activation.

Characterization of Monoclonal Antibodies to CD40

Monoclonal antibodies of the invention can be characterized for binding to CD40 using a variety of known techniques. Generally, the antibodies are initially characterized by ELISA. Briefly, microtiter plates can be coated with purified CD40 in PBS, and then blocked with irrelevant proteins such as bovine serum albumin (BSA) diluted in PBS. Dilutions of plasma from CD40-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

An ELISA assay as described above can be used to screen for antibodies and, thus, hybridomas that produce antibodies that show positive reactivity with the CD40 immunogen. Hybridomas that bind, preferably with high affinity, to CD40 can then be subcloned and further characterized. One clone from each hybridoma, which retains the reactivity of the parent cells (by ELISA), can then be chosen for making a cell bank, and for antibody purification.

To purify anti-CD40 antibodies, selected hybridomas can be grown in roller bottles, two-liter spinner-flasks or other culture systems. Supernatants can be filtered and concentrated before affinity chromatography with protein A-Sepharose (Pharmacia, Piscataway, N.J.) to purify the protein. After buffer exchange to PBS, the concentration can be determined by $OD_{280}$ using 1.43 extinction coefficient or preferably by nephelometric analysis. IgG can be checked by gel electrophoresis and by antigen specific method.

To determine if the selected anti-CD40 monoclonal antibodies bind to unique epitopes, each antibody can be biotinylated using commercially available reagents (Pierce, Rockford, Ill.). Biotinylated MAb binding can be detected with a streptavidin labeled probe. To determine the isotype of purified antibodies, isotype ELISAs can be performed using art recognized techniques. For example, wells of microtiter plates can be coated with 10 µg/ml of anti-Ig overnight at 4° C. After blocking with 5% BSA, the plates are reacted with 10 µg/ml of monoclonal antibodies or purified isotype controls, at ambient temperature for two hours. The wells can then be reacted with either IgG or other isotype specific conjugated probes. Plates are developed and analyzed as described above.

To test the binding of monoclonal antibodies to live cells expressing CD40, flow cytometry can be used. Briefly, cell lines and/or human PBMCs expressing membrane-bound CD40 (grown under standard growth conditions) are mixed with various concentrations of monoclonal antibodies in PBS containing 0.1% BSA at 4° C. for 1 hour. After washing, the cells are reacted with Fluorescein-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-CD40 IgGs can be further tested for reactivity with the CD40 antigen by Western blotting. Briefly, cell extracts from cells expressing CD40 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, Mo.).

Methods for analyzing binding affinity, cross-reactivity, and binding kinetics of various anti-CD40 antibodies include standard assays known in the art, for example, Biacore™ surface plasmon resonance (SPR) analysis using a Biacore™ 2000 SPR instrument (Biacore AB, Uppsala, Sweden), or bio-layer interferometry (BLI) using an Octet™ QK$^e$ instrument as described in the examples.

Agonistic anti-CD40 antibodies which bind to the same epitope as that of anti-CD40 antibodies 3C3, 3G5, 1B4, 3B6, 6H6, 2E1.2, 1B5-NK, and 3B6-NS (as determined by a given epitope mapping technique) also are provided herein. For example, as described in Example 17, antibodies of the invention (e.g., antibody 3C3) bind to one or more residues within amino acid residues 1-5 and 33-36 of the extracellular domain (ECD) of human CD40 (SEQ ID NO: 133), e.g., amino acids 5, 33, 34 and/or 36 of the ECD of human CD40 (SEQ ID NO: 133). Antibody 3C3 also is shown to further bind to one or more amino acids 26, 28 and/or 30 of the ECD of human CD40 (SEQ ID NO: 133), e.g., amino acids 5, 33, 34 and 36 of the ECD of human CD40 (SEQ ID NO: 133) or amino acids 5, 33 and 36 of the ECD of human CD40 (SEQ ID NO: 133).

Other antibodies of the invention (e.g., antibody 3G5) bind to one or more residues within amino acid residues 13-15 and 33-36 of the ECD of human CD40 (SEQ ID NO: 133), e.g., amino acids 33, 34 and 36 of the ECD of human CD40 (SEQ ID NO: 133).

Antibodies which bind to the epitopes on human CD40 described herein (e.g., the same epitopes as the exemplified antibodies) exhibit therapeutically advantageous properties. For example, as demonstrated in Examples 16 and 20, antibody 3C3 exhibits synergistic agnostic effects with soluble CD40 ligand (sCD40L), as measured by, for example, an increase in the induction of CD95 expression when incubated with Ramos cells, an increase in B cell proliferation when incubated with human B cells, and/or an increase in the induction of IL12p40 expression when incubated with dendritic cells.

Accordingly, antibodies that bind to the same epitope as 3C3 have the ability to synergize with other therapeutic agents, including those which bind to the ligand binding site of human CD40. Representative synergistic effects include, for example, upregulation of immune function (e.g. T cell mediated immune responses as in vaccine therapies), NK activation in cancer therapies), inhibition of cell growth (e.g., in cancer therapy), and/or enhanced processing and presentation of an antigen by APCs (e.g., in vaccine therapy).

As described herein, techniques for determining antibodies that bind to the "same epitope on CD40" with the antibodies described herein include, for example, epitope mapping methods, such as, x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. Methods may also rely on the ability of an antibody of interest to affinity isolate specific short peptides (either in native three dimensional form or in denatured form) from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

II. Molecular Conjugates/Immunotoxins

Figure 18:
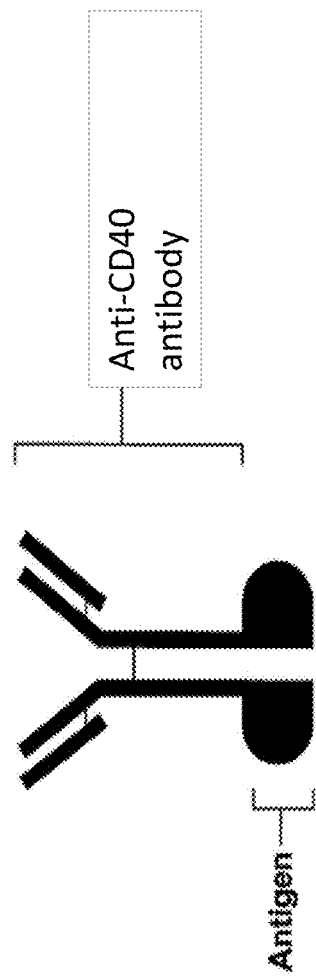
FIG. 18 shows a schematic representation of an example of an anti-CD40/antigen fusion APC targeted vaccine construct.

The present invention provides a variety of therapeutic molecular conjugates (e.g., vaccine conjugates) which include an antigen, such as a tumor or viral antigen, linked to an antibody that binds to a receptor on an APC, for example, an antibody which binds to CD40. This allows for targeting of the antigen to APCs, such as cells expressing CD40 (e.g., dendritic cells, B cells, and macrophages) to enhance processing, presentation and, ultimately, an immune response against the antigen(s). A schematic representation of such a conjugate is shown in FIG. 18 wherein, for example, an antigen is genetically fused to the CH3 domain of each of the heavy chains of a substantially complete anti-CD40 antibody. However, it will be appreciated that the antigen may alternatively be joined to other parts of such an antibody or fragment thereof, and that other forms of conjugation, such as chemical conjugation, may also be employed, as discussed further below.

Suitable antigens for use in the molecular conjugates include, for example, infectious disease antigens and tumor antigens, against which protective or therapeutic immune responses are desired, e.g., antigens expressed by a tumor cell or a pathogenic organism or infectious disease antigens. For example, suitable antigens include tumor-associated antigens for the prevention or treatment of cancers. Examples of tumor-associated antigens include, but are not limited to, sequences comprising all or part of the sequences of βhCG, gp100 or Pmel17, HER2/neu, WT1, mesothelin, CEA, gp100, MART1, TRP-2, melan-A, NY-ESO-1, NY-BR-1, NY-CO-58, MN (gp250), idiotype, MAGE-1, MAGE-3, MAGE-A3, Tyrosinase, Telomerase, SSX2 and MUC-1 antigens, and germ cell derived tumor antigens. Tumor associated antigens also include the blood group antigens, for example, Le$^a$, Le$^b$, LeX, LeY, H-2, B-1, B-2 antigens. Alternatively, more than one antigen can be included within the antigen-antibody constructs of the invention. For example, a MAGE antigen can be combined with other antigens such as melanin A, tyrosinase, and gp100 along with adjuvants such as GM-CSF or IL-12, and linked to an anti-APC antibody.

Other suitable antigens include viral antigens for the prevention or treatment of viral diseases. Examples of viral antigens include, but are not limited to, HIV-1 gag, HIV-1 env, HIV-1 nef, HBV (surface or core antigens), HPV, FAS, HSV-1, HSV-2, p17, ORF2 and ORF3 antigens. Examples of bacterial antigens include, but are not limited to, *Toxoplasma gondii* or *Treponema pallidum*. The antibody-bacterial antigen conjugates of the invention can be in the treatment or prevention of various bacterial diseases such as Anthrax, Botulism, Tetanus, *Chlamydia*, Cholera, Diphtheria, Lyme Disease, Syphilis and Tuberculosis.

Sequences of the above-described antigens are well known in the art. For example, an example of a MAGE-3 cDNA sequence is provided in U.S. Pat. No. 6,235,525 (Ludwig Institute for Cancer Research); examples of NY-ESO-1 nucleic acid and protein sequences are provided in U.S. Pat. Nos. 5,804,381 and 6,069,233 (Ludwig Institute for Cancer Research); examples of Melan-A nucleic acid and protein sequences are provided in U.S. Pat. Nos. 5,620,886 and 5,854,203 (Ludwig Institute for Cancer Research); examples of NY-BR-1 nucleic acid and protein sequences are provided in U.S. Pat. Nos. 6,774,226 and 6,911,529 (Ludwig Institute for Cancer Research) and examples of NY-CO-58 nucleic acid and protein sequences are provided in WO 02090986 (Ludwig Institute for Cancer Research); an example of an amino acid sequence for the HER-2/neu protein is available at GENBANK® Accession No. AAA58637; and a nucleotide sequence (mRNA) for human carcinoembryonic antigen-like 1 (CEA-1) is available at GENBANK® Accession No. NM_020219.

In one embodiment, the antigen is an HPV antigen, for example, HPV-16 antigen, an HPV-18 antigen, an HPV-31 antigen, an HPV-33 antigen and/or HPV-35 antigen. A genome of HPV-16 is described in *Virology*, 145:181-185 (1985) and DNA sequences encoding HPV-18 are described in U.S. Pat. No. 5,840,306, the disclosures of which are incorporated by reference herein in their entirety. HIPV-16 antigens (e.g., seroreactive regions of the E1 and/or E2 proteins of HPV-16) are described in U.S. Pat. No. 6,531,127, and HPV-18 antigens (e.g., seroreactive regions of the L1 and/or L2 proteins of HPV-18) are described in U.S. Pat. No. 5,840,306, the disclosures of which are incorporated by reference herein. Similarly, a complete genome for HBV is available at GENBANK® Accession No. NC_003977, the disclosure of which is incorporated herein. The genome of HCV is described in European Patent Application No. 318 216, the disclosure of which is incorporated herein. PCT/US90/01348, incorporated by reference herein, discloses sequence information of clones of the HCV genome, amino acid sequences of HCV viral proteins and methods of making and using such compositions for HCV vaccines comprising HCV proteins and peptides derived therefrom.

Antigenic peptides of proteins (i.e., those containing T cell epitopes) can be identified in a variety of manners well known in the art. For example, T cell epitopes can be predicted by analyzing the sequence of the protein using web-based predictive algorithms (BIMAS & SYFPEITHI) to generate potential MHC class I and II-binding peptides that match an internal database of 10,000 well characterized MHC binding peptides previously defined by CTLs. High scoring peptides can be ranked and selected as "interesting" on the basis of high affinity to a given MHC molecule.

Another method for identifying antigenic peptides containing T cell epitopes involves dividing the protein into non-overlapping peptides of desired length or overlapping peptides of desired lengths which can be produced recombinantly, synthetically, or in certain limited situations, by chemical cleavage of the protein and tested for immunogenic properties, e.g., eliciting a T cell response (i.e., proliferation or lymphokine secretion).

In order to determine precise T cell epitopes of the protein by, for example, fine mapping techniques, a peptide having T cell stimulating activity and thus comprising at least one T cell epitope, as determined by T cell biology techniques, can be modified by addition or deletion of amino acid residues at either the amino or carboxy terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. Peptides are selected based on various factors, including the strength of the T cell response to the peptide (e.g., stimulation index). The physical and chemical properties of these selected peptides (e.g., solubility, stability) can then be examined to determine whether the peptides are suitable for use in therapeutic compositions or whether the peptides require modification.

In addition, the vaccine conjugate can include one or more immunostimulatory agents that also enhance the immune response against the antigen. Antibody-antigen vaccine conjugates of the invention can be made genetically or chemically. In either case, the antibody portion of the conjugate may consist of the whole antibody or a portion of the antibody, such as the Fab fragment or single-chain Fv. In addition, more than one antigen and/or immunostimulatory agent can be included in the conjugate.

Chemically constructed antibody-antigen conjugates can be made using a variety of well known and readily available cross-linking reagents. These cross-linking reagents can be homofunctional or heterofunctional compounds, such as N-succinimidyl-3-(2-pyridyldithio)propionate (SPDP), N-succinimidyl-S-acetyl-thioacetate (SATA), sulfosuccinimidyl 4-(N-maleimidomethyl) cyclohaxane-1-carboxylate (sulfo-SMCC), 5,5'-dithiobis(2-nitrobenzoic acid) (DTNB), that form covalent linkages with different reactive amino acid or carbohydrate side chains on the anti-dendritic antibody and selected antigen. Other coupling and cross-linking agents also can be used to generate covalent linkages, such as protein A, carbodiimide, and o-phenylenedimaleimide (oPDM); (see e.g., Karpovsky et al. (1984) J. Exp. Med. 160:1686; Liu, M A et al. (1985) Proc. Natl. Acad. Sci. USA 82:8648). Other methods include those described by Paulus (Behring Ins. Mitt. (1985) No. 78, 118-132); Brennan et al. (Science (1985) 229:81-83), and Glennie et al. (J. Immunol. (1987) 139: 2367-2375). Preferred conjugating agents are SATA and sulfo-SMCC, both available from Pierce Chemical Co. (Rockford, Ill.). Immunostimulatory agents can also be chemically linked to the molecular conjugates of the present invention using the same linking methods described above.

In another embodiment, the antibodies of the present invention are linked to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a dendritic-related disorder, such as an autoimmune or inflammatory disease, or graft versus host disease.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

III. Compositions

In another embodiment, the present invention provides a composition, e.g., a composition, containing one or a combination of monoclonal antibodies of the present invention, formulated together with a carrier (e.g., a pharmaceutically acceptable carrier). Compositions containing bispecific molecules which comprise an antibody of the present invention are also provided. In one embodiment, the compositions include a combination of multiple (e.g., two or more) isolated antibodies of the invention. Preferably, each of the antibodies of the composition binds to a distinct, preselected epitope of CD40.

Pharmaceutical compositions of the invention also can be administered in combination therapy, i.e., combined with other agents. For example, the combination therapy can include a composition of the present invention with at least one or more additional therapeutic agents, such as antiinflammatory agents, DMARDs (disease-modifying antirheumatic drugs), immunosuppressive agents, and chemotherapeutics. The pharmaceutical compositions of the invention can also be administered in conjunction with radiation therapy. Co-administration with other antibodies is also encompassed by the invention.

As used herein, the terms "carrier" and "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

Examples of adjuvants which may be used with the antibodies and constructs of the present invention include: Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatised polysaccharides; polyphosphazenes; biodegradable microspheres; cytokines, such as GM-CSF, interleukin-2, -7, -12, and other like factors; 3D-MPL; CpG oligonucleotide; and monophosphoryl lipid A, for example 3-de-O-acylated monophosphoryl lipid A.

MPL adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996.

Further alternative adjuvants include, for example, saponins, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins; Montanide ISA 720 (Seppic, France); SAF (Chiron, Calif., United States); ISCOMS (CSL), MF-59 (Chiron); the SBAS series of adjuvants (e.g., SBAS-2 or SBAS-4, available from SmithKline Beecham, Rixensart, Belgium); Detox (Enhanzyn™) (Corixa, Hamilton, Mont.); RC-529 (Corixa, Hamilton, Mont.) and other aminoalkyl glucosaminide 4-phosphates (AGPs); polyoxyethylene ether adjuvants such as those described in WO 99/52549A1; synthetic imidazoquinolines such as imiquimod [S-26308, R-837], (Harrison, et al., Vaccine 19: 1820-1826, 2001; and resiquimod [S-28463, R-848] (Vasilakos, et al., Cellular immunology 204: 64-74, 2000; Schiff bases of carbonyls and amines that are constitutively expressed on antigen presenting cell and T-cell surfaces, such as tucaresol (Rhodes, J. et al., Nature 377: 71-75, 1995); cytokine, chemokine and co-stimulatory molecules as either protein or peptide, including for example pro-inflammatory cytokines such as Interferon, GM-CSF, IL-1 alpha, IL-1 beta, TGF-alpha and TGF-beta, Th1 inducers such as interferon gamma, IL-2, IL-12, IL-15, IL-18 and IL-21, Th2 inducers such as IL-4, IL-5, IL-6, IL-10 and IL-13 and other chemokine and co-stimulatory genes such as MCP-1, MIP-1 alpha, MIP-1 beta, RANTES, TCA-3, CD80, CD86 and CD70; immunostimulatory agents targeting ligands such as CTLA-4 and L-selectin, apoptosis stimulating proteins and peptides such as Fas; synthetic lipid based adjuvants, such as vaxfectin, (Reyes et al., *Vaccine* 19: 3778-3786, 2001) squalene, alpha-tocopherol, polysorbate 80, DOPC and cholesterol; endotoxin, [LPS], (Beutler, B., Current Opinion in Microbiology 3: 23-30, 2000); ligands that trigger Toll receptors to produce Th1-inducing cytokines, such as synthetic Mycobacterial lipoproteins, Mycobacterial protein p19, peptidoglycan, teichoic acid and lipid A; and CT (cholera toxin, subunits A and B) and LT (heat labile enterotoxin from *E. coli*, subunits A and B), heat shock protein family (HSPs), and LLO (listeriolysin O; WO 01/72329). These and various further Toll-like Receptor (TLR) agonists are described for example in Kanzler et al, *Nature Medicine*, May 2007, Vol 13, No 5. A preferred immunostimulatory agent for use in combination with an anti-CD40 antibody of the invention is a TLR3 agonist, such as Poly IC.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Acceptable diluents include saline and aqueous buffer solutions. Liposomes include water-in-oil-in-water CGF emulsions as well as conventional liposomes (Strejan et al. (1984) *J. Neuroimmunol.* 7:27).

Carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the antibodies of the invention may be administered once or twice weekly by subcutaneous or intramuscular injection or once or twice monthly by subcutaneous or intramuscular injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269: 9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

IV. Uses and Methods of the Invention

Antibodies, molecular conjugates, bispecific molecules, and compositions of the present invention can be used to treat and/or prevent (e.g., immunize against) a variety of diseases and conditions.

One of the primary disease indications is cancer. Types of cancers include, but are not limited to, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system. Particular cancers include CD40-expressing tumors selected from the group consisting of chronic lymphocytic leukemia, mantle cell lymphoma, primary central nervous system lymphoma, Burkitt's lymphoma and marginal zone B cell lymphoma.

Antibodies and conjugates of the invention also can be used to treat bacterial, fungal, viral and parasitic infectious diseases.

When used in therapy, the antibodies of the invention can be administered to a subject directly (i.e., in vivo), either alone or with other therapies such as an immunostimulatory agent, a vaccine, chemotherapy or radiation therapy. In all cases, the antibodies, conjugates, bispecifics, compositions, and immunostimulatory agents and other therapies are administered in an effective amount to exert their desired therapeutic effect. The term "effective amount" refers to that amount necessary or sufficient to realize a desired biologic effect. For example, an effective amount could be that amount necessary to eliminate a tumor, cancer, or bacterial, viral or fungal infection. The effective amount for any particular application can vary depending on such factors as the disease or condition being treated, the particular antibody being administered, the size of the subject, or the severity of the disease or condition. One of ordinary skill in the art can empirically determine the effective amount of a particular molecule without necessitating undue experimentation.

Preferred routes of administration include, for example, injection (e.g., subcutaneous, intravenous, parenteral, intraperitoneal, intrathecal). The injection can be in a bolus or a continuous infusion. Other routes of administration include oral administration.

In another embodiment, the antibody is administered in combination with a vaccine antigen, to enhance the immune response against the vaccine antigen, such as a tumor antigen (to thereby enhance the immune response against the tumor) or an antigen from an infectious disease pathogen (to thereby enhance the immune response against the infectious disease pathogen). The vaccine antigen can be any antigen or antigenic composition capable of eliciting an immune response against a tumor or against an infectious disease pathogen such as a virus, a bacteria, a parasite or a fungus. It may also be, for example, a neoantigen such as those derived from sequencing of patients' tumors. The antigen or antigens can be, for example, peptides/proteins, polysaccharides and/or lipids, or may be administered as nucleic acids (such as DNA) coding for peptide or protein antigens which may be expressed in vivo. The antigen or antigens be derived from tumors, such as the various tumor antigens previously disclosed herein. Alternatively, the antigen or antigens can be derived from pathogens such as viruses, bacteria, parasites and/or fungi, such as the various pathogen antigens previously disclosed herein. Additional examples of suitable pathogen antigens include, but are not limited to, the following:

Viral antigens or antigenic determinants can be derived from, for example: Cytomegalovirus (especially Human, such as gB or derivatives thereof); Epstein Barr virus (such as gp350); flaviviruses (e.g. Yellow Fever Virus, Dengue Virus, Tick-borne encephalitis virus, Japanese Encephalitis Virus); hepatitis virus such as hepatitis B virus (for example Hepatitis B Surface antigen such as the PreS1, PreS2 and S antigens described in EP-A-414 374; EP-A-0304 578, and EP-A-198474), hepatitis A virus, hepatitis C virus and hepatitis E virus; HIV-1, (such as tat, nef, gp120 or gp160); human herpes viruses, such as gD or derivatives thereof or Immediate Early protein such as ICP27 from HSV1 or HSV2; human papilloma viruses (for example HPV6, 11, 16, 18); Influenza virus (whole live or inactivated virus, split influenza virus, grown in eggs or MDCK cells, or Vero cells or whole flu virosomes (as described by Gluck, Vaccine, 1992, 10, 915-920) or purified or recombinant proteins thereof, such as NP, NA, HA, or M proteins); measles virus; mumps virus; parainfluenza virus; rabies virus; Respiratory Syncytial virus (such as F and G proteins); rotavirus (including live attenuated viruses); smallpox virus; Varicella Zoster Virus (such as gpI, II and IE63); and the HPV viruses responsible for cervical cancer (for example the early proteins E6 or E7 in fusion with a protein D carrier to form Protein D-E6 or E7 fusions from HPV 16, or combinations thereof, or combinations of E6 or E7 with L2 (see for example WO 96/26277).

Bacterial antigens or antigenic determinants can be derived from, for example: *Bacillus* spp., including *B. anthracis* (e.g., botulinum toxin); *Bordetella* spp, including *B. pertussis* (for example pertactin, pertussis toxin, filamenteous hemagglutinin, adenylate cyclase, fimbriae); *Borrelia* spp., including *B. burgdorferi* (eg OspA, OspC, DbpA, DbpB), *B. garinii* (eg OspA, OspC, DbpA, DbpB), *B. afzelii* (eg OspA, OspC, DbpA, DbpB), *B. andersonii* (eg OspA, OspC, DbpA, DbpB), *B. hermsii*; *Campylobacter* spp, including *C. jejuni* (for example toxins, adhesins and invasins) and *C. coli*; *Chlamydia* spp., including *C. trachomatis* (eg MOMP, heparin-binding proteins), *C. pneumonie* (eg MOMP, heparin-binding proteins), *C. psittaci*; *Clostridium* spp., including *C. tetani* (such as tetanus toxin), *C. botulinum* (for example botulinum toxin), *C. difficile* (eg *clostridium* toxins A or B); *Corynebacterium* spp., including *C. diphtheriae* (eg diphtheria toxin); *Ehrlichia* spp., including *E. equi* and the agent of the Human Granulocytic Ehrlichiosis; *Rickettsia* spp, including *R. rickettsii*; *Enterococcus* spp., including *E. faecalis, E. faecium*; *Escherichia* spp, including enterotoxic *E. coli* (for example colonization factors, heat-labile toxin or derivatives thereof, or heat-stable toxin), enterohemorragic *E. coli*, enteropathogenic *E. coli* (for example shiga toxin-like toxin); *Haemophilus* spp., including *H. influenzae* type B (eg PRP), non-typable *H. influenzae*, for example OMP26, high molecular weight adhesins, P5, P6, protein D and lipoprotein D, and fimbrin and fimbrin derived peptides (see for example U.S. Pat. No. 5,843,464); *Helicobacter* spp, including *H. pylori* (for example urease, catalase, vacuolating toxin); *Pseudomonas* spp, including *P. aeruginosa*; *Legionella* spp, including *L. pneumophila*; *Leptospira* spp., including *L. interrogans*; *Listeria* spp., including *L. monocytogenes*; *Moraxella* spp, including *M. catarrhalis*, also known as *Branhamella catarrhalis* (for example high and low molecular weight adhesins and invasins); *Morexella Catarrhalis* (including outer membrane vesicles thereof, and OMP106 (see for example WO97/41731)); *Mycobacterium* spp., including *M. tuberculosis* (for example ESAT6, Antigen 85A, -B or -C), *M. bovis, M. leprae, M. avium, M. paratuberculosis, M. smegmatis*; *Neisseria* spp., including *N. gonorrhea* and *N. meningitidis* (for example capsular polysaccharides and conjugates thereof, transferrin-binding proteins, lactoferrin binding proteins, PilC, adhesins); *Neisseria mengitidis* B (including outer membrane vesicles thereof, and NspA (see for example WO 96/29412); *Salmonella* spp, including *S. typhi, S. paratyphi, S. choleraesuis, S. enteritidis*; *Shigella* spp, including *S. sonnei, S. dysenteriae, S. flexnerii*; *Staphylococcus* spp., including *S. aureus, S. epidermidis*; *Streptococcus* spp, including S. pneumonie (eg capsular polysaccharides and conjugates thereof, PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof (see for example WO 90/06951; WO 99/03884); *Treponema* spp., including *T. pallidum* (eg the outer membrane proteins), *T. denticola, T. hyodysenteriae*; *Vibrio* spp, including *V. cholera* (for example cholera toxin); and *Yersinia* spp, including *Y. enterocolitica* (for example a Yop protein), *Y. pestis, Y. pseudotuberculosis*.

Parasitic/fungal antigens or antigenic determinants can be derived from, for example: *Babesia* spp., including *B. microti*; *Candida* spp., including *C. albicans*; *Cryptococcus* spp., including *C. neoformans*; *Entamoeba* spp., including *E. histolytica*; *Giardia* spp., including; *G. lamblia*; *Leshmania* spp., including *L. major*; *Plasmodium. faciparum* (MSP1, AMA1, MSP3, EBA, GLURP, RAP1, RAP2, Sequestrin, PfEMP1, Pf332, LSA1, LSA3, STARP, SALSA, PfEXPI, Pfs25, Pfs28, PFS27/25, Pfs16, Pfs48/45, Pfs230 and their analogues in *Plasmodium* spp.); *Pneumocystis* spp., including *P. carinii*; *Schisostoma* spp., including *S.* mansoni; *Trichomonas* spp., including *T. vaginalis; Toxoplasma* spp., including *T. gondii* (for example SAG2, SAG3, Tg34); *Trypanosoma* spp., including *T. cruzi*.

It will be appreciated that in accordance with this aspect of the present invention, antigens and antigenic determinants can be used in many different forms. For example, antigens or antigenic determinants can be present as isolated proteins or peptides (for example in so-called "subunit vaccines") or, for example, as cell-associated or virus-associated antigens or antigenic determinants (for example in either live or killed pathogen strains). Live pathogens will preferably be attenuated in known manner. Alternatively, antigens or antigenic determinants may be generated in situ in the subject by use of a polynucleotide coding for an antigen or antigenic determinant (as in so-called "DNA vaccination"), although it will be appreciated that the polynucleotides which can be used with this approach are not limited to DNA, and may also include RNA and modified polynucleotides as discussed above.

When used in therapy, molecular conjugates (i.e., vaccine conjugates) of the invention can be administered to a subject directly (i.e., in vivo), either alone or with an immunostimulatory agent. In one aspect, the immunostimulatory agent is linked to the conjugate. Alternatively, the conjugates can be administered to a subject indirectly by first contacting the conjugates (e.g., by culturing or incubating) with APCs, such as dendritic cells, and then administering the cells to the subject (i.e., ex vivo). The contacting and delivering of the conjugates to APCs, such that they are processed and presented by the APCs prior to administration, is also referred to as antigen or cell "loading." Techniques for loading antigens to APCs are well known in the art and include, for example, Gunzer and Grabbe, Crit Rev Immunol 21 (1-3):133-45 (2001) and Steinman, Exp Hematol 24(8): 859-62 (1996).

In all cases, the vaccine conjugates and the immunostimulatory agents are administered in an effective amount to exert their desired therapeutic effect.

Antibodies, molecular conjugates, bispecific molecules, and compositions of the invention also can be coadministered with adjuvants and other therapeutic agents. It will be appreciated that the term "coadministered" as used herein includes any or all of simultaneous, separate, or sequential administration of the antibodies and conjugates of the present invention with adjuvants and other agents, including administration as part of a dosing regimen. The antibodies are typically formulated in a carrier alone or in combination with such agents. Examples of such carriers include solutions, solvents, dispersion media, delay agents, emulsions and the like. The use of such media for pharmaceutically active substances is well known in the art. Any other conventional carrier suitable for use with the molecules falls within the scope of the instant invention.

Suitable agents for co-administration with the antibodies, conjugates, bispecifics, and compositions include other antibodies, cytotoxins and/or drugs, as well as adjuvants, immunostimulatory agents and/or immunosuppressive agents. In one embodiment, the agent is a chemotherapeutic agent. The antibodies, bispecifics, and compositions can be administered in combination with radiation.

Chemotherapeutic agents suitable for coadministration with the antibodies and conjugates of the present invention in the treatment of tumors include, for example: taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine) and temozolomide.

Agents that delete or inhibit immunosuppressive activities, for example, by immune cells (for example regulatory T-cells, NKT cells, macrophages, myeloid-derived suppressor cells, immature or suppressive dendritic cells) or suppressive factors produced by the tumor or host cells in the local microenvironment of the tumor (for example, TGF-beta, indoleamine 2,3 dioxygenase—IDO), may also be administered with the antibodies and conjugates of the present invention. Such agents include antibodies and small molecule drugs such as IDO inhibitors such as 1 methyl tryptophan or derivatives.

Suitable agents for coadministration with the antibodies, conjugates, and bispecifics of the present invention for inducement or enhancement of an immune response include, for example, adjuvants and/or immunostimulatory agents, non-limiting examples of which have been disclosed hereinbefore. A preferred immunostimulatory agent is a TLR3 agonist, such as Poly IC.

V. Combination Therapies

The anti-CD40 antibodies described herein also can be used in combination therapy, e.g., for treating cancer. Accordingly, provided herein are methods of combination therapy in which an anti-CD40 antibody is co-administered with one or more additional agents, e.g., small molecule drugs, antibodies or antigen binding portions thereof, and/or protein ligands that are effective in stimulating immune responses to thereby further enhance, stimulate or upregulate immune responses in a subject. Moreover, as shown in the Examples herein, administration of an agonist anti-CD40 antibody and soluble CD40 ligand had a synergic effect in inducing T cell receptor-mediated signals, e.g., as shown by the increase in the expression of CD95 in tumor cells.

For example, an anti-CD40 antibody, e.g., described herein, can be combined with (i) an agonist of a stimulatory (e.g., co-stimulatory) molecule (e.g., receptor or ligand) and/or (ii) an antagonist of an inhibitory signal or molecule (e.g., receptor or ligand) on immune cells, such as T cells, both of which result in amplifying immune responses, such as antigen-specific T cell responses. In certain aspects, an immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on cells involved in innate immunity, e.g., NK cells, and wherein the immuno-oncology agent enhances innate immunity. Such immuno-oncology agents are often referred to as immune checkpoint regulators, e.g., immune checkpoint inhibitor or immune checkpoint stimulator.

In one embodiment, an anti-CD40 antibody is administered with an agent that targets a stimulatory or inhibitory molecule that is a member of the immunoglobulin super family (IgSF). For example, anti-CD40 antibodies, e.g., described herein, may be administered to a subject with an agent that targets a member of the IgSF family to increase an immune response. For example, an anti-CD40 antibody may be administered with an agent that targets (or binds specifically to) a member of the B7 family of membrane-bound ligands that includes B7-1, B7-2, B7-H1 (PD-L1), B7-DC (PD-L2), B7-H2 (ICOS-L), B7-H3, B7-H4, B7-H5 (VISTA), and B7-H6 or a co-stimulatory or co-inhibitory receptor binding specifically to a B7 family member.

An anti-CD40 antibody may also be administered with an agent that targets a member of the TNF and TNFR family of molecules (ligands or receptors), such as CD40 and CD40L (e.g., human CD40 and human CD40L), OX-40, OX-40L, CD70, CD27L, CD30, CD30L, 4-1BBL, CD137, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDA1, EDA2, TNFR1, Lymphotoxin α/TNFβ, TNFR2, TNFα, LTOR, Lymphotoxin α1β2, FAS, FASL, RELT, DR6, TROY, and NGFR (see, e.g., Tansey (2009) Drug Discovery Today 00:1).

T cell responses can be stimulated by a combination of anti-CD40 antibodies described herein, e.g., 3C3 and 3G5, and one or more of an antagonist (inhibitor or blocking agent) of a protein that inhibits T cell activation (e.g., immune checkpoint inhibitors), such as CTLA-4, PD-1, PD-L1, PD-L2, and LAG-3, as described above, and any of the following proteins: TIM-3, Galectin 9, CEACAM-1, BTLA, CD69, Galectin-1, TIGIT, CD113, GPR56, VISTA, B7-H3, B7-H4, 2B4, CD48, GARP, PD1H, LAIR1, TIM-1, and TIM4-4, and/or one or more of an agonist of a protein that stimulates T cell activation, such as B7-1, B7-2, CD28, 4-1BB (CD137), 4-1BBL, ICOS, ICOS-L, OX40, OX40L, CD70, CD27, CD40, DR3 and CD28H.

Exemplary agents that modulate one of the above proteins and may be combined with agonist anti-CD40 antibodies, e.g., those described herein, for treating cancer, include: Yervoy™ (ipilimumab) or Tremelimumab (to CTLA-4), galiximab (to B7.1), BMS-936558/nivolumab (to PD-1), MK-3475/pembrolizumab (to PD-1), AMP224 (to B7DC), BMS-936559 (to B7-H1), MPDL3280A/atezolizumab (to B7-H1), MEDI-570 (to ICOS), AMG557 (to B7H2), MGA271 (to B7H3), MP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4).

Other molecules that can be combined with agonist anti-CD40 antibodies for the treatment of cancer include antagonists of inhibitory receptors on NK cells or agonists of activating receptors on NK cells. For example, anti-CD40 agonist antibodies can be combined with antagonists of KIR (e.g., lirilumab).

T cell activation is also regulated by soluble cytokines, and anti-CD40 antibodies may be administered to a subject, e.g., having cancer, with antagonists of cytokines that inhibit T cell activation or agonists of cytokines that stimulate T cell activation.

In another embodiment, anti-CD40 antibodies can be used in combination with (i) antagonists (or inhibitors or blocking agents) of proteins of the IgSF family or B7 family or the TNF family that inhibit T cell activation or antagonists of cytokines that inhibit T cell activation (e.g., IL-6, IL-10, TGF-β, VEGF; "immunosuppressive cytokines") and/or (ii) agonists of stimulatory receptors of the IgSF family, B7 family or the TNF family or of cytokines that stimulate T cell activation, for stimulating an immune response, e.g., for treating proliferative diseases, such as cancer.

Other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

Anti-CD40 antibodies may also be administered with agents that inhibit TGF-β signaling.

Additional agents that may be combined with an anti-CD40 antibody include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Other therapies that may be combined with an anti-CD40 antibody include therapies that deplete or block Treg cells, e.g., an agent that specifically binds to CD25.

Another therapy that may be combined with an anti-CD40 antibody is a therapy that inhibits a metabolic enzyme such as indoleamine dioxygenase (IDO), dioxigenase, arginase, or nitric oxide synthetase.

Another class of agents that may be used with an anti-CD40 antibody includes agents that inhibit the formation of adenosine or inhibit the adenosine A2A receptor.

Other therapies that may be combined with an anti-CD40 antibody for treating cancer include therapies that reverse/prevent T cell anergy or exhaustion and therapies that trigger an innate immune activation and/or inflammation at a tumor site.

An anti-CD40 antibody may be combined with more than one immuno-oncology agent, and may be, e.g., combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells; a therapy that stimulates positive immune regulation, e.g., with agonists that stimulate the CD-137, OX-40, and/or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxygenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immuno repressive cytokines.

Agonist anti-CD40 antibodies described herein can be used together with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

Provided herein are methods for stimulating an immune response in a subject comprising administering to the subject an agonist anti-CD40 molecule, e.g., an antibody, and one or more additional immunostimulatory antibodies, such as an anti-PD-1 antagonist, e.g., antagonist antibody, an anti-PD-L1 antagonist, e.g., antagonist antibody, an antagonist anti-CTLA-4 antagonist, e.g., antagonist antibody and/or an anti-LAG3 antagonist, e.g., an antagonist antibody, such that an immune response is stimulated in the subject, for example to inhibit tumor growth or to stimulate an anti-viral response. In one embodiment, the additional immunostimulatory antibody (e.g., an antagonist anti-PD-1, an antagonist anti-PD-L1, an antagonist anti-CTLA-4 and/or an antagonist anti-LAG3 antibody) is a human antibody.

Also provided herein are methods for treating a hyperproliferative disease (e.g., cancer), comprising administering an agonist anti-CD40 antibody and an antagonist PD-1 antibody to a subject. In one embodiment, the subject is human. In another embodiment, the anti-PD-1 antibody is a human sequence monoclonal antibody and the anti-CD40 antibody is human sequence monoclonal antibody, such as an antibody comprising the CDRs or variable regions of 3C3 and 3G5 described herein or another agonist anti-CD40 antibody described herein.

Suitable PD-1 antagonists for use in the methods described herein, include, without limitation, ligands, antibodies (e.g., monoclonal antibodies and bispecific antibodies), and multivalent agents. In one embodiment, the PD-1 antagonist is a fusion protein, e.g., an Fc fusion protein, such as AMP-244. In one embodiment, the PD-1 antagonist is an anti-PD-1 or anti-PD-L1 antibody.

An exemplary anti-PD-1 antibody is nivolumab (BMS-936558) or an antibody that comprises the CDRs or variable regions of one of antibodies 17D8, 2D3, 4H1, 5C4, 7D3, 5F4 and 4A11 described in WO 2006/121168. In certain embodiments, an anti-PD1 antibody is MK-3475 (Lambrolizumab) described in WO2012/145493; and AMP-514 described in WO 2012/145493. Further known PD-1 antibodies and other PD-1 inhibitors include those described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368. Any of the anti-PD-1 antibodies disclosed in WO2013/173223 may also be used. An anti-PD-1 antibody that competes for binding with, and/or binds to the same epitope on PD-1 as, as one of these antibodies may also be used in combination treatments. Another approach to target the PD-1 receptor is the recombinant protein composed of the extracellular domain of PD-L2 (B7-DC) fused to the Fc portion of IgG1, called AMP-224.

Provided herein are methods for treating a hyperproliferative disease (e.g., cancer), comprising administering an agonist anti-CD40 antibody and an antagonist PD-L1 antibody to a subject. In one embodiment, the subject is human. In another embodiment, the anti-PD-L1 antibody is a human sequence monoclonal antibody and the anti-CD40 antibody is human sequence monoclonal antibody, such as an antibody comprising the CDRs or variable regions of 3C3 and 3G5 described herein or another agonist anti-CD40 antibody described herein.

In one embodiment, the anti-PD-L1 antibody is BMS-936559 (referred to as 12A4 in WO 2007/005874 and U.S. Pat. No. 7,943,743), or an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943, 743. In certain embodiment an anti-PD-L1 antibody is MEDI4736 (also known as Anti-B7-H1), MPDL3280A (also known as RG7446), MSB0010718C (WO2013/79174), or rHigM12B7. Any of the anti-PD-L1 antibodies disclosed in W2013/173223, WO2011/066389, WO2012/145493, U.S. Pat. Nos. 7,635,757 and 8,217,149 and U.S. Publication No. 2009/145493 may also be used. Anti-PD-L1 antibodies that compete with and/or bind to the same epitope as that of any of these antibodies may also be used in combination treatments.

Provided herein are methods for treating a hyperproliferative disease (e.g., cancer), comprising administering an anti-CD40 antibody described herein and a CTLA-4 antagonist antibody to a subject. In one embodiment, the subject is human. In another embodiment, the anti-CTLA-4 antibody is an antibody selected from the group of. Yervoy™ (ipilimumab or antibody 10D1, described in PCT Publication WO 01/14424), tremelimumab (formerly ticilimumab, CP-675,206), monoclonal or an anti-CTLA-4 antibody described in any of the following publications: WO 98/42752; WO 00/37504; U.S. Pat. No. 6,207,156; Hurwitz et al. (1998) Proc. Natl. Acad. Sci. USA 95(17):10067-10071; Camacho et al. (2004) J. Cin. Oncology 22(145): Abstract No. 2505 (antibody CP-675206); and Mokyr et al. (1998) Cancer Res. 58:5301-5304. Any of the anti-CTLA-4 antibodies disclosed in WO2013/173223 may also be used.

Provided herein are methods for treating a hyperproliferative disease (e.g., cancer), comprising administering an anti-CD40 antibody and an anti-LAG-3 antibody to a subject. In one embodiment, the subject is human. In another embodiment, the anti-PD-L1 antibody is a human sequence monoclonal antibody and the anti-CD40 antibody is human sequence monoclonal antibody, such as an antibody comprising the CDRs or variable regions of 3C3 or 3G5 described herein or another agonist anti-CD40 antibody described herein. Examples of anti-LAG3 antibodies include antibodies comprising the CDRs or variable regions of antibodies 25F7, 26H10, 25E3, 8B7, 11F2 or 17E5, which are described in U.S. Patent Publication No. US2011/0150892, WO10/19570 and WO2014/008218. In one embodiment, an anti-LAG-3 antibody is BMS-986016. Other art recognized anti-LAG-3 antibodies that can be used include IMP731 and IMP-321, described in US 2011/007023, WO08/132601, and WO09/44273. Anti-LAG-3 antibodies that compete with and/or bind to the same epitope as that of any of these antibodies may also be used in combination treatments.

Administration of anti-CD40 antibodies described herein and antagonists, e.g., antagonist antibodies, to one or more second target antigens such as LAG-3 and/or CTLA-4 and/or PD-1 and/or PD-L1 can enhance the immune response to cancerous cells in the patient. Cancers whose growth may be inhibited using the antibodies of the instant disclosure include cancers typically responsive to immunotherapy and those that are not typically responsive to immunotherapy. Representative examples of cancers for treatment with the combination therapy of the instant disclosure include those cancers listed herein.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. For example, an anti-CTLA-4 antibody and an anti-CD40 antibody can be administered sequentially, such as anti-CTLA-4 antibody being administered first and anti-CD40 antibody second, or anti-CD40 antibody being administered first and anti-CTLA-4 antibody second. Additionally or alternatively, an anti-PD-1 antibody and an anti-CD40 antibody can be administered sequentially, such as anti-PD-1 antibody being administered first and anti-CD40 antibody second, or anti-CD40 antibody being administered first and anti-PD-1 antibody second. Additionally or alternatively, an anti-PD-L1 antibody and an anti-CD40 antibody can be administered sequentially, such as anti-PD-L1 antibody being administered first and anti-CD40 antibody second, or anti-CD40 antibody being administered first and anti-PD-L1 antibody second. Additionally or alternatively, an anti-LAG-3 antibody and an anti-CD40 antibody can be administered sequentially, such as anti-LAG-3 antibody being administered first and anti-CD40 antibody second, or anti-CD40 antibody being administered first and anti-LAG-3 antibody second.

Furthermore, if more than one dose of the combination therapy is administered sequentially, the order of the sequential administration can be reversed or kept in the same order at each time point of administration, sequential administrations can be combined with concurrent administrations, or any combination thereof. For example, the first administration of a combination anti-CTLA-4 antibody and anti-CD40 antibody can be concurrent, the second administration can be sequential with anti-CTLA-4 antibody first and anti-CD40 antibody second, and the third administration can be sequential with anti-CD40 antibody first and anti-CTLA-4 antibody second, etc. Additionally or alternatively, the first administration of a combination anti-PD-1 antibody and anti-CD40 antibody can be concurrent, the second administration can be sequential with anti-PD-1 antibody first and anti-CD40 antibody second, and the third administration can be sequential with anti-CD40 antibody first and anti-PD-1 antibody second, etc. Additionally or alternatively, the first administration of a combination anti-PD-L1 antibody and anti-CD40 antibody can be concurrent, the second administration can be sequential with anti-PD-L1 antibody first and anti-CD40 antibody second, and the third administration can be sequential with anti-CD40 antibody first and anti-PD-L1 antibody second, etc. Additionally or alternatively, the first administration of a combination anti-LAG-3 antibody and anti-CD40 antibody can be concurrent, the second administration can be sequential with anti-LAG-3 antibody first and anti-CD40 antibody second, and the third administration can be sequential with anti-CD40 antibody first and anti-LAG-3 antibody second, etc. Another representative dosing scheme can involve a first administration that is sequential with anti-CD40 first and anti-CTLA-4 antibody (and/or anti-PD-1 antibody and/or anti-PD-L1 antibody and/or anti-LAG-3 antibody) second, and subsequent administrations may be concurrent.

In one embodiment, a subject having a disease that may benefit from stimulation of the immune system, e.g., cancer or an infectious disease, is treated by administration to the subject of an anti-CD40 antibody and an immuno-oncology agent, wherein the immuno-oncology agent is a CD137 (4-1BB) agonist, such as an agonistic CD137 antibody. Suitable CD137 antibodies include, for example, urelumab or PF-05082566 (WO12/32433).

In one embodiment, a subject having a disease that may benefit from stimulation of the immune system, e.g., cancer or an infectious disease, is treated by administration to the subject of an anti-CD40 antibody and an immuno-oncology agent, wherein the immuno-oncology agent is an OX40 agonist, such as an agonistic OX40 antibody. Suitable OX40 antibodies include, for example, MEDI-6383, MEDI-6469 or MOXR0916 (RG7888; WO06/029879).

In one embodiment, a subject having a disease that may benefit from stimulation of the immune system, e.g., cancer or an infectious disease, is treated by administration to the subject of an anti-CD40 antibody and an immuno-oncology agent, wherein the immuno-oncology agent is a second CD40 agonist, such as another agonistic CD40 antibody.

In one embodiment, a subject having a disease that may benefit from stimulation of the immune system, e.g., cancer or an infectious disease, is treated by administration to the subject of an anti-CD40 antibody and an immuno-oncology agent, wherein the immuno-oncology agent is a CD27 agonist, such as an agonistic CD27 antibody. Suitable CD27 antibodies include, for example, varlilumab (CDX-1127).

In one embodiment, a subject having a disease that may benefit from stimulation of the immune system, e.g., cancer or an infectious disease, is treated by administration to the subject of an anti-CD40 antibody and an immuno-oncology agent, wherein the immuno-oncology agent is MGA271 (to B7H3) (WO11/109400).

In one embodiment, a subject having a disease that may benefit from stimulation of the immune system, e.g., cancer or an infectious disease, is treated by administration to the subject of an anti-CD40 antibody and an immuno-oncology agent, wherein the immuno-oncology agent is a KIR antagonist, such as lirilumab.

In one embodiment, a subject having a disease that may benefit from stimulation of the immune system, e.g., cancer or an infectious disease, is treated by administration to the subject of an anti-CD40 antibody and an immuno-oncology agent, wherein the immuno-oncology agent is an IDO antagonist. Suitable IDO antagonists include, for example, INCB-024360 (WO2006/122150, WO07/75598, WO08/36653, WO08/36642), indoximod, NLG-919 (WO09/73620, WO09/1156652, WO11/56652, WO12/142237) or F001287.

In one embodiment, a subject having a disease that may benefit from stimulation of the immune system, e.g., cancer or an infectious disease, is treated by administration to the subject of an anti-CD40 antibody and an immuno-oncology agent, wherein the immuno-oncology agent is a Toll-like receptor agonist, e.g., a TLR2/4 agonist (e.g., *Bacillus* Calmette-Guerin); a TLR7 agonist (e.g., Hiltonol or Imiquimod); a TLR7/8 agonist (e.g., Resiquimod); or a TLR9 agonist (e.g., CpG7909).

In one embodiment, a subject having a disease that may benefit from stimulation of the immune system, e.g., cancer or an infectious disease, is treated by administration to the subject of an anti-CD40 antibody and an immuno-oncology agent, wherein, the immuno-oncology agent is a TGF-β inhibitor, e.g., GC1008, LY2157299, TEW7197, or IMC-TR1.

In one aspect, an anti-CD40 antibody is sequentially administered prior to administration of a second agent, e.g., an immuno-oncology agent. In one aspect, an anti-CD40 antibody is administered concurrently with the second agent, e.g., an immunology-oncology agent. In yet one aspect, an anti-CD40 antibody is sequentially administered after administration of the second agent. The administration of the two agents may start at times that are, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks apart, or administration of the second agent may start, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks after the first agent has been administered.

In certain aspects, an anti-CD40 antibody and a second agent, e.g., an immuno-oncology agent, are administered simultaneously, e.g., are infused simultaneously, e.g., over a period of 30 or 60 minutes, to a patient. Alternatively, the anti-CD40 antibody may be co-formulated with a second agent, e.g., an immuno-oncology agent.

Optionally, the anti-CD40 is administered as the sole immunotherapeutic agent, or a combination of the anti-CD40 antibody and one or more additional immunotherapeutic antibodies (e.g., anti-CTLA-4 and/or anti-PD-1 and/or anti-PD-L1 and/or anti-LAG-3 antibody) can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below). The anti-CD40 antibody and one or more additional antibodies (e.g., anti-CTLA-4 and/or anti-PD-1 and/or anti-PD-L1 and/or anti-LAG-3 antibodies) can also be further combined with standard cancer treatments. For example, the anti-CD40 antibody and one or more additional antibodies (e.g., anti-CTLA-4 and/or anti-PD-1 and/or anti-PD-L1 and/or anti-LAG-3 antibodies) can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304). An example of such a combination is a combination of anti-CD40 agonist antibody (with or without and an additional antibody, such as anti-CTLA-4 antibodies and/or anti-PD-1 antibodies and/or anti-PD-L1 antibodies and/or anti-LAG-3 antibodies) in combination with decarbazine for the treatment of melanoma. Another example is a combination of anti-CD40 antibody (with or without anti-CTLA-4 antibodies and/or anti-PD-1 antibodies and/or anti-PD-L1 antibodies and/or LAG-3 antibodies) in combination with interleukin-2 (IL-2) for the treatment of melanoma. The scientific rationale behind the combined use of an anti-CD40 antibody and anti-CTLA-4 and/or anti-PD-1 and/or anti-PD-L1 and/or anti-LAG-3 antibodies with chemotherapy is that cell death, which is a consequence of the cytotoxic action of most chemotherapeutic compounds, should result in increased levels of tumor antigen in the antigen presentation pathway. Other combination therapies that may result in synergy with an anti-CD40 antibody (with or without an anti-CTLA-4 and/or anti-PD-1 and/or anti-PD-L1 and/or anti-LAG-3 antibody) include radiation, surgery, or hormone deprivation. Each of these protocols creates a source of tumor antigen in the host. Angiogenesis inhibitors can also be combined with a combined an anti-CD40 antibody and an anti-CTLA-4 antibody and/or anti-PD-1 antibody and/or anti-PD-L1 antibody and/or anti-LAG-3 antibody. Inhibition of angiogenesis leads to tumor cell death, which can be a source of tumor antigen fed into host antigen presentation pathways.

An anti-CD40 agonist antibody as sole immunotherapeutic agent, or a combination of CD40 agonistic and CTLA-4 and/or PD-1 and/or PD-L1 and/or LAG-3 blocking antibodies also can be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. The T cell arm of these responses would be augmented by the use of a combined anti-CD40 antibody and anti-CTLA-4 antibody and/or anti-PD-1 antibody and/or anti-PD-L1 antibody and/or anti-LAG-3 antibody.

In another example, an anti-CD40 agonist antibody as the sole immunotherapeutic agent or a combination of an anti-CD40 antibody and additional immunostimulating agent, e.g., anti-CTLA-4 antibody and/or anti-PD-1 antibody and/or anti-PD-L1 antibody and/or LAG-3 agent, e.g., antibody, can be used in conjunction with an anti-neoplastic antibody, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by the immunostimulating agent, e.g., CD40, CTLA-4, PD-1, PD-L1 or LAG-3 agent, e.g., antibody. In an exemplary embodiment, a treatment of a hyperproliferative disease (e.g., a cancer tumor) can include an anti-cancer agent, e.g., antibody, in combination with anti-CD40 and optionally an additional immunostimulating agent, e.g., anti-CTLA-4 and/or anti-PD-1 and/or anti-PD-L1 and/or anti-LAG-3 agent, e.g., antibody, concurrently or sequentially or any combination thereof, which can potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be further combined with an anti-CD40 antibody with or without an additional immunostimulating agent, e.g., an anti-CTLA-4 and/or anti-PD-1 and/or anti-PD-L1 and/or anti-LAG-3 agent, such as antibody, to counteract the effects of immunosuppressive agents and favor anti-tumor immune responses by the host.

Other agents, e.g., antibodies, that can be used to activate host immune responsiveness can be further used in combination with an anti-CD40 antibody with or without an additional immunostimulating agent, such as anti-CTLA-4 and/or anti-PD-1 and/or anti-PD-L1 and/or anti-LAG-3 antibody. These include molecules on the surface of dendritic cells that activate DC function and antigen presentation. Anti-CD40 antibodies (Ridge et al., supra) can be used in conjunction with an anti-CD40 antibody and optionally an additional immunostimulating agent, e.g., an anti-CTLA-4 and/or anti-PD-1 and/or anti-PD-L1 and/or anti-LAG-3 agent, e.g., antibody. Other activating antibodies to T cell costimulatory molecules Weinberg et al., supra, Melero et al. supra, Hutloff et al., supra, may also provide for increased levels of T cell activation.

As discussed above, bone marrow transplantation is currently being used to treat a variety of tumors of hematopoietic origin. Anti-CD40 immunotherapy alone or combined with an anti-CTLA-4 antibody and/or anti-PD-1 antibody and/or anti-PD-L1 antibody and/or anti-LAG-3 antibody can be used to increase the effectiveness of the donor engrafted tumor specific T cells.

Several experimental treatment protocols involve ex vivo activation and expansion of antigen specific T cells and adoptive transfer of these cells into recipients in order to antigen-specific T cells against tumor (Greenberg & Riddell, supra). These methods can also be used to activate T cell responses to infectious agents such as CMV. Ex vivo activation in the presence of anti-CD40 with or without an additional immunostimulating therapy, e.g., anti-CTLA-4 and/or anti-PD-1 and/or anti-PD-L1 and/or anti-LAG-3 antibodies can be expected to increase the frequency and activity of the adoptively transferred T cells.

Provided herein are methods for altering an adverse event associated with treatment of a hyperproliferative disease (e.g., cancer) with an immunostimulatory agent, comprising administering an anti-CD40 antibody with or without anti-CTLA-4 and/or anti-PD-1 and/or anti-PD-L1 and/or anti-LAG-3 agent, e.g., antibody, to a subject. For example, the methods described herein provide for a method of reducing the incidence of immunostimulatory therapeutic antibody-induced colitis or diarrhea by administering a non-absorbable steroid to the patient. As used herein, a "non-absorbable steroid" is a glucocorticoid that exhibits extensive first pass metabolism such that, following metabolism in the liver, the bioavailability of the steroid is low, i.e., less than about 20%. In one embodiment described herein, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. The usual oral dosage of ENTOCORT EC® for the treatment of Crohn's disease is 6 to 9 mg/day. ENTOCORT EC® is released in the intestines before being absorbed and retained in the gut mucosa. Once it passes through the gut mucosa target tissue, ENTOCORT EC® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC® can result in systemic glucocorticoid effects such as hypercorticism and adrenal suppression. See PDR 58$^{th}$ ed. 2004; 608-610.

In still further embodiments, the anti-CD40 antibody, with or without immunostimulatory therapeutic antibodies anti-CD40 and optionally anti-CTLA-4 and/or anti-PD-1 and/or anti-PD-L1 and/or anti-LAG-3 antibodies, in conjunction with a non-absorbable steroid can be further combined with a salicylate. Salicylates include 5-ASA agents such as, for example: sulfasalazine (AZULFIDINE®, Pharmacia & UpJohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

In accordance with the methods described herein, a salicylate is administered in combination with anti-CD40, with or without anti-CTLA-4 and/or anti-PD-1 and/or anti-PD-L1 and/or LAG-3 antibodies, and a non-absorbable steroid for the purpose of decreasing the incidence of colitis induced by the immunostimulatory antibodies. Thus, for example, methods for reducing the incidence of colitis induced by the immunostimulatory antibodies described herein encompass administering a salicylate and a non-absorbable concurrently or sequentially (e.g., a salicylate is administered 6 hours after a non-absorbable steroid), or any combination thereof. Further, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-CD40 and anti-CTLA-4 and/or anti-PD-1 and/or anti-PD-L1 and/or anti-LAG-3 antibodies.

The anti-CD40 antibodies and combination antibody therapies described herein may also be used in conjunction with other well known therapies that are selected for their particular usefulness against the indication being treated (e.g., cancer). Combinations of the anti-CD40 antibodies described herein may be used sequentially with known pharmaceutically acceptable agent(s).

For example, the anti-CD40 antibodies and combination antibody therapies described herein can be used in combination (e.g., simultaneously or separately) with an additional treatment, such as irradiation, chemotherapy (e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxorubicin, 5-fu, or camptothecin+apo2/TRAIL (a 6× combo)), one or more proteasome inhibitors (e.g., bortezomib or MG132), one or more Bcl-2 inhibitors (e.g., BH3I-2' (bcl-xl inhibitor), indoleamine dioxygenase-1 inhibitor (e.g., INCB24360, indoximod, NLG-919, or F001287), AT-101 (R-(−)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., Nat Med 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., Avastin), synthetic triterpenoids (see Hyer et al., Cancer Research 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), Trastuzumab, Cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK3β inhibitors, IAP inhibitors and/or genotoxic drugs.

The anti-CD40 antibodies and combination antibody therapies described herein can further be used in combination with one or more anti-proliferative cytotoxic agents. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN™) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Suitable anti-proliferative agents for combining with agonist anti-CD40 antibodies, without limitation, taxanes, paclitaxel (paclitaxel is commercially available as TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment with anti-CD40 antibodies described herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEXM, can also be administered to the patient. When employing the methods or compositions described herein, other agents used in the modulation of tumor growth or metastasis in a clinical setting, such as antimimetics, can also be administered as desired.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

VI. Outcomes

As shown in the Examples herein, co-administration of an anti-CD40 antibody with one or more additional therapeutic agents (e.g., soluble CD40 ligand or another antibody, such as an anti-PD-1 antibody, an anti-PD-L1 antibody, an anti-CTLA-4 antibody, and/or an anti-LAG-3 antibody) provides improved efficacy compared to treatment with the antibody alone or with the one or more additional therapeutic agents in the absence of antibody therapy. Preferably, a combination of an anti-CD40 antibody with one or more additional therapeutic agents exhibits therapeutic synergy.

"Therapeutic synergy" refers to a phenomenon where treatment of patients with a combination of therapeutic agents manifests a therapeutically superior outcome to the outcome achieved by each individual constituent of the combination used at its optimum dose (T. H. Corbett et al., 1982, Cancer Treatment Reports, 66, 1187). In this context a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components. In xenograft models, a combination, used at its maximum tolerated dose, in which each of the constituents will be present at a dose generally not exceeding its individual maximum tolerated dose, manifests therapeutic synergy when, for example, a decrease in tumor growth is achieved by administration of the combination which is greater than the value of the decrease in tumor growth of the best constituent when the constituent is administered alone.

Thus, in combination, the components of such combinations have an additive or superadditive effect on suppressing tumor growth, as compared to monotherapy with the anti-CD40 antibody or treatment with the additional therapeutic agent(s) in the absence of antibody therapy. By "additive" is meant a result that is greater in extent (e.g., in the degree of reduction of tumor mitotic index or of tumor growth or in the degree of tumor shrinkage or the frequency and/or duration of symptom-free or symptom-reduced periods) than the best separate result achieved by monotherapy with each individual component, while "superadditive" is used to indicate a result that exceeds in extent the sum of such separate results. In one embodiment, the additive effect is measured as slowing or stopping of tumor growth. The additive effect can also be measured as, e.g., reduction in size of a tumor, reduction of tumor mitotic index, reduction in number of metastatic lesions over time, increase in overall response rate, or increase in median or overall survival. In another embodiment, the additive effect is measured as increasing induction of CD95 expression when incubated with Ramos cells, increasing B cell proliferation when incubated with human B cells, and/or increasing increased induction of IL12p40 expression when incubated with dendritic cells.

One non-limiting example of a measure by which effectiveness of a therapeutic treatment can be quantified is by calculating the log 10 cell kill, which is determined according to the following equation:

$$\text{log 10 cell kill} = TC(\text{days})/3.32 \times Td$$

in which T C represents the delay in growth of the cells, which is the average time, in days, for the tumors of the treated group (T) and the tumors of the control group (C) to have reached a predetermined value (1 g, or 10 mL, for example), and Td represents the time, in days necessary for the volume of the tumor to double in the control animals. When applying this measure, a product is considered to be active if log 10 cell kill is greater than or equal to 0.7 and a product is considered to be very active if log 10 cell kill is greater than 2.8. Using this measure, a combination, used at its own maximum tolerated dose, in which each of the constituents is present at a dose generally less than or equal to its maximum tolerated dose, exhibits therapeutic synergy when the log 10 cell kill is greater than the value of the log 10 cell kill of the best constituent when it is administered alone. In an exemplary case, the log 10 cell kill of the combination exceeds the value of the log 10 cell kill of the best constituent of the combination by at least 0.1 log cell kill, at least 0.5 log cell kill, or at least 1.0 log cell kill.

The present invention is further illustrated by the following examples which should not be construed as further limiting. The contents of Sequence Listing, figures and all references, patents and published patent applications cited throughout this application are expressly incorporated herein by reference.

EXAMPLES

Example 1

Generation of CD40-Specific Human Monoclonal Antibodies

Human anti-CD40 monoclonal antibodies were generated by immunizing the H2L2 strain of Harbour® transgenic mice with a soluble human CD40 antigen. Harbour® transgenic mice have had the endogenous mouse heavy chain (HC) and kappa light chain (Y-chain) DNA sequences knocked out and have had sequences for the human variable (V) regions and rat constant (C) regions stably incorporated into the mouse genome.

Antigen and Immunization: The antigen was a soluble fusion protein comprising a CD40 extracellular domain fused with an antibody Fc domain (R&D Systems®), or a recombinant human CD40-msG2a chimeric protein (made in-house). The antigen was mixed with Complete Freund's (Sigma) adjuvant for the first immunization. Thereafter, the antigen was mixed with Incomplete Freund's (Sigma). Additional mice were immunized with the soluble CD40 protein in MPL plus TDM adjuvant system (Sigma®). 5-micrograms soluble recombinant CD40 antigen in PBS or $5\times10^6$ NSO cells transfected for surface expression of human CD40 in PBS were mixed 1:1 with the adjuvant. Mice were injected with 200 microliters of the prepared antigen into the peritoneal cavity every 14 days. Animals that developed anti-CD40 titers were given an iv injection of 5-10 micrograms soluble recombinant CD40 antigen three to four days prior to fusion. Mouse spleens were harvested, and the isolated splenocytes used for hybridoma preparation.

Hybridoma Preparation: The P3x63Ag8.653 murine myeloma cell line (ATCC CRL 1580) was used for the fusions. RPMI 1640 (Invitrogen®) containing 10% FBS was used to culture the myeloma cells. Additional media supplements were added to the Hybridoma growth media, which included: up to 10% Hybridoma Enhancing Supplement (Sigma), 10% FBS (Sigma), L-glutamine (Gibco®) 0.1% gentamycin (Gibco), 2-mercaptoethanol (Gibco), with HAT (Sigma; $1.0\times10^4$ M hypoxanthine, $4.0\times10^{-7}$ M aminopterin, $1.6\times10^{-5}$ M thymidine media.

Spleen cells were mixed with the P3x63Ag8.653myeloma cells in a 6:1 ratio and pelleted by centrifugation. Polyethylene glycol was added dropwise with careful mixing to facilitate fusion. Hybridomas were allowed to grow out for one to two weeks until visible colonies become established. Supernatant was harvested and used for initial screening for rat IgG via ELISA using a human soluble CD40 fusion protein and a rat Fc specific detection. IgG positive supernatants were then assayed for CD40 specificity via flow cytometry. The hybridomas were also screened for cross-reactivity with cynomolgus macaque CD40 and all were positive for binding.

Hybridoma cells were expanded and cell pellets were frozen for RNA isolation and sequencing. The $V_H$ and $V_L$ coding regions of human mAbs were identified using RNA from the corresponding hybridomas. RNA was reverse transcribed to cDNA, the V coding regions were amplified by PCR and the PCR product was sequenced, inserted into human IgG2 vector, transiently expressed and purified by protein A column chromatography which led to the isolation of a number of antibodies of particular interest, which were designated as 3C3, 3G5, 1B4, 3B6, 6H6, 6H6, 2E1.2, 1B5-NK (in the latter case following N75K modification on FR3 of the heavy chain), and 3B6-NS (following N63S modification of antibody 3B6 on FR3 of the light chain to remove an N-linked glycosylation site).

Tables 1, 2, and 3 summarize the germline information and amino acid sequences of the $V_H$ and $V_L$ regions of the human mAbs (in the case of the amino acid sequences, the Complementarity Determining Regions (CDRs) are underlined). The corresponding nucleic acid sequences are provided in the sequence table headed "Summary of Sequence Listing" at the end of these Examples.

TABLE 1

| | | Germline Data | | |
|---|---|---|---|---|
| | | | Germline | |
| mAb | VH/VL | V | D | J |
| 3G5 | H | IGHV3-33*01 F (VH3-33) | IGHD3-10*01 F (D3-10) | IGHJ4*02 F (JH4b) |
| | L | IGKV3-15*01 F (L2) | | IGKJ5*01 F (JK5) |
| 3C3 | H | IGHV3-33*01 F (VH3-33) | IGHD3-10*02 F (D4-b) | IGHJ4*02 F (JH4b) |
| | L | IGKV1-27*01 F (A20) | | IGKJ3*01 F (JK3) |
| 3B6 | H | IGHV3-23*01 F (VH3-23) | IGHD2-15*01 F (D2-15) | IGHJ6*02 F (JH6b) |
| | L | IGKV2-28*01 F (A19) | | IGKJ1*01 F (JK1) |
| 6H6 | H | IGHV3-33*01 F (VH3-33) | IGHD3-10*01 F (D3-10) | IGHJ4*02 F (JH4b) |
| | L | IGKV3-15*01 F (L2) | | IGKJ4*01 F (JK4) |
| 1B4 | H | IGHV3-23*01 F (VH3-23) | IGHD1-26*01 F (D2-15) | IGHJ6*02 F (JH6b) |
| | L | IGKV2-28*01 F (A19) | | IGKJ1*01 F (JK1) |
| 1B5-NK | H | IGHV3-33*03 F (VH3-33) | IGHD6-19*01 F (D2-15) | IGHJ2*01 F (JH2) |
| | L | IGKV1-27*01 F (A20) | | IGKJ2*01 F (JK2) |
| 2 E1.2 | H | IGHV3-33*01 F (VH3-33) | IGHD3-10*01 F (D3-10) | IGHJ4*02 F (JH4B) |
| | L2 | IGKV3-15*01 F (L2) | | IGKJ4*01 F (JK4) |
| 3B6-NS | H | IGHV3-23*01 F (VH3-23) | IGHD2-15*01 F (D2-15) | IGHJ6*02 F (JH6b) |
| | L2 | IGKV2-28*01 F (A19) | | IGKJ1*01 F (JK1) |

TABLE 2

CDR Sequences

| mAb | VH/VL | CDR1 | SEQ ID NO | CDR2 | SEQ ID NO | CDR3 | SEQ ID NO |
|---|---|---|---|---|---|---|---|
| 3G5 | H | SNGIH (GFTFSSN) | 5, 6 | VIWSDGSNKFYADSVKG (WSDGSN) | 7, 8 | ASGSGSYYNFFDY (ASGSGSYYNFFDY) | 9, 10 |
|  | L | RASQSVRSNLA (RASQSVRSNLA) | 11, 12 | GASTRAT (GASTRAT) | 13, 14 | QQHNKWIT (QQHNKWIT) | 15, 16 |
| 3C3 | H | RYGMY (GFIFSRY) | 19, 20 | VIWYDGSYKYYADSVKG (WYDGSY) | 21, 22 | ESPWYYFDY (ESPWYYFDY) | 23, 24 |
|  | L | RASQGISNYLA (RASQGISNYLA) | 25, 26 | AASTLQS (AASTLQS) | 27, 28 | QKYKSAPFT (QKYKSAPFT) | 29, 30 |
| 3B6 | H | SYAMS (GFTFSSY) | 33, 34 | GITGTGGSTYYADSVKG (TGTGGS) | 35, 36 | RAGGSFYYYYGMDV (RAGGSFYYYYGMDV) | 37, 38 |
|  | L | RSSQSLLHSTGYNYLD (RSSQSLLHSTGYNYLD) | 39, 40 | LGSNRAS (LGSNRAS) | 41, 42 | MQALQTPWT (MQALQTPWT) | 43, 44 |
| 6H6 | H | SYGMH (GFTLSSY) | 47, 48 | VIWDDGSNKYYADSVKG (WDDGSN) | 49, 50 | AGGSGRYYNYFDY (AGGSGRYYNYFDY) | 51, 52 |
|  | L | RASQSVRSNLA (RASQ1SVRSNLA) | 53, 54 | GASTRAT (GASTRAT) | 55, 56 | QQHNNWLT (QQHNNWLT) | 57, 58 |
| 1B4 | H | SYAMT (GFTFSSY) | 61, 62 | GITGSGANTFYTDSVKG (TGSGAN) | 63, 64 | RNGGSYYYYYGMDV (RNGGSYYYYYGMDV) | 65, 66 |
|  | L | RSSQSLLHSSGYNYLD (RSSQSLLHSSGYNYLD) | 67, 68 | LGSNRAS (LGSNRAS) | 69, 70 | MQALQIPWT (MQALQIPWT) | 71, 72 |
| 1B5-NK | H | SFGMH (GFTFSSF) | 103, 104 | LIWFDGSSKYYADSVKG (WFDGSS) | 105, 106 | GFAAVAGWYFDF (GFAAVAGWYFDF) | 107, 108 |
|  | L | RASQGVRKYLA (RASQSVRSNLA) | 109, 110 | AASTLQS (AASTLQS) | 111, 112 | QKYFSAPYT (QKYFSAPYT) | 113, 114 |
| 2E1.2 | H | SYGMH (GFTFSSY) | 89, 90 | VIWDDGSNKYYADSVKG (WDDGSN) | 91, 92 | AGSSGRYYNYFDY (AGSSGRYYNYFDY) | 93, 94 |
|  | L | RASQSVRSNLA (RASQSVRSNLA) | 95, 96 | GASTRAT (GASTRAT) | 97, 98 | QQYNKWLI (QQYNKWLI) | 99, 100 |
| 3B6-NS | H | SYAMS (GFTFSSY) | 75, 76 | GITGTGGSTYYADSVKG (TGTGGS) | 77, 78 | RAGGSFYYYYGMDV (RAGGSFYYYYGMDV) | 79, 80 |
|  | L | RSSQSLLHSTGYNYLD (RSSQSLLHSTGYNYLD) | 81, 82 | LGSNRAS (LGSNRAS) | 83, 84 | MQALQTPWT (MQALQTPWT) | 85, 86 |

TABLE 3

Full-Length Variable Region Sequences

| mAb | VH/VL | SEQ ID NO | Sequence |
|---|---|---|---|
| 3G5 | H | 3 | QVQLVESGGGVVQPGKSLRLSCAASGFTFSSNGIHWVRQAPGKGLEWVAVIWSDGS NKFYADSVKGRFTISRDNSKNTLYLQMNSLRAEDTAVYYCARASGSGSYYNFFDYW GQGTLVTVSS |
|  | L | 4 | EIVMTQSPATLSVSPGERATLSCRASQSVRSNLAWYQQKPGQAPRLLIYGASTRAT GIPARFSGSGSGTEFTLTINSLQSEDFAVYYCQQHNKWITFGQGTRLEIK |
| 3C3 | H | 17 | QVQLVESGGGVVQPGRSLRLSCAGSGFIFSRYGMYWVRQAPGKGLEWVAVIWYDGS YKYYADSVKGRFTISRDNSKNTLYLQMNSLRAEDTAVYYCARESPWYYFDYWGQGT LVTVSS |
|  | L | 18 | DIQMTQSPSSLSASVGDRVTITCRASQGISNYLAWYQQKPGKVPKLLIYAASTLQS GVPSRFSGSGSGTDFTLTISSLQPEDVATYYCQKYKSAPFTFGPGTKVDIK |
| 3B6 | H | 31 | EVQLLESGGGLVQPGGSLRLSCAASGFTFSSYAMSWVRQAPGKGLEWVSGITGTGG STYYADSVKGRFTISRDNSKNTLYVQMNSLRAEDTAVYYCAKRAGGSFYYYYGMDV WGQGTTVTVSS |
|  | L | 32 | DIVMTQSPLSLPVTPGEPASISCRSSQSLLHSTGYNYLDWYLQKPGQSPQLLIYLG SNRASGVPDRFNGSGSGTDFTLKISRVEAEDFGVYYCMQALQTPWTFGHGTKVEIK |
| 6H6 | H | 45 | QVQLVESGGGVVQPGRSLRFSCAASGFTLSSYGMHWVRQAPGKGLEWVAVIWDDGS NKYYADSVKGRFTISRDNSKNTLYLQMNSLRAEDTAVYYCARAGGSGRYYNYFDYW GQGTLVTVSS |
|  | L | 46 | EIVMTQSPATLSVSPGERATLSCRASQSVRSNLAWYQQKPGQAPRLLIYGASTRAT GIPARFSGSGSGTDFTLTISSLQSEDFAVYYCQQHNNWLTFGGGTKVEIK |

TABLE 3-continued

Full-Length Variable Region Sequences

| mAb | VH/VL | SEQ ID NO | Sequence |
|---|---|---|---|
| 1B4 | H | 59 | EVQLLESGGGLVQPGGSLRLSCAASGFTFSSYAMTWVRQVPGKGLEWVSGITGSGA NTFYTDSVKGRFTISRDNSNNSLYLQMNSLRADDTAVYYCAKRNGGSYYYYGMDV WGQGTTVTVSS |
|  | L | 60 | DIVMTQSPLSLPVTPGEPASISCRSSQSLLHSSGYNYLDWYLQKPGQSPQLLIYLG SNRASGVPDRFSGSGSGTDFTLKISRVEAEDVGVYYCMQALQIPWTFGQGTKVEIK |
| 1B5-NK | H | 101 | QVQLVESGGGVVQPGRSLRLSCAASGFTFSSFGMHWVRQAPGKGLEWVTLIWFDGS SKYYADSVKGRFTISRDNSKNTLYLQMNSLRAEDTAVYYCVRGFAAVAGWYFDFWG RGTLVTVSS |
|  | L | 102 | DIQMTQSPSSLSASVGDRVTITCRASQGVRKYLAWYQQKPGKVPKLLIYAASTLQS GVPSRFSGSGSGTDFTLTISSLQPEDVATYYCQKYFSAPYTFGQGTKLEIK |
| 2E1.2 | H | 87 | QVQLVESGGGVVQPGRSLRLSCAASGFTFSSYGMHWVRQAPGKGLEWVAVIWDDGS NKYYADSVKGRFTISRDNSKNTLYLQMNSLRAEDTAVYYCARAGSSGRYYNYFDYW GQGTLVTVSS |
|  | L | 88 | EIVMTQSPATLSVSPGERATLSCRASQSVRSNLAWYQQKPGQAPRLLIYGASTRAT GIPDRFSGSGSGTEFTLTISSLQSEDFAVYHCQQYNKWLIFGGGTKVEIK |
| 3B6-NS | H | 73 | EVQLLESGGGLVQPGGSLRLSCAASGFTFSSYAMSWVRQAPGKGLEWVSGITGTGG STYYADSVKGRFTISRDNSKNTLYVQMNSLRAEDTAVYYCAKRAGGSFYYYGMDV WGQGTTVTVSS |
|  | L | 74 | DIVMTQSPLSLPVTPGEPASISCRSSQSLLHSTGYNYLDWYLQKPGQSPQLLIYLG SNRASGVPDRFSGSGSGTDFTLKISRVEAEDFGVYYCMQALQTPWTFGHGTKVEIK |

The full amino acid sequences of the heavy and light chains of the antibody 3C3 was as follows:

Light chain sequence with leader sequence removed)
(SEQ ID NO: 136)
*DIQMTQSPSSLSASVGDRVTITCRASQGISNYLAWYQQKPGKVPKLLIYAA*

*STLQSGVPSRFSGSGSGTDFTLTISSLQPEDVATYYCQKYKSAPFTFGPGT*

*KVDIK*RTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

Heavy chain sequence (with leader sequence removed)
(SEQ ID NO: 135)
*QVQLVESGGGVVQPGRSLRLSCAGSGFIFSRYGMYWVRQAPGKGLEWVAVI*

*WYDGSYKYYADSVKGRFTISRDNSKNTLYLQMNSLRAEDTAVYYCARESPW*

*YYFDYWGQGTLVTVSS*ASTKGPSVFPLAPCSRSTSESTAALGCLVKDYFPE

PVTVSWNSGALTSGVHTFPAVLQSSGLYSLSSVVTVPSSNFGTQTYTCNVD

HKPSNTKVDKTVERKCCVECPPCPAPPVAGPSVFLFPPKPKDTLMISRTPE

VTCVVVDVSHEDPEVQFNWYVDGVEVHNAKTKPREEQFNSTFRVVSVLTVV

HQDWLNGKEYKCKVSNKGLPAPIEKTISKTKGQPREPQVYTLPPSREEMTK

NQVSLTCLVKGFYPSDIAVEWESNGQPENNYKTTPPMLDSDGSFFLYSKLT

VDKSRWQQGNVFSCSVMHEALHNHYTQKSLSLSPG

In each case the variable sequence is shown in italics and the constant domain is shown in bold. The constant domain sequence is an IgG2 sequence from which the C-terminal lysines have been removed.

The same constant domain sequence was used for the other antibodies with their respective variable sequences as listed above.

Example 2

Determination of Affinity and Rate Constants of Human mAbs by Bio-Layer Interferometry (BLI)

Binding affinity and binding kinetics of various human anti-CD40 antibodies were examined by bio-layer interferometry (BLI) using an Octet™ QK$^e$ instrument (Pall ForteBio®, Menlo Park, Calif.) according to the manufacturer's guidelines.

Purified antibodies from Example 1 were captured on Anti-Human Fc Capture (AHC) biosensors (Fortebio Product No. 18-5060). Each antibody was prepared in dilution buffer (10 mMPO4+150 mM NaCl+1 mg/mL BSA+0.5% Tween 20, pH 7.2) to 0.5 µg/mL and loaded on freshly hydrated AHC biosensors for 35-50 sec at 25° C. and 1000 rpm plate shake speed to achieve a target response of 0.2 nm. Low levels of ligand were captured to limit any effects of mass transport of analyte on kinetic parameters. For one assay, eight biosensors were loaded with the same antibody.

Binding was determined by exposing six of the antibody loaded biosensors to analyte: soluble human CD40-MsIgG2a (Celldex®, 60 kD by SDS-PAGE). Affinity measurements were determined using 2-fold serial dilutions of analyte ranging from 3.13 to 0.098 nM in dilution buffer at 25° C. and 1000 rpm plate shake speed. Association of the antibody loaded biosensors in analyte wells was carried out for 1200 seconds, the biosensors were then moved to dilution buffer wells for 2.5 hrs (9000 sec) for dissociation measurements.

Corresponding controls were conducted in each case by keeping the two remaining biosensors with captured antibody in dilution buffer wells for association and dissociation steps. The data for the control biosensors was used to subtract background and account for biosensor drift and antibody dissociation from the biosensors.

Fortebio's Data Analysis Software version 8.2.0.7 (Pall ForteBio, Menlo Park, Calif.) was used in each case to derive kinetic parameters from the concentration series of analyte in dilution buffer binding to captured antibody. The association and dissociation curves were fitted to a 1:1 binding model using the data analysis software according to the manufacturer's guidelines.

The affinity and kinetic parameters (with background subtracted) as determined are shown in FIG. 1, where kon=rate constant of association, kdis=rate constant of dissociation, and $K_D$=dissociation equilibrium binding constant, determined by the ratio kdis/kon.

Example 3

Assays to Determine Human mAb Binding Characteristics to CD40

Microtiter plates were coated with recombinant human CD40-Fc in PBS, and then blocked with 5% bovine serum albumin in PBS. Protein A purified human mAbs from Example 1 and an isotype control were added at various concentrations and incubated at 37° C. The plates were washed with PBS/Tween and then incubated with a goat-anti-human IgG F(ab')2-specific polyclonal reagent conjugated to horseradish peroxidase at 37° C. After washing, the plates were developed with HRP substrate, and analyzed at OD 450-650 using a microtiter plate reader. Representatives binding curves are shown in FIG. 2.

Figure 3:
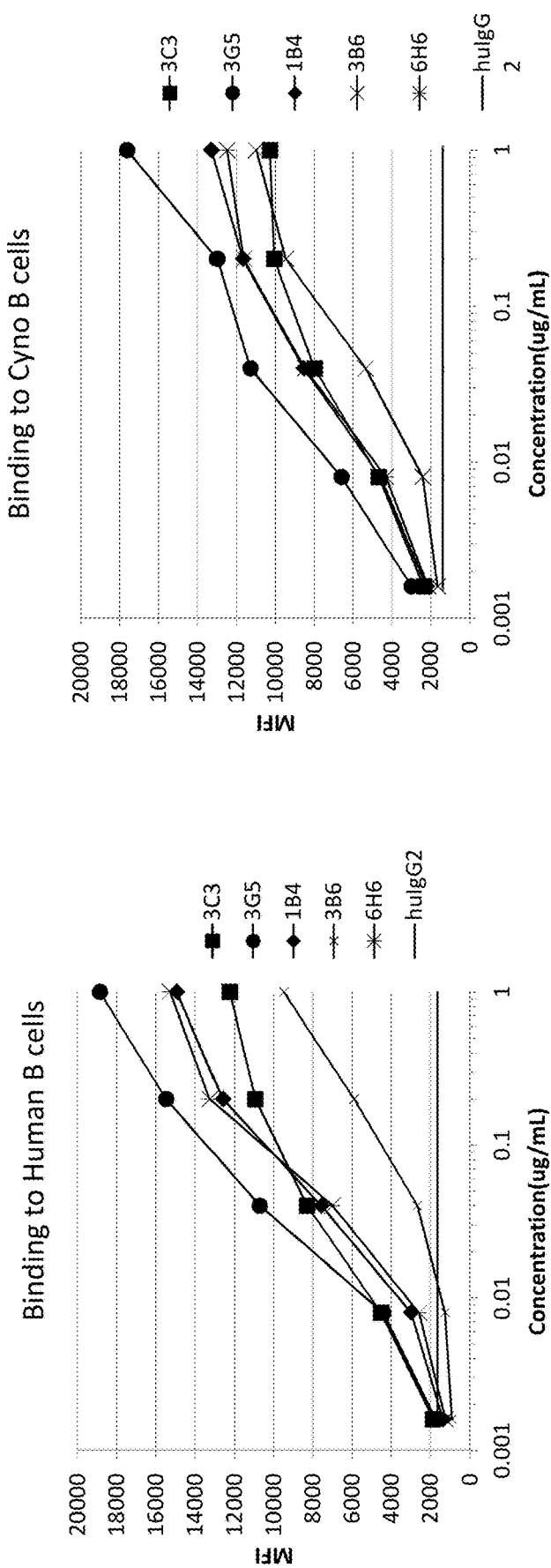
FIG. 3 are graphs showing the binding as mean fluorescence intensity (MFI) by flow cytometry as a function of human CD40 antibody concentration (3C3, 3G5, 1B4, 3B6, and 6H6) to purified human PBMCs (left) and cynomolgus macaque PBMCs (right).

To establish that cynomolgus macques are a relevant model for testing anti-CD40 mAbs, purified macaque PBMC's or human PBMC's were incubated with varying concentrations of anti-human CD40 mAb for 20 minutes at room temperature on a plate shaker. The cells were then washed twice with PBS containing 0.1% BSA and 0.05% $NaN_3$ (PBA). A goat anti-human IgG Fc-PE antibody was added for 20 minutes at room temperature on a plate shaker. B cells were identified by subsequent staining with an allophycocyanin (APC) conjugated CD20 antibody. Cells were analyzed by flow cytometry and binding curves are shown in FIG. 3, which indicate similar binding to CD40 from macaque and human.

Example 4

Blocking of sCD40L Binding by ELISA

Figure 4A:
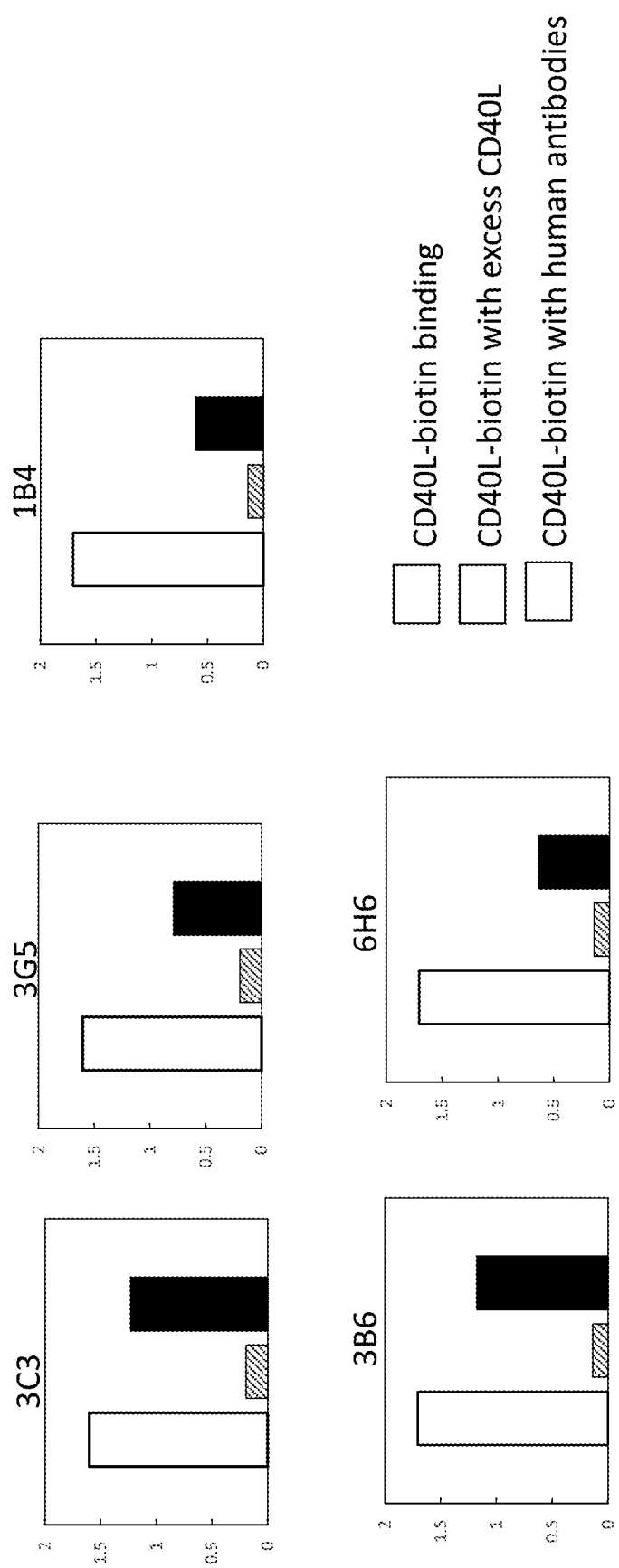

The effect of the human mAbs from Example 1 on the binding of soluble CD40 Ligand (sCD40L) to CD40 protein was measured by ELISA. A microtiter plate was coated with 2 µg/ml soluble recombinant human CD40/Fc chimera from R&D Systems, then blocked with 5% PBA. The anti-CD40 antibodies ([final]=100 µg/mL) were added to the plate, followed by soluble human recombinant CD40L-biotin from Immunex ([final]=0.5 µg/mL). CD40-captured rCD40L was detected with streptavidin-IRP and substrate Super Blue TMB. The results are shown in FIGS. 4A and B with controls as indicated.

Example 5

Binding to CD40 Cells

The ability of anti-CD40 human mAbs to bind to CD40 on cells expressing human CD40 on their surface was investigated by flow cytometry as follows:

Antibodies from Example 1 were tested for binding to human cell lines expressing human CD40 on their surface. Protein A purified human mAbs 3C3, 3G5, 1B4, 3B6, and 6H6 were incubated with, Raji and Ramos cells expressing human CD40 at room temperature on a plate shaker. After 20 minutes, the cells were washed with PBS containing 0.1% BSA and 0.05% $NaN_3$ (PBA) and the bound antibodies were detected by incubating the cells with a PE labeled goat anti-human IgG Fc-specific probe. The excess probe was washed from the cells with PBA and the cell associated fluorescence was determined by analysis using a FACSCanto II™ instrument (BD Biosciences, NJ, USA) according to the manufacturer's directions.

Figure 5:
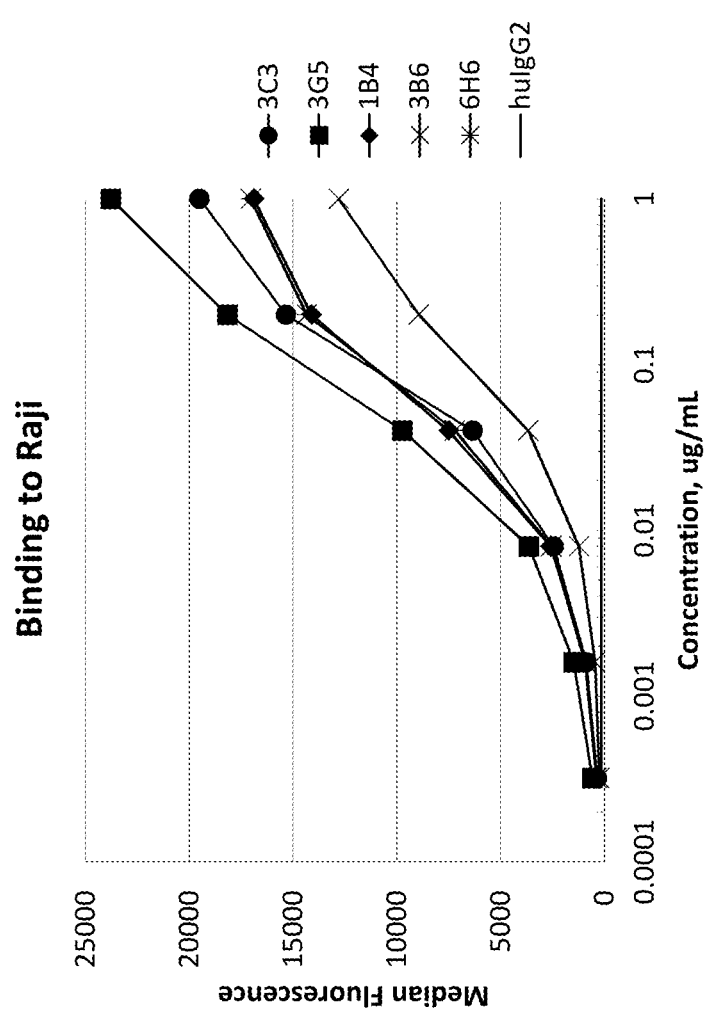
FIG. 5 is a flow cytometric analysis of human CD40 antibodies (3C3, 3G5, 1B4, 3B6, and 6H6) binding to CD40 on Raji cells expressing human CD40 on their surface.
Figure 6:
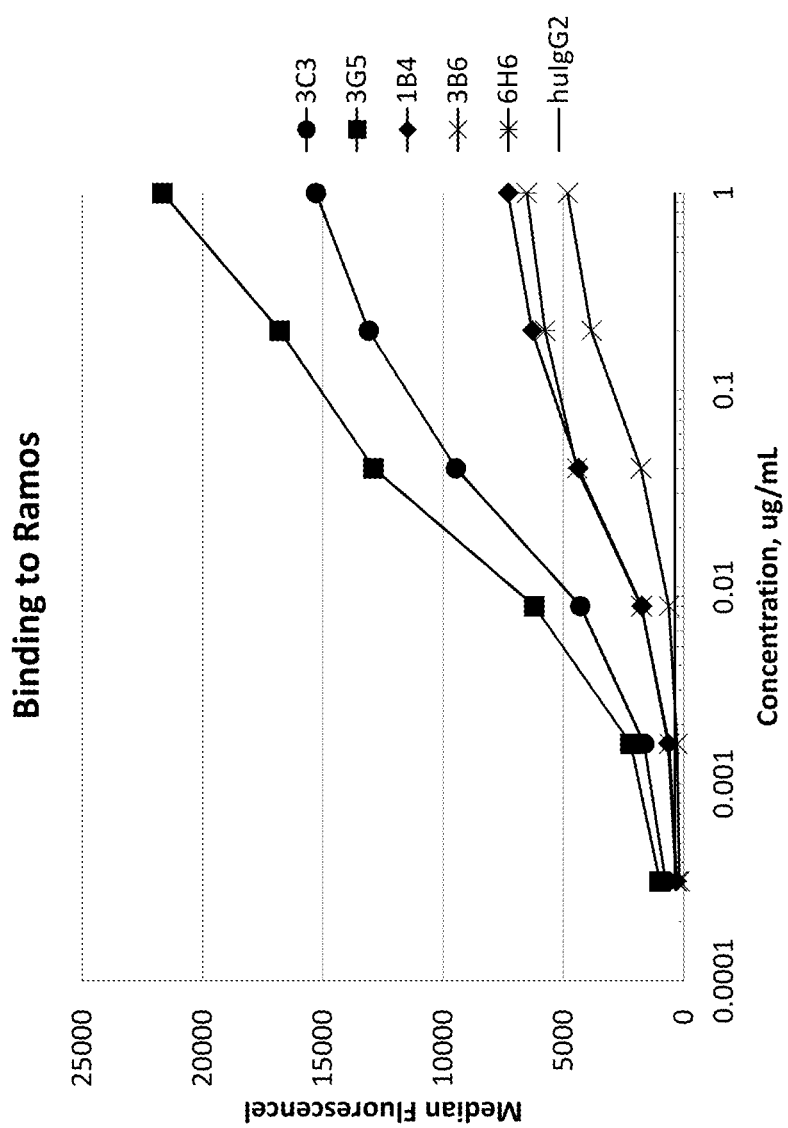
FIG. 6 is a flow cytometric analysis of human CD40 antibodies (3C3, 3G5, 1B4, 3B6, and 6H6) binding to CD40 on Ramos cells expressing human CD40 on their surface.

As shown in FIG. 5 (binding to Raji cells) and FIG. 6 (binding to Ramos cells), the human mAbs demonstrated high level binding to cells expressing human CD40 as a function of antibody concentration.

Example 6

CD95 Induction on Ramos Cells

Figure 7A:
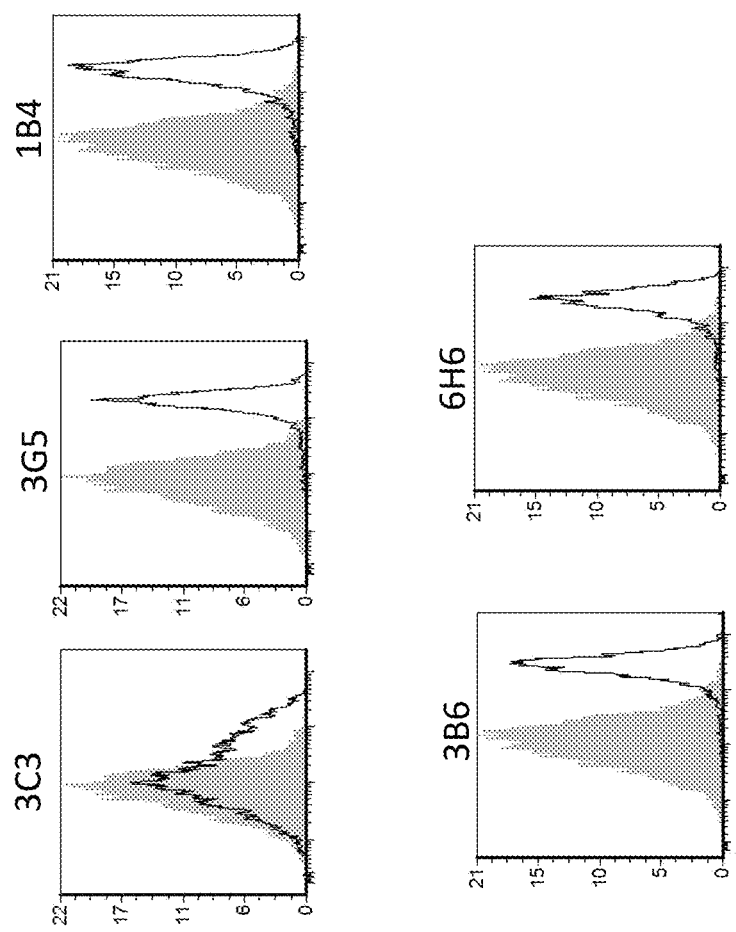

Ramos cells were incubated overnight at 37° C., 6% $CO_2$ with 2 ug/mL of the human anti-CD40 mAbs from Example 1. Then next day, they were washed once with PBA and stained with PE-conjugated anti-CD95 antibody (Becton Dickinson®) for 20 minutes at room temperature, with shaking. The excess labeled antibody was washed off and the samples read on a FACSCanto II™ instrument (BD Biosciences®, NJ, USA). As shown in FIGS. 7A and B ((in which the shaded plots represent untreated/control cells and the black lines represent cells treated with the antibodies as indicated), the 3C3 and the 1B5-NK antibodies show increases in CD95 and the other antibodies 3G5, 1B4, 3B6, 6H6, 2E1.2, and 3B6-NS were able to induce a strong increase in expression of surface expressed CD95.

Example 7

Dendritic Cell Activation

Dendritic cells were derived from human monocytes as follows: PMBC's were added to a T175 $cm^2$ flasks and monocytes allowed to adhere for ~2 hours at 37° C., 6% $CO_2$. The cells were removed and the monocytes cultured for 7 days in RPMI containing 10% FBS, 10 ng/mL IL-4 (R&D Systems®) and 100 ng/mL GM-CSF (R&D Systems). The cells were harvested and confirmed to be dendritic cells by expression of CD11c (not shown).

Figure 8A:
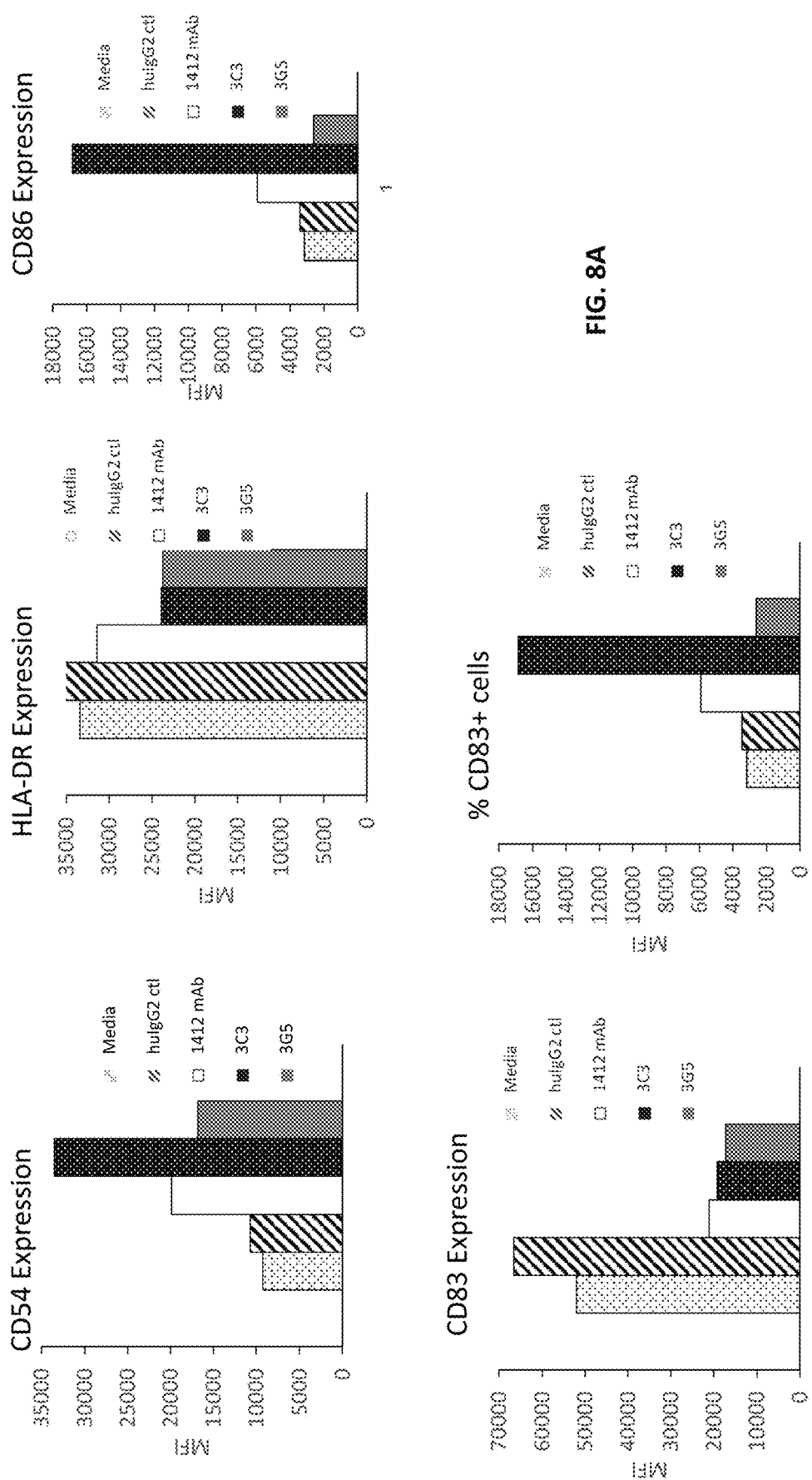
FIGS. 8A and 8B are graphs showing dendritic cell (DC) activation by human CD40 antibodies (3C3 and 3G5) based on the change in level of expression of the following markers: CD54, HLA-DR, CD86, CD83, and % CD83+ cells as indicated.

The cells were then incubated in the presence of 10 ug/mL 3C3 and 3G5 human anti-CD40 antibodies from Example 1 and appropriate controls at 37° C., 6% $CO_2$. After 72 hours, the cells were harvested and the supernatant was collected and stored for cytokine analysis. The cells were stained with the following labeled antibodies for 20 minutes at room temperature, shaking: HLA-DR V450, CD54 PE, CD86 APC, and CD83 BV510 (all from BD). Cells were then washed twice and analyzed on a FACSCanto II™ instrument (BD Biosciences, NJ, USA). FIG. 8A shows the level of expression for each of these markers when incubated with the indicated antibody or control.

Figure 9A:
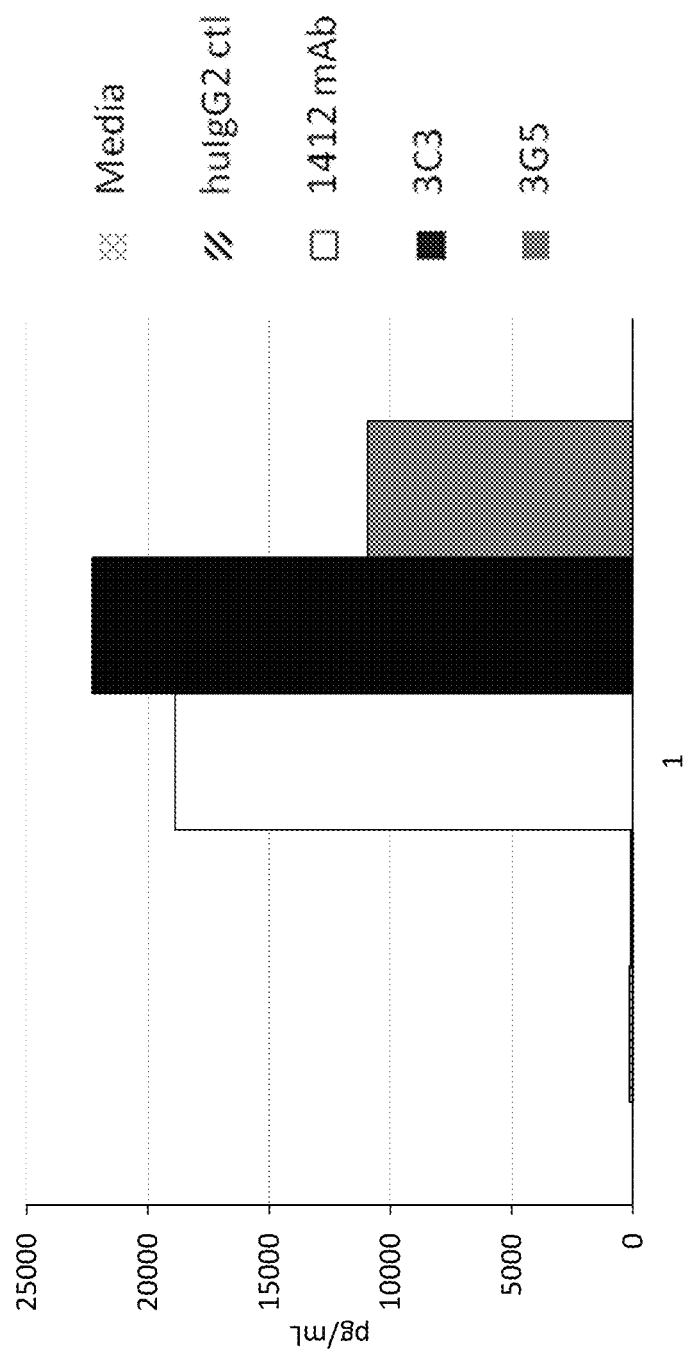
FIGS. 9A and 9B are graphs showing the induction of IL-12p40 by human CD40 antibodies (3C3 and 3G5).

Induction of IL-12p40 was evaluated in the supernatants from these 72 hour cultures by ELISA (R&D Systems). FIG. 9A shows the increase in IL-12p40 production with the 3C3 and 3G5 anti-CD40 antibodies relative to controls as indicated.

Figure 8B:
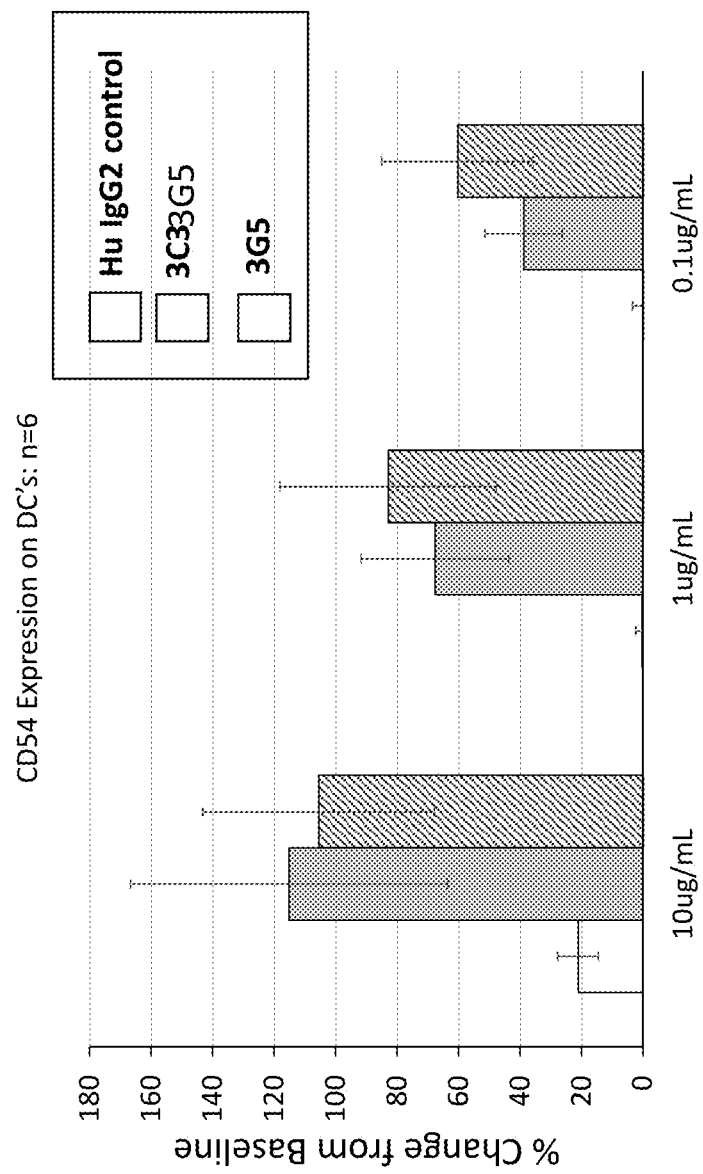

In a further experiment cells were incubated in the presence of 10, 1 and 0.1 ug/mL 3C3 and 3G5 human anti-CD40 antibodies from Example 1 and appropriate controls at 37° C., 6% $CO_2$. After 48 hours, the cells were harvested and the supernatant was collected and stored for cytokine analysis. The cells were stained with CD54 labeled antibody (BD) for 20 minutes at room temperature, shaking. Cells were then washed twice and analyzed on a FACSCanto II™ instrument (BD Biosciences, NJ, USA). FIG. 8B shows the level of expression for CD54 when incubated with the indicated antibody or control.

Figure 9B:
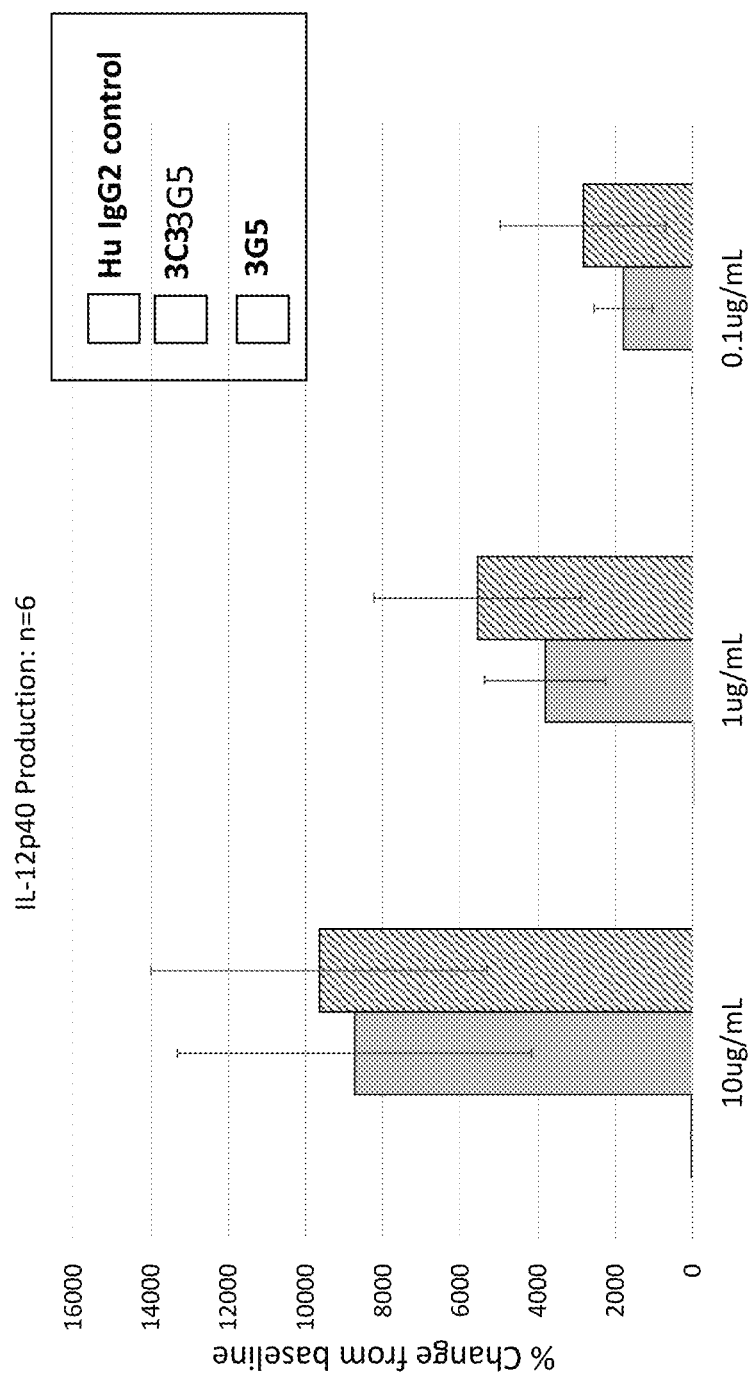

Induction of IL-12p40 was evaluated in the supernatants from these 48 hour cultures by ELISA (R&D Systems). FIG. 9B shows the increase in IL-12p40 production with the 3C3 and 3G5 anti-CD40 antibodies relative to controls as indicated.

Example 8

B Cell Activation

Figure 10A:
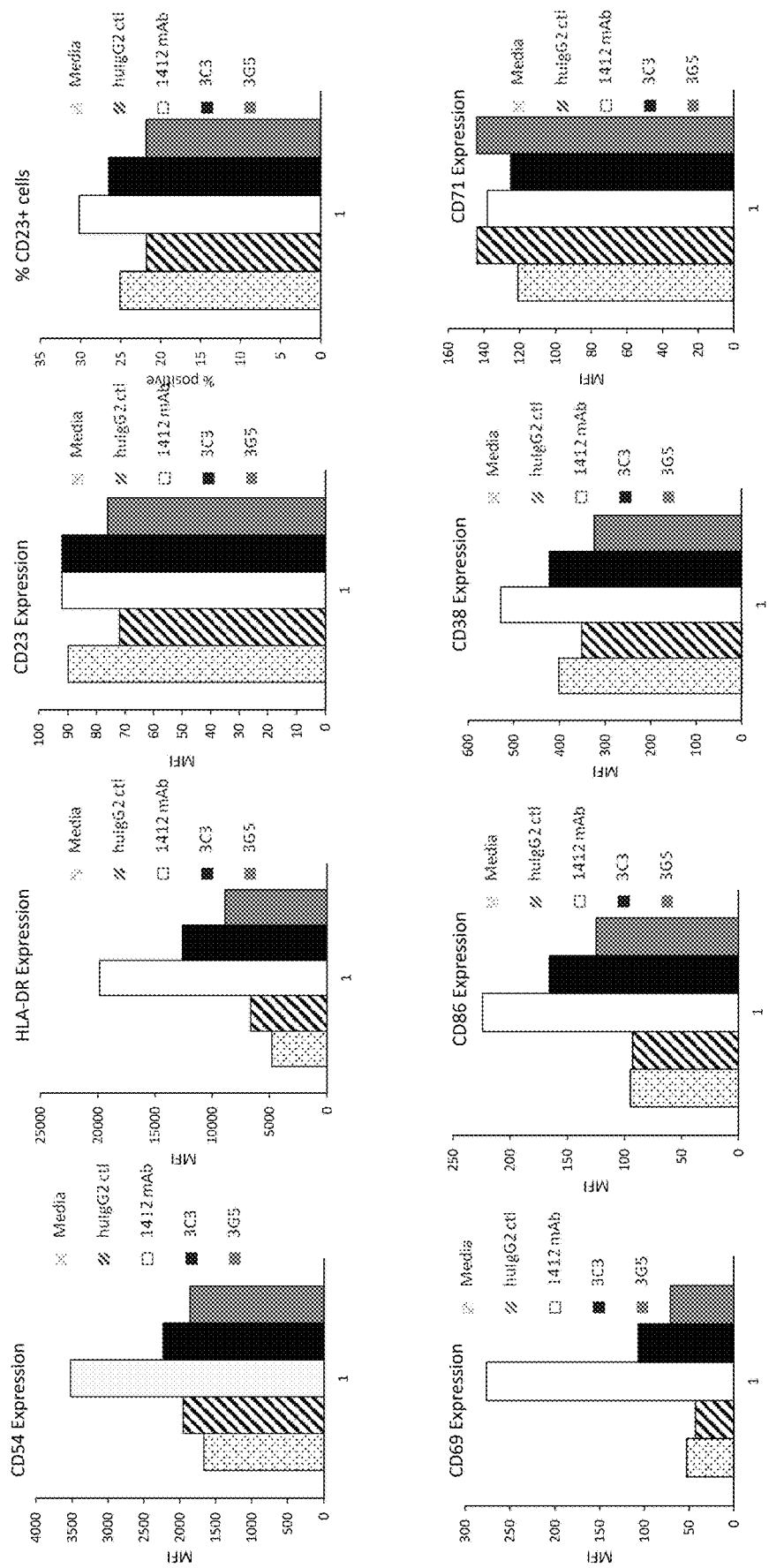
FIGS. 10A and 10B are graphs showing B cell activation by human CD40 antibodies (3C3 and 3G5) based on the change in level of expression of the following markers: CD54, HLA-DR, CD23, % CD23+ cells, CD69, CD86, CD38, and CD71 as indicated.

Whole blood was incubated with 10 ug/mL of 3C3 and 3G5 anti-CD40 antibodies from Example 1 overnight at 37° C., 6% CO2. The next day, the following labeled antibodies were used to stain B cells and activation markers: CD54 PE, HLA-DR V450, CD23 PerCP-Cy5.5, CD69 APC, CD86 APC, CD38 PerCP-Cy5.5 and CD71 PE. The cells were stained for 20 minutes at room temperature, shaking, then washed twice and read on a FACSCanto II™ instrument (BD Biosciences, NJ, USA). FIG. 10A shows the change in level of expression on each of these markers relative to controls as indicated.

Figure 10B:
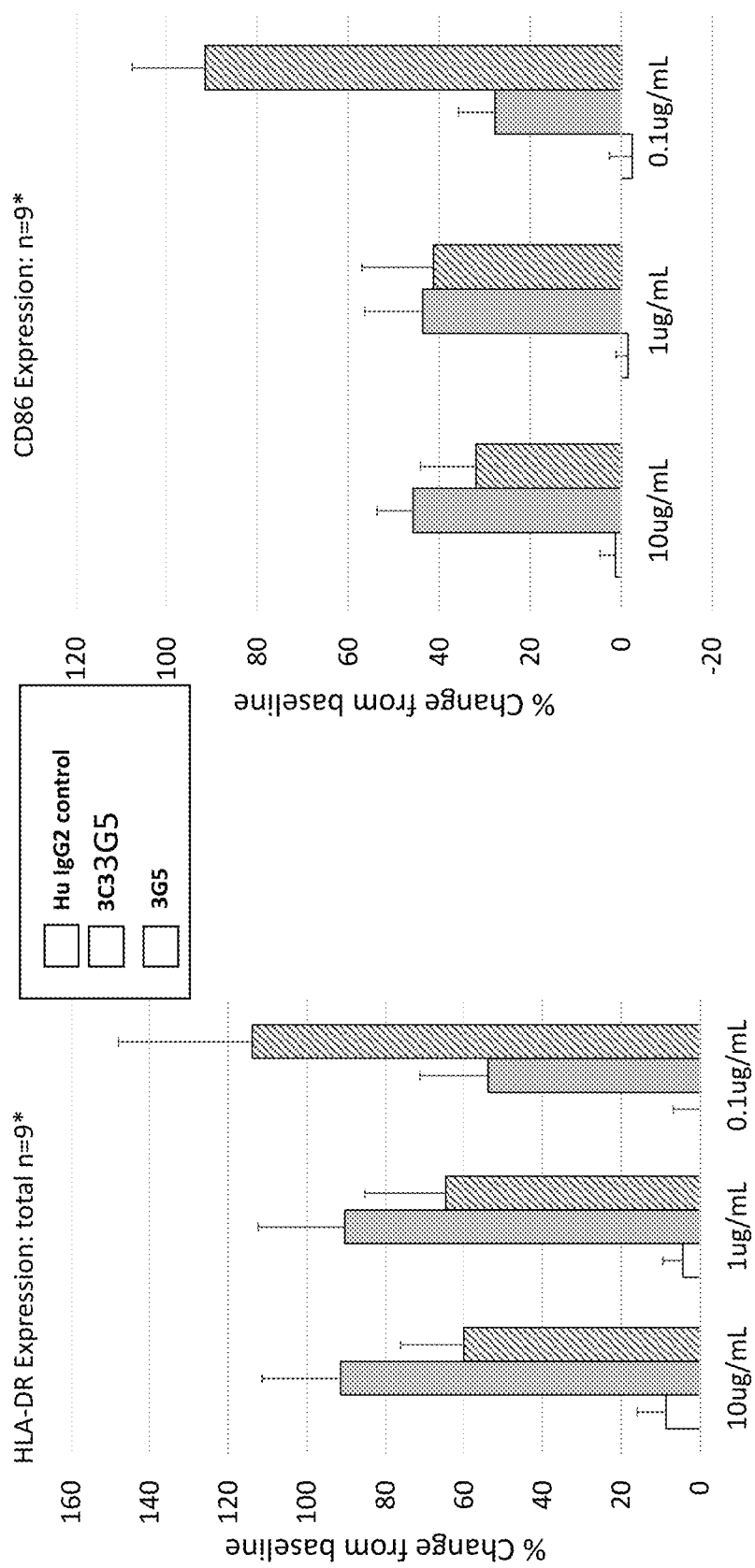

In a further experiment whole blood was incubated with 10, 1, and 0.1 ug/mL of 3C3 and 3G5 anti-CD40 antibodies from Example 1 overnight at 37° C., 6% $CO_2$. The next day, the following labeled antibodies were used to stain B cells and activation markers: CD19 V500, HLA-DR V450, CD86 APC (all from BD). The cells were stained for 20 minutes at room temperature, shaking, then washed twice and read on a FACSCanto II™ instrument (BD Biosciences, NJ, USA). FIG. 10B shows the change in level of expression on each of these markers relative to controls as indicated.

Example 9

NFκB Activation

Figure 11A:
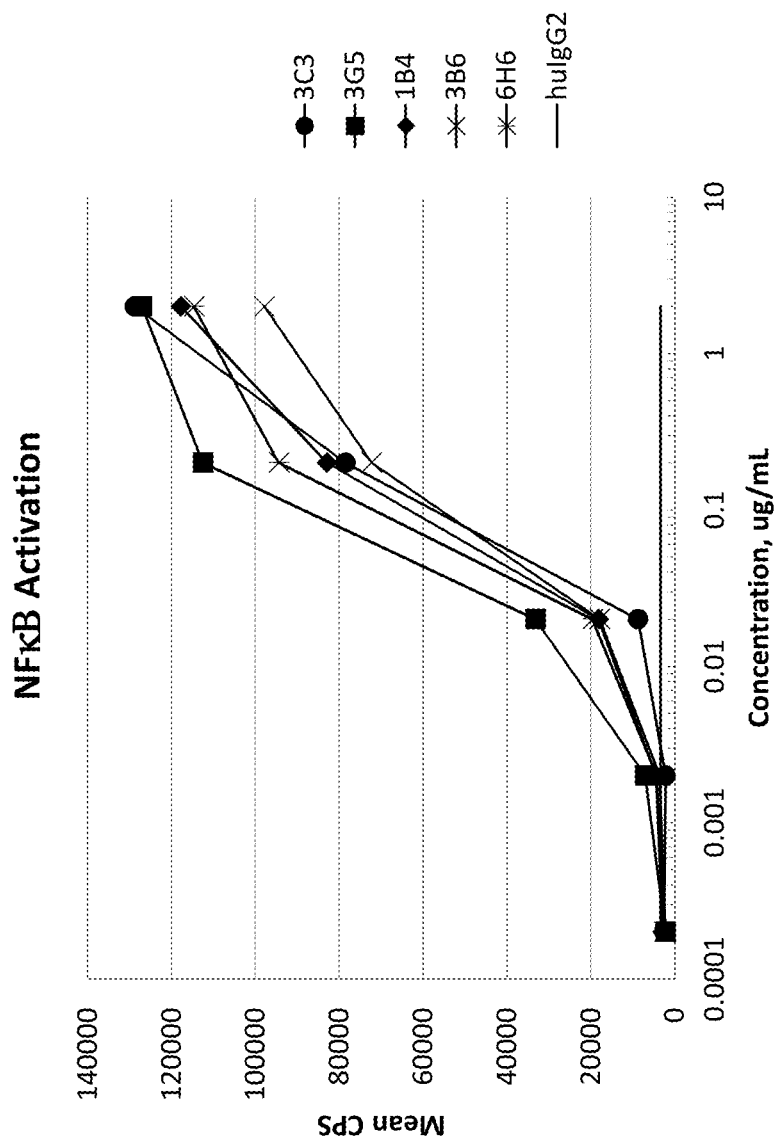
FIGS. 11A and 11B are graphs depicting NFkB activation by human CD40 antibodies using a luciferase reporter cell line expressing CD40.
Figure 11B:
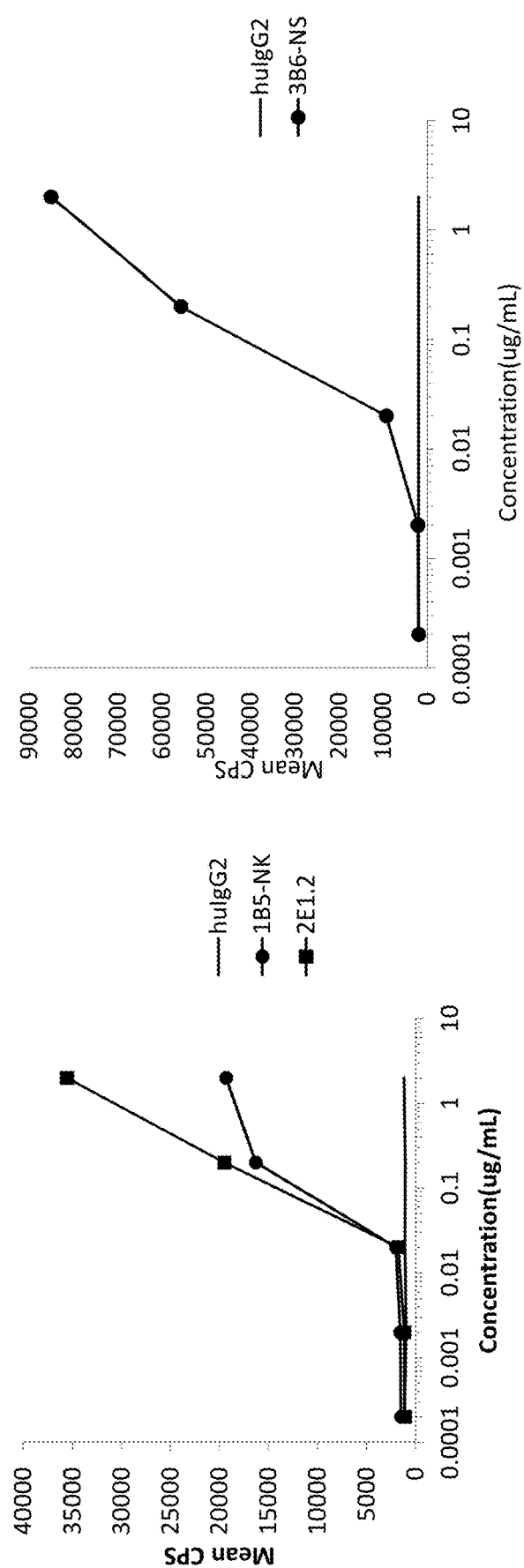

A luciferase reporter cell line expressing CD40 was incubated for 6 hours at 37° C., 6% $CO_2$ with various concentrations of the human anti-CD40 antibodies from Example 1. Luciferase expression was detected with the Luciferase Assay System by Promega® according to the manufacturer's guidelines. FIGS. 11A and 11B show the high level of NFkB activation induced by 3C3, 3G5, 1B4, 3B6, 6H6, 2E1.2, 1B5-NK, and 3B6-NS antibodies as a function of antibody concentration.

Example 10

Tumor Killing in Raji Xenograft SCID Mouse Model

Figure 12:
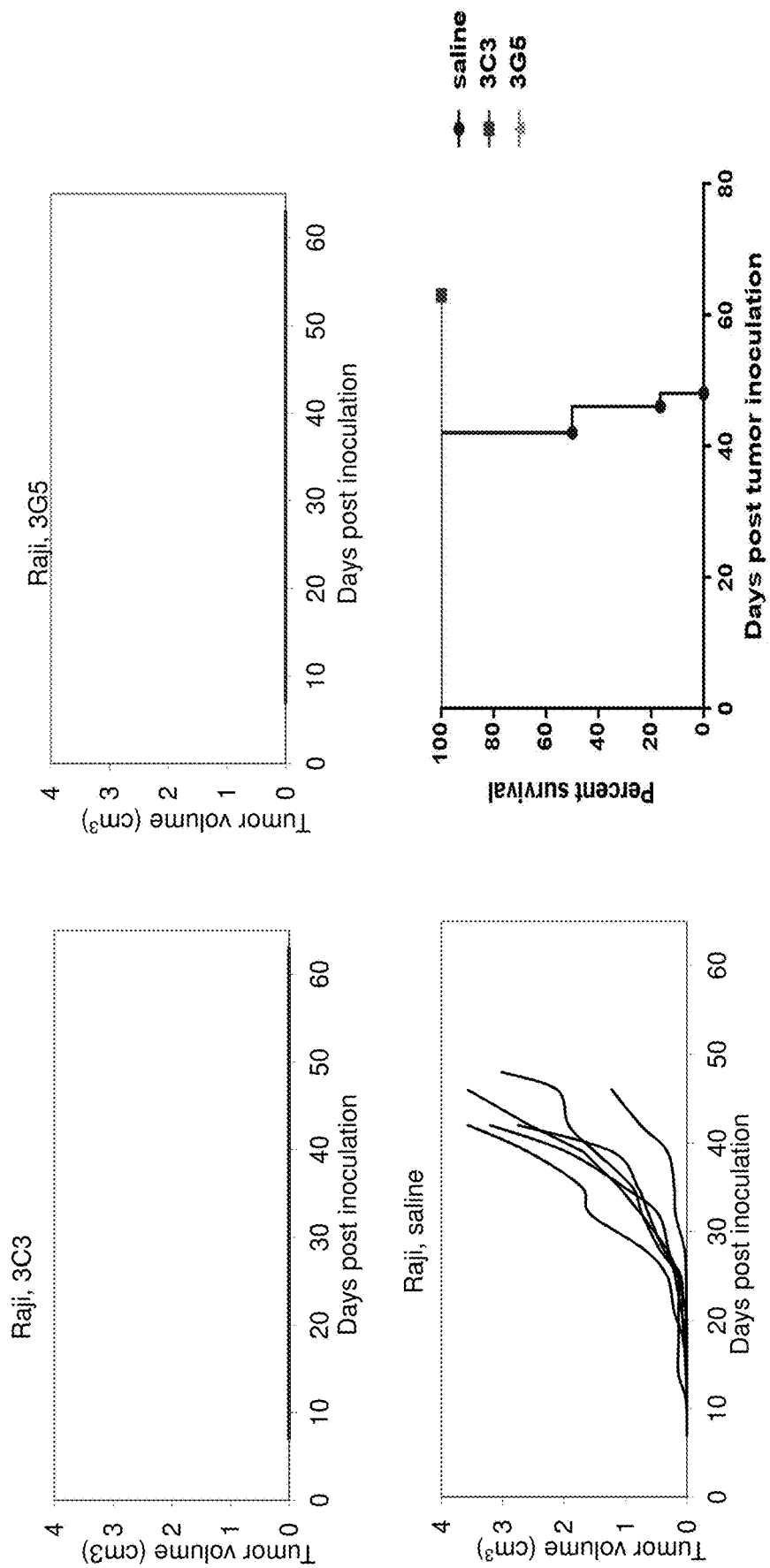
FIG. 12 are graphs showing the results of tumor growth and survival in a SCID mouse tumor model (Raji cells) following treatment with CD40 human antibody clones 3C3 and 3G5 via intraperitoneal administration, 0.3 mg per dose.

CB.17 SCID mice (purchased from Taconic Biosciences, Inc.) were maintained in a pathogen-free mouse facility. Lymphoma Raji cells ($1 \times 10^6$) were subcutaneously injected into SCID mice, 5 mice per group. On day 1, 5 and 11, these mice were treated with CD40 human mAbs clone 3C3 and 3G5 via intraperitoneal administration, 0.3 mg per dose. Tumor growth was measured with calipers 2 times a week. Results of tumor growth and survival analysis are shown in FIG. 12, from which it can be seen that, in the tumor challenged mice, treatment with the anti-CD40 antibodies inhibited the growth of tumors and significantly prolonged survival relative to saline treated controls.

Example 11

Tumor Killing in Ramos Xenograft SCID Mouse Model

CB.17 SCID mice (purchased from Taconic Biosciences, Inc.) were maintained in a pathogen-free mouse facility. Human lymphoma Ramos cells ($1 \times 10^6$) were subcutaneously injected into SCID mice on day 0, 5 mice per group. On day 1, 5 and 11, these mice were treated with anti-CD40 human mAb 3C3 or 3G5 via intraperitoneal administration, 0.3 mg per dose. Tumor growth was measured with calipers 2 times a week.

Figure 13:
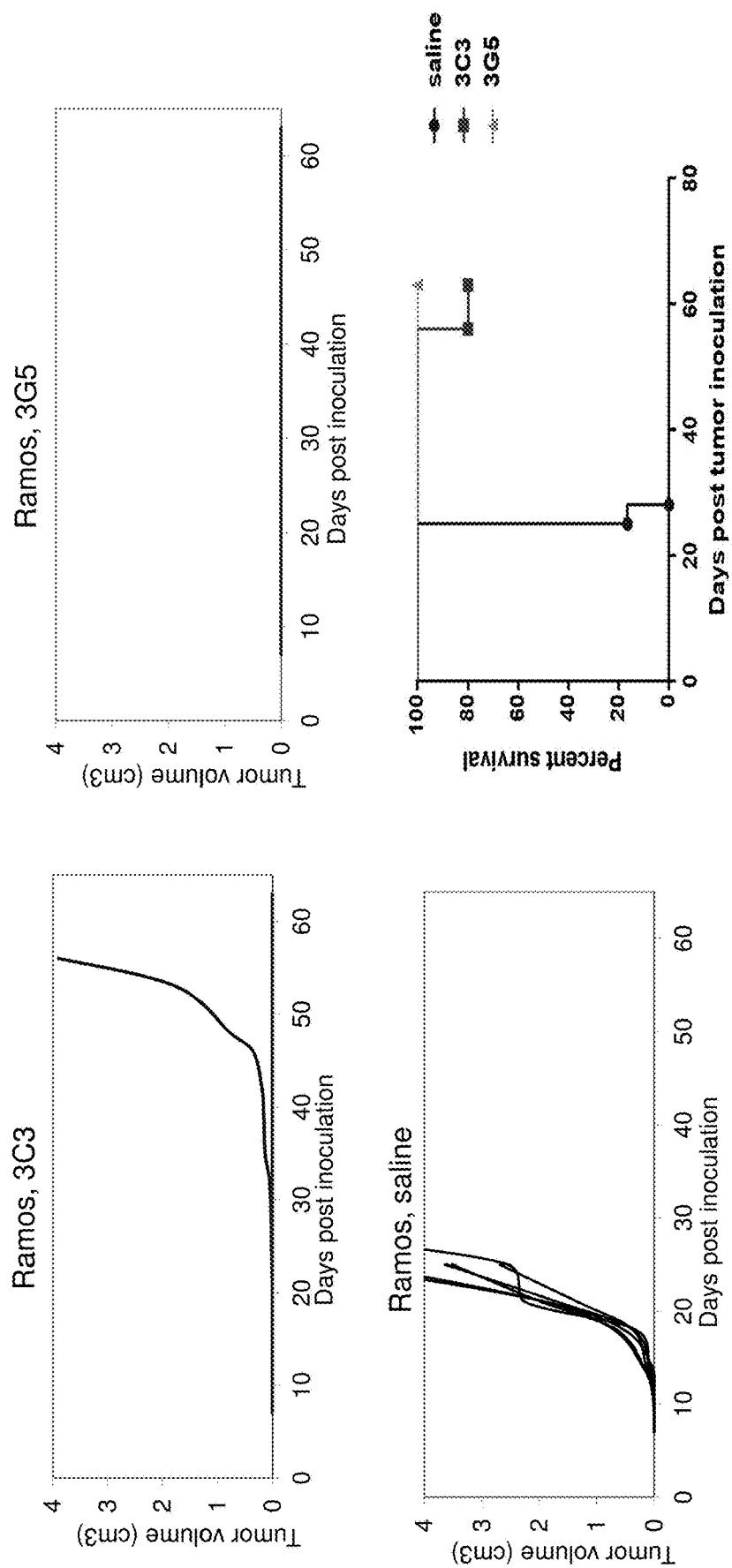
FIG. 13 are graphs showing the results of tumor growth and survival in a SCID mouse tumor model (Ramos cells) following treatment with CD40 human antibody clones 3C3 and 3G5 via intraperitoneal administration, 0.3 mg per dose.

The results, shown in FIG. 13, indicate that the anti-CD40 mAbs significantly inhibited the growth in tumor volume compared to saline treated controls, resulting in the survival of 100% (3G5) or 80% (3C3) of the tumor challenged mice.

Example 12

T-Cell Proliferation

Human Peripheral Blood Mononuclear Cells (PBMCs) isolated from buffy coat preparations were labeled with 0.5 uM carboxyfluorescein succinimidyl ester (CFSE) at room temperature while rotating for 5 minutes. The CFSE labeled PBMCs ($1.5 \times 10^6$) were dispensed into wells dry coated with anti-CD3 antibody (OKT3) at 0.2 ug/mL.

Figure 14A:
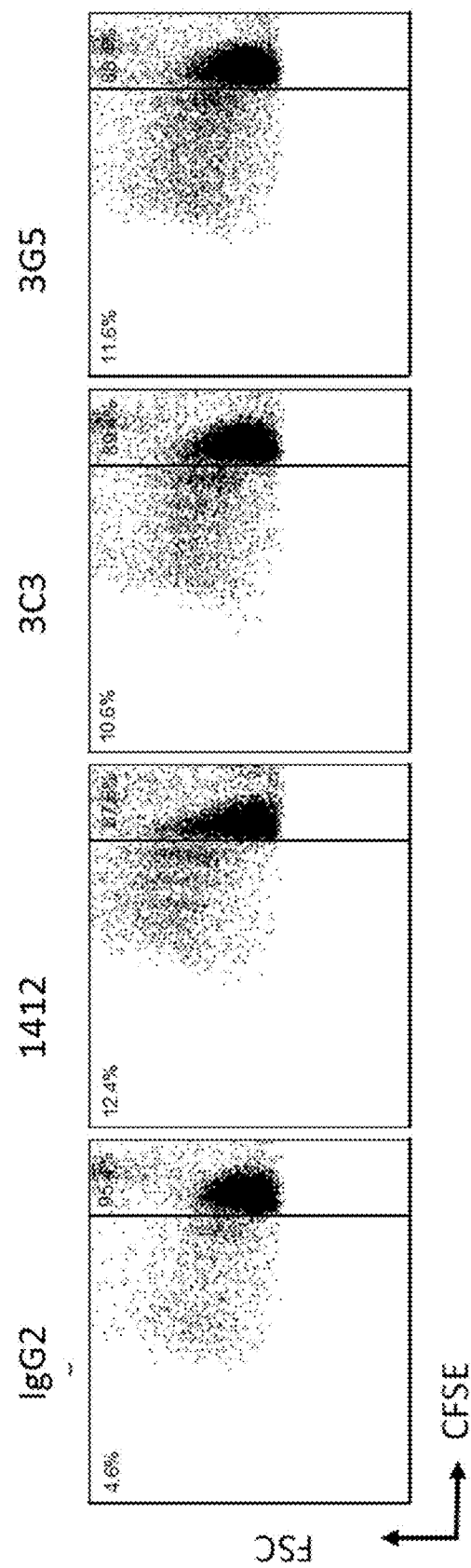
FIGS. 14A and 14B are graphs showing T-cell proliferation of labeled PBMCs incubated with CD40 antibodies as indicated or the isotype control (IgG2).
Figure 14B:
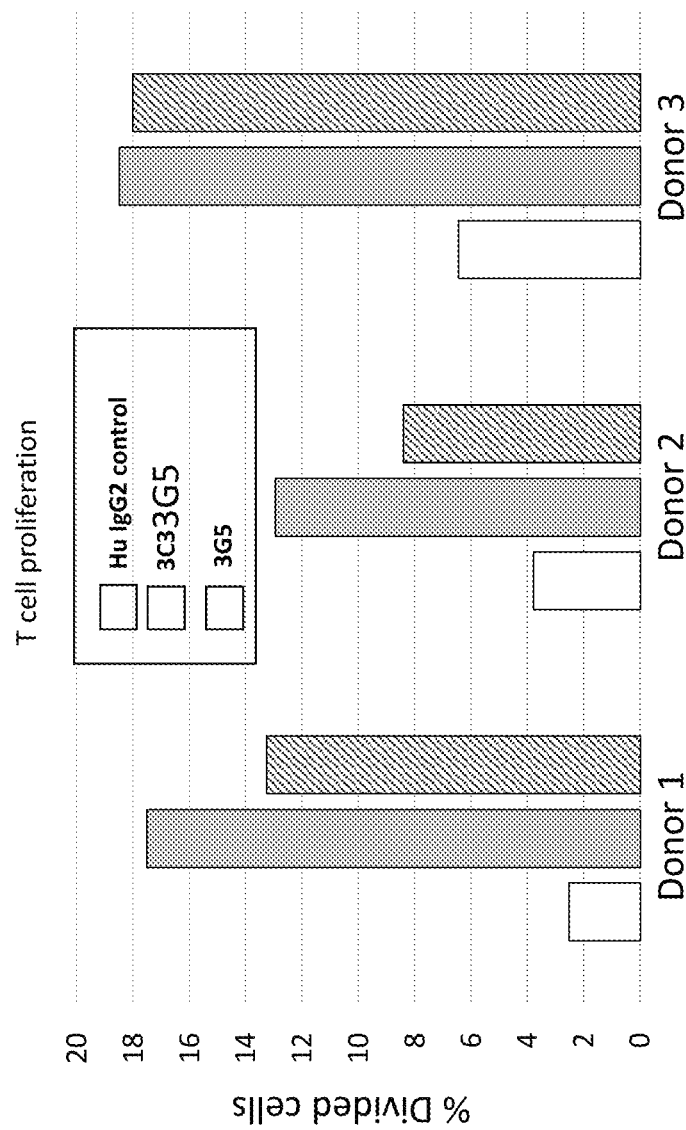

The CD40 antibodies (3G5, 3C3, 1412) or the isotype control (IgG2) were dispensed into the wells in soluble form at a final concentration of 10 ug/mL. The plates were incubated at 37° C. (5% $CO_2$) On day 6, the cells were harvested and stained with either anti-CD3-APC or the isotype control and analyzed by flow cytometry. Representative plots are shown in FIG. 14A from which it can be seen that the antibodies significantly enhanced T-cell proliferation as evidenced by the reduced intensities of CFSE staining in the CD3+ gate. Results from a repeat experiment are shown in FIG. 14B which shows the increase in dividing cells with the anti-CD40 antibodies relative to the isotype control.

Example 13

Binding to CD40 Independent of Fc Receptor Interaction

Figure 15:
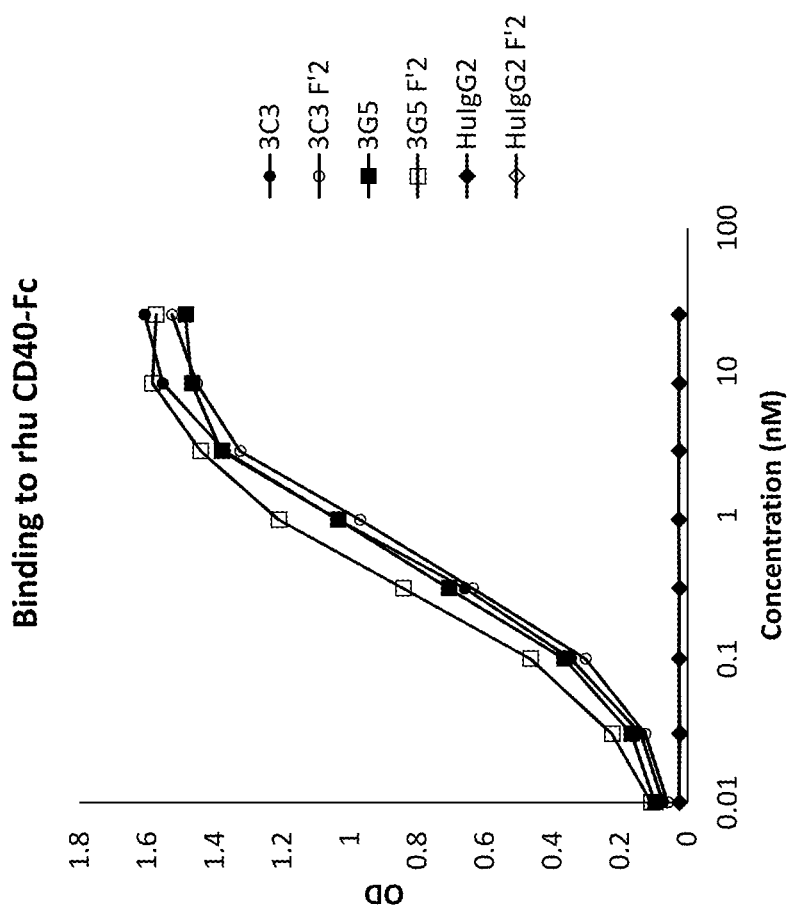
FIG. 15 is a graph showing binding to CD40 independent of Fc receptor interaction using CD40 antibodies 3C3 and 3G5.

Microtiter plates were coated with recombinant human CD40-Fc in PBS, and then blocked with 5% bovine serum albumin in PBS. Protein A purified human mAbs (whole IgG and F(ab')2 fragments as indicated) were added at various concentrations and incubated at 37° C. The plates were washed with PBS/Tween and then incubated with a goat-anti-human IgG F(ab')2-specific polyclonal reagent conjugated to horseradish peroxidase at 37° C. After washing, the plates were developed with HRP substrate, and analyzed at OD 450-650 using a microtiter plate reader. Results are shown in FIG. 15. The IgG2 and F(ab)'2 versions of each antibody show a similar concentration dependence for binding to CD40-Fc.

Example 14

CD40 Activation Independent of Fc Receptor Interaction

Figure 16:
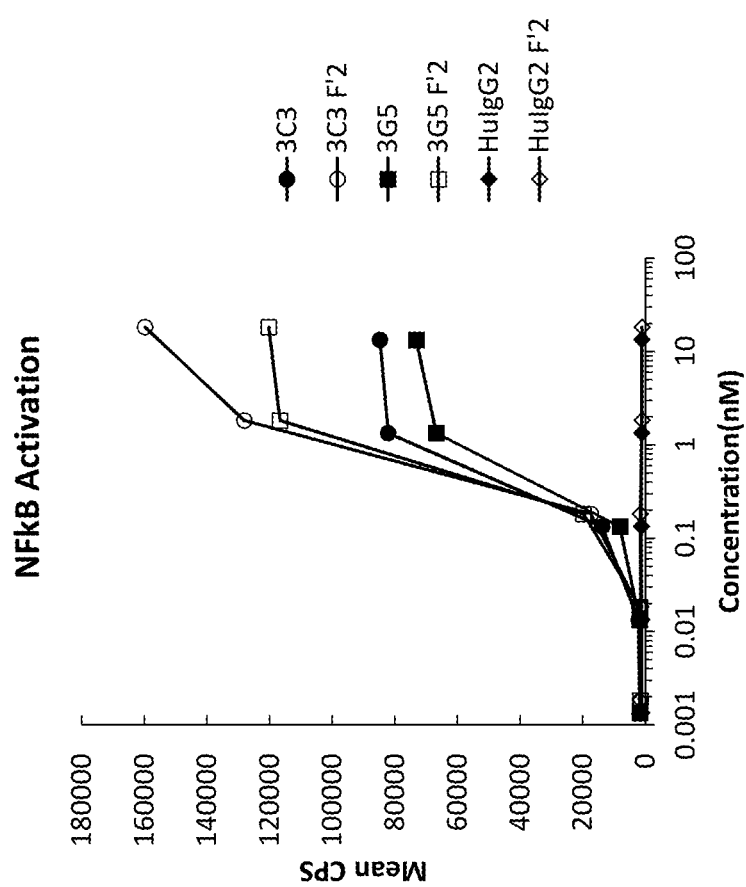
FIG. 16 is a graph showing NFκb activation using CD40 antibodies 3C3 and 3G5.

The luciferase reporter cell line expressing CD40 from Example 9 above was incubated for 6 hours at 37° C., 6% $CO_2$ with various concentrations of the human anti-CD40 antibodies (both whole IgG and F(ab')2 fragments as indicated). Luciferase expression was detected with the Promega Luciferase Assay System according to the manufacturer's guidelines. Results are shown in FIG. 16. These show that binding to the Fc receptor is not required for CD40 mediated activation of the reporter cell line by 3C3 and 3G5 because intact antibodies with Fc domains and their corresponding F(ab)'2 versions lacking Fc domains are both able to activate NFkB in the reporter cell line.

Example 15

CD95 Induction Independent of Fc Receptor Interaction

Figure 17:
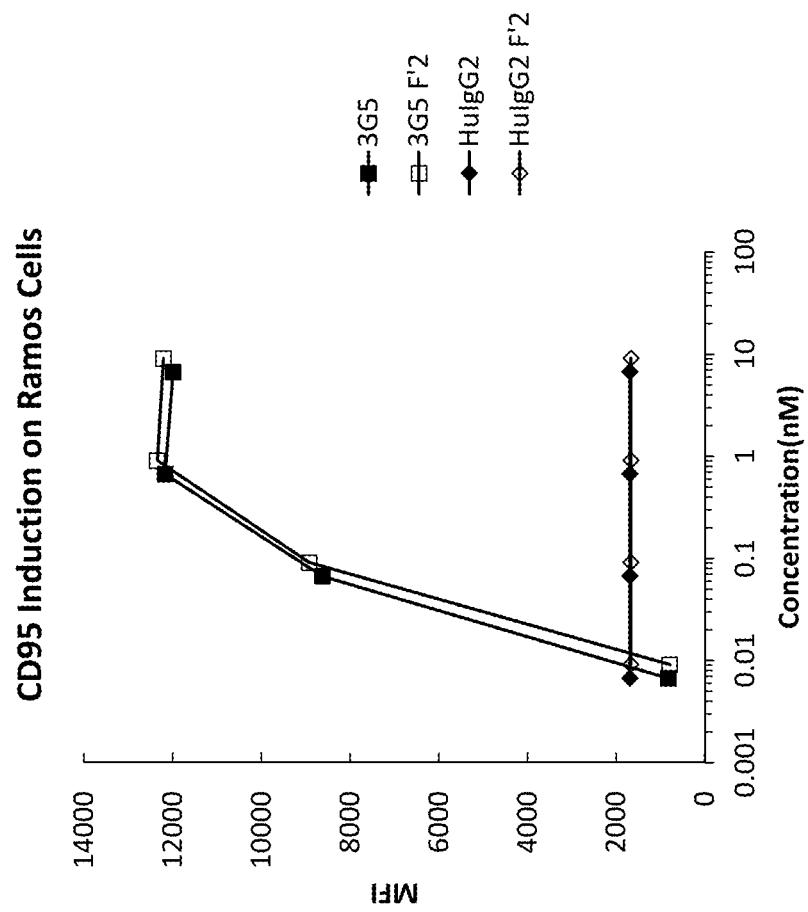
FIG. 17 is a graph showing CD95 induction on Ramos cells using CD40 antibodies 3C3 and 3G5.

Ramos cells were incubated overnight at 37° C., 6% $CO_2$ with various concentrations of the human anti-CD40 mAb's, (both whole IgG and F(ab')2 fragments as indicated). The next day they were washed once with PBA and stained with PE-conjugated anti-CD95 antibody (Becton Dickinson) for 20 minutes at room temperature with shaking. The excess labeled antibody was washed off and the samples read a FACSCanto II™ instrument (BD Biosciences, NJ, USA). Results are shown in FIG. 17. These data indicate that Fc receptor interactions are not required by 3G5 to induce the expression of CD95 on the CD40+ human lymphoblastoid line Ramos.

Example 16

Synergy with sCD40L

Figure 19:
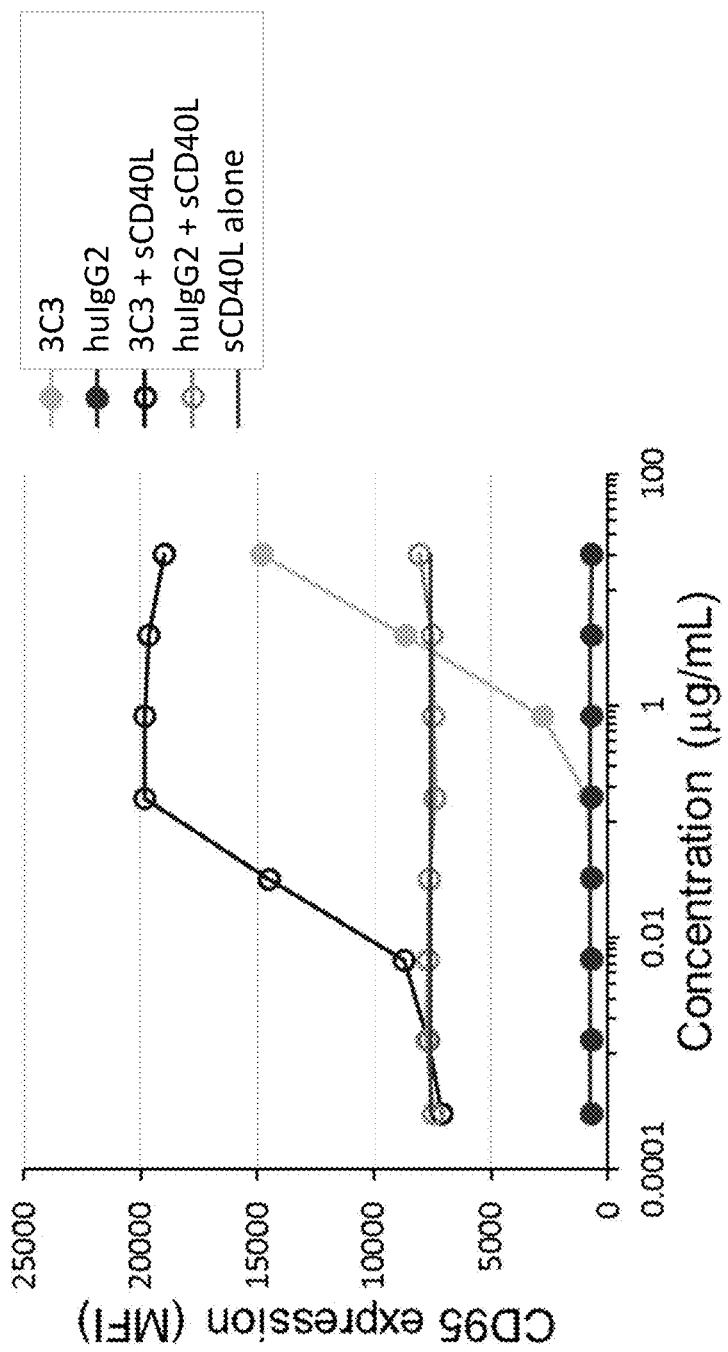
FIG. 19 is a graph showing the synergestic effect of CD40 antibody 3C3 with soluble CD40L on CD95 expression in Ramon cells.

Ramos cells were incubated overnight with the antibody 3C3 plus or minus 0.1 mg/ml soluble CD40 Ligand. The cells were then stained with anti-CD95-PE antibody and analyzed by flow cytometry. Results are shown in FIG. 19 and indicate that the anti-CD40 antibody 3C3 acted synergistically with sCD40L. Accordingly, antibody 3C3 (and anti-CD40 antibodies which bind to the same epitope as 3C3) exhibit synergistic agnostic effects with soluble CD40 ligand (sCD40L) and, therefore, have the ability to synergize with other therapeutic agents, including those which bind to the ligand binding site of human CD40. Representative synergistic effects include, for example, upregulation of immune function (e.g. T cell mediated immune responses as in vaccine therapies, NK activation in cancer therapies), inhibition of cell growth (e.g., in cancer therapy), and/or enhanced processing and presentation of an antigen by APCs (e.g., in vaccine therapy).

Example 17

Epitope Mapping of Anti-CD40 Human Antibodies 3C3 and 3G5 and sCD40 i) Generation of Truncated and Mutated Fragments of Soluble CD40 (sCD40).

Figure 20:
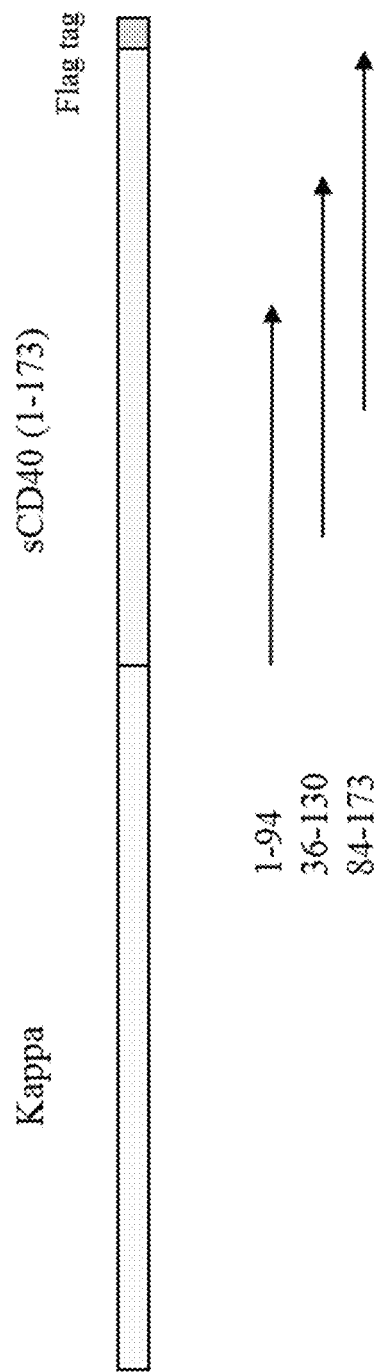
FIG. 20 is a schematic of soluble CD40 cDNA encoding the full length extracellular domain (ECD) spanning amino acid residues 1-173 with an N-terminal human kappa light chain and a C-terminal Flag tag.
Figure 21:
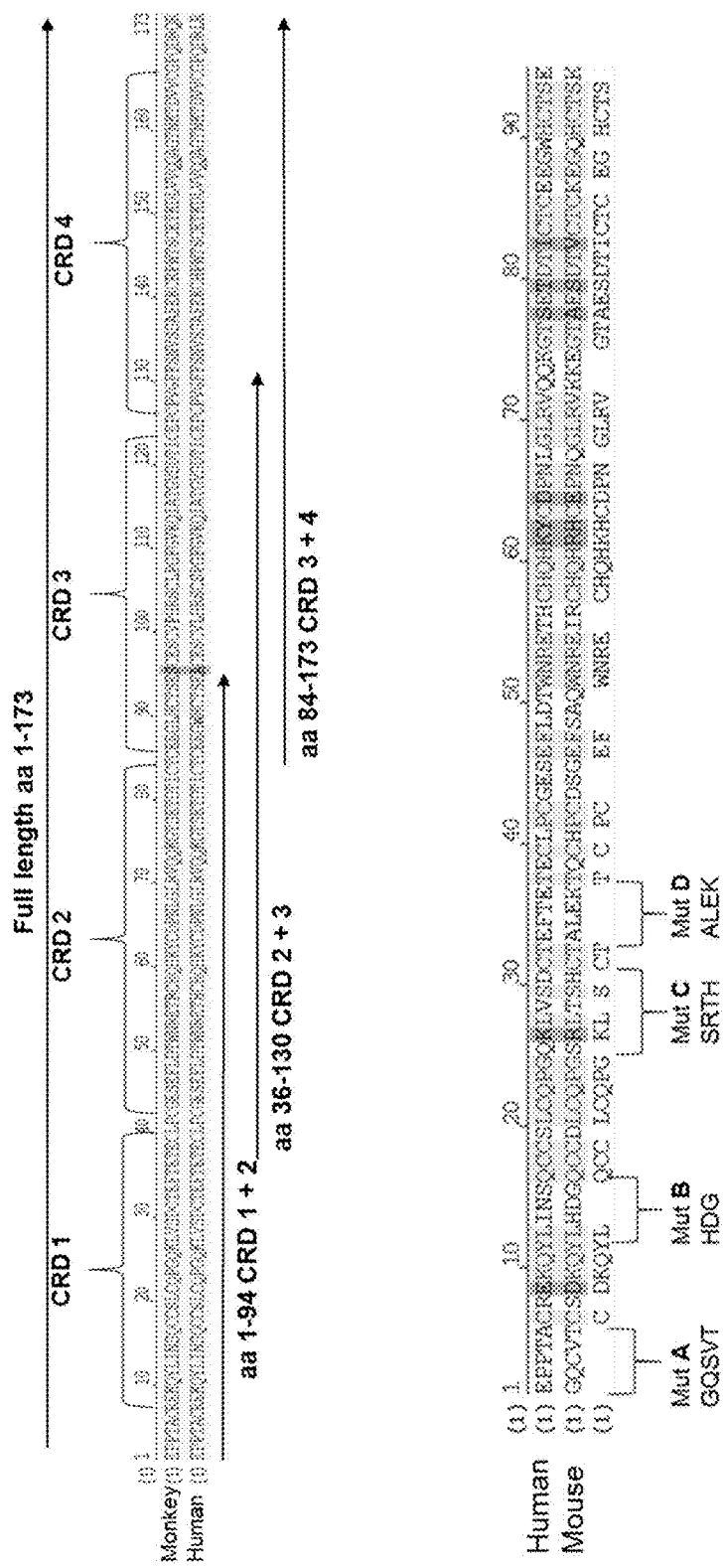
FIG. 21 shows an alignment of human CD40 ECD amino acid sequence (SEQ ID NO: 133) with monkey CD40 ECD amino acid sequence (SEQ ID NO: 139)(top) and mouse CD40 ECD amino acid sequence (bottom). Fragments generated are indicated (nucleotides 1-94 of SEQ ID NO: 133, SEQ ID NOS: 140-147).

Soluble CD40 (sCD40) cDNA encoding the full length extra cellular domain (ECD) spanning amino acid residues 1-173 (SEQ ID NO: 133), as well as three smaller fragments coding amino acids 1-94, 36-130 and 84-173, were synthesized by GenScript and inserted in-frame into a mammalian expression vector with an N-terminal human kappa light chain and a C-terminal Flag tag. The resulting kappa-sCD40-Flag fusion proteins were expressed by transient transfection into ExpiCHO-S cells (SAFC). Since the CD40 antibody 3C3 recognizes human and monkey but not mouse CD40, a series of mutated sCD40aa 1-94 cDNA were designed based on the differences between the human and mouse sequences, as shown in the alignments in FIGS. 20 and 21. The mutants were synthesized and cloned by GenScript®. All these truncated or mutated fragments were cloned into the same vector and expressed by the same cell line as aforementioned.

ii) Determining Binding by ELISA

The binding of 3C3 to the series of sCD40 fragments was tested by ELISA. 1 μg/ml of purified kappa-sCD40-Flag fusion proteins or CHO cell supernatants containing the sCD40 fusion proteins were captured to microtiter plates that were pre-coated with 5 ug/ml mouse anti-Flag antibody (Sigma) in PBS and blocked with 5% bovine serum albumin in PBS. Following incubation with the CD40 antibody, the microplates were washed with PBS/Tween, and incubated with a goat anti-human IgG Fc polyclonal reagent conjugated to horseradish peroxidase. After washing, the plates were developed with HRP substrate, and analyzed at OD 450-650 using a microtiter plate reader. An ELISA with a goat anti-human IgG Fab2-HRP to measure kappa chain binding was carried out in parallel to validate the sCD40 fusion protein expression from different transfections.

ELISA analysis with ~1 ug/ml full length sCD40 and the 3 truncated fragments determined that sCD40 N-terminal residues 1-94 are essential and sufficient for the binding of 3C3, since the fragment encoding amino acid residues 1-94 bound to 3C3 as well as the entire ECD, but the fragments encoding amino acid residues 36-130 or 84-173 of this sequence did not bind at all (see Table 4).

TABLE 4

| Fragment amino acid residues | Average OD | |
|---|---|---|
| | 3C3 | αFab2HRP |
| 1-173 | 1.264 | 1.264 |
| 1-94 | 1.803 | 1.720 |
| 36-130 | 0.024 | 1.695 |
| 84-173 | 0.024 | 1.669 |
| Mutant fragment of amino acids 1-94 | | |
| A (1-5) | 0.189 | 1.718 |
| B (13-15) | 2.032 | 1.730 |
| C (25, 26, 28, 30) | 1.487 | 1.685 |
| D (33-36) | 0.092 | 1.631 |

Based on these results, the critical recognition sites for 3C3 are within amino acids 1-35.

Figure 22:
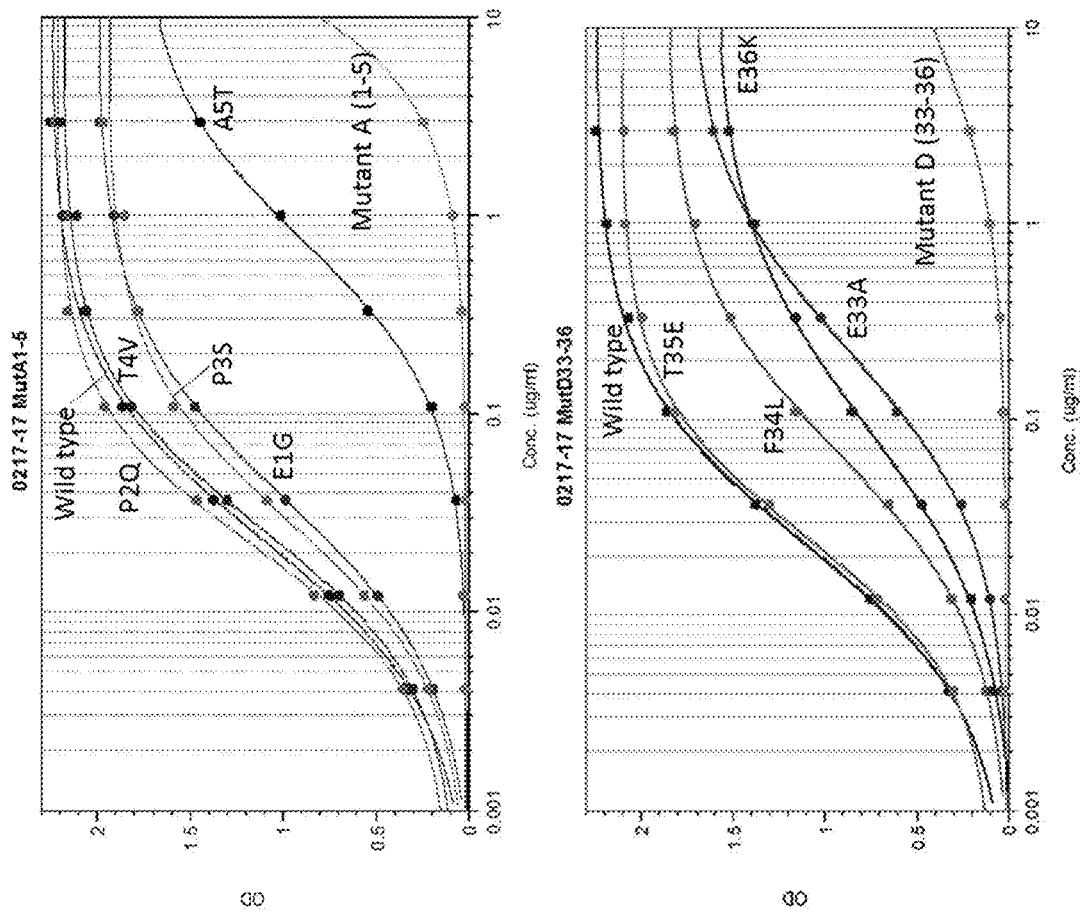
FIG. 22 provides graphs showing binding of CD40 antibody 3C3 to human CD40 ECD fragment A (amino acid residues 1-5; top) or fragment D (amino acid residues 33-36; bottom) with various point mutations or combinations thereof.

To further identify critical regions and amino acid residues for the conformational organization of the binding site of 3C3, ~2 ug/ml 13 mutated sCD40 (amino acid residues 1-94) fragments (4 regional multiple mutations and 9 single mutations) were tested by ELISA (see Tables 5 and 6 showing results from separate experiments, and FIG. 22).

TABLE 5

| Fragment amino acid residues | Average OD | |
|---|---|---|
| | 3C3 | αFab2HRP |
| 1-94 | 2.157 | 1.473 |
| Mutant fragment of amino acids 1-94 | | |
| A (1-5) | 0.167 | 1.489 |
| D (33-36) | 0.124 | 1.429 |
| Point Mutation | | |
| E1G | 1.965 | 1.487 |
| P2Q | 2.077 | 1.490 |
| P3S | 2.011 | 1.489 |
| T4V | 2.152 | 1.519 |
| A5T | 1.126 | 1.517 |
| E33A | 1.620 | 1.521 |
| F34L | 1.883 | 1.500 |
| T35E | 2.072 | 1.487 |
| E36K | 1.369 | 1.433 |
| PBA | 0.031 | 0.011 |

TABLE 6

| | OD | | |
|---|---|---|---|
| | 3C3 | 3G5 | αFab2HRP |
| Fragment amino acid residues | | | |
| Full length 1-173 | 2.364 | 2.214 | 1.525 |
| 1-94 | 2.151 | 2.170 | 1.755 |
| 36-130 | 0.029 | 0.048 | 1.716 |
| 84-173 | 0.024 | 0.038 | 1.599 |
| Mutant fragment of amino acids 1-94 | | | |
| A (1-5) | 0.250 | 2.139 | 1.699 |
| B (13-15) | 2.375 | 1.876 | 1.710 |
| C (25, 26, 28, 30) | 2.016 | 2.161 | 1.604 |
| D (33-36) | 0.233 | 0.042 | 1.548 |
| Point Mutation | | | |
| E1G | 2.011 | 2.083 | 1.720 |
| P2Q | 2.197 | 2.158 | 1.754 |
| P3S | 2.012 | 2.188 | 1.712 |
| T4V | 2.213 | 2.210 | 1.664 |
| A5T | 1.511 | 2.201 | 1.698 |
| E33A | 1.695 | 0.074 | 1.709 |
| F34L | 1.845 | 1.192 | 1.686 |
| T35E | 2.102 | 2.128 | 1.682 |
| E36K | 1.689 | 1.930 | 1.674 |
| <0.25 | | | |
| 0.25 < x < 1.2 | | | |
| 1.2 < x < 1.9 | | | |

Multiple mutations of residues 1-S almost completely abrogated 3C3. Point mutations of residues 1-4 did not reduce binding to 3C3. The point mutation of residue 5 dramatically reduced binding but not to the extent of the multiple mutation protein.

Multiple mutations of residues 13-15 did not reduce 3C3 binding. Multiple mutations of residues 25, 26, 28 and 30 caused a slight reduction in 3C3. Point mutations were not tested in these regions.

Multiple mutations of residues 33-36 almost completely abrogated 3C3 binding. The point mutation of residue 35 had no effect on binding. The point mutations of 33, 34 and 36 decreased 3C3 binding but not to the extent of the multiple mutation protein. An alternate CD40 antibody, 3G5, was tested for binding to all fragments and mutants and was shown to be different than 3C3 (Table 6). The multiple mutation of residues 1-5 did not reduce binding while the mutation of residues 33-36 eliminated binding. Unlike 3C3, the point mutation of residue 33 completely eliminated binding and the mutation of 34 significantly reduced binding.

Example 18

Biological and Toxicity Profile

A non-GLP pilot study was performed in naive cynomolgus macaques. This study was designed to provide preliminary data on the biological and toxicity profile of 3C3. An alternative anti-CD40 antibody (3G5) was also evaluated. The test articles were administered by intravenous injection in a saphenous vein on Day 1 (0.2 mg/kg or vehicle) and again on Day 29 (2 mg/kg or vehicle). Animals also received a subcutaneous (1 mg) injection of keyhole limpet hemocyanin (KLH) on Day 1 and 29. Evaluations for potential test article-related effects were based on clinical signs, body temperature, clinical pathology parameters (hematology, coagulation, clinical chemistry, and urinalysis), anti-drug antibodies, cytokines, T-cell dependent antibody response analyses (TDAR), flow cytometry, and toxicokinetic parameters. Body weights were recorded once prior to test article administration and weekly thereafter. This was designed as a survival study with no planned necropsy.

Figure 23A:
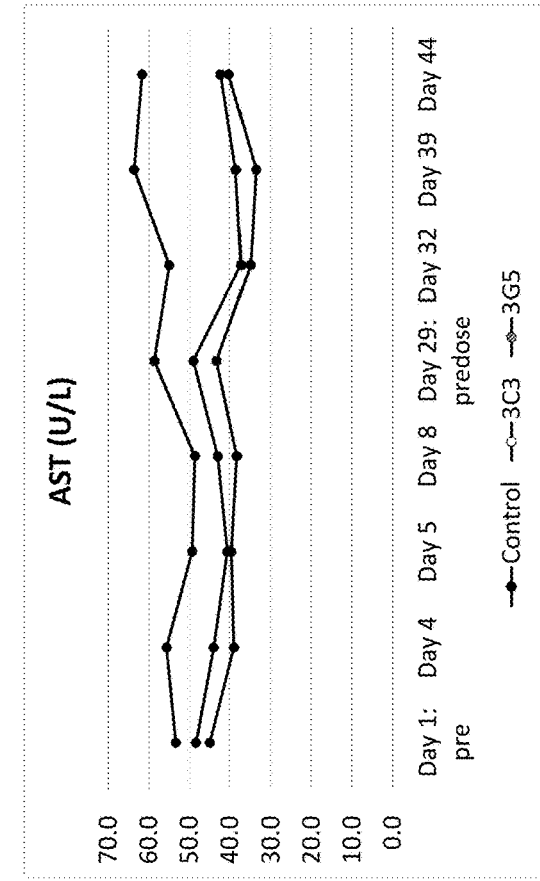
Figure 23B:
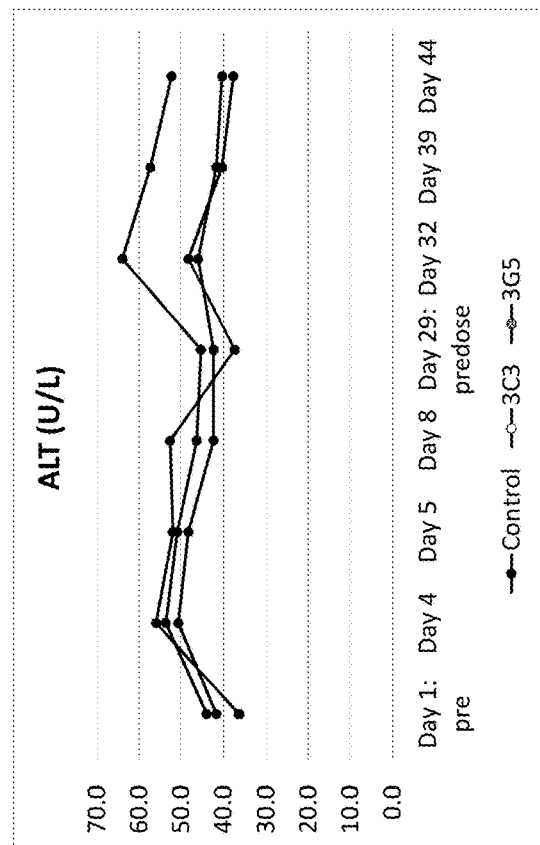
Figure 25B:
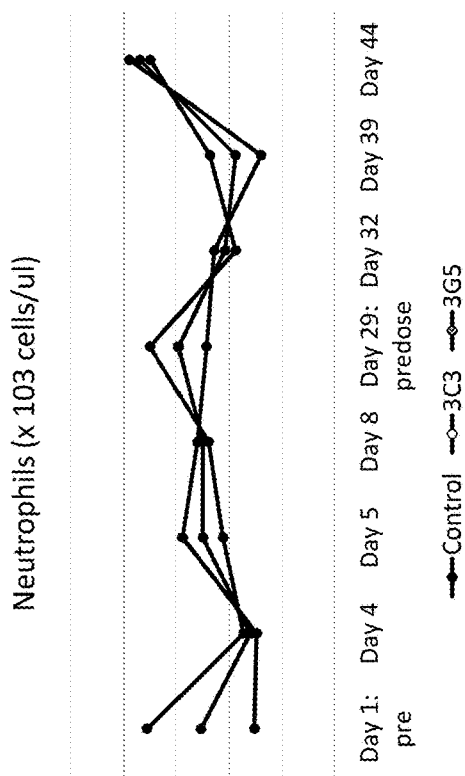
FIGS. 25A-25C are graphs showing amounts of white blood cells (25A), neutrophils (25B) and lymphocytes (25C) measured in monkeys before and after treatment with CD40 antibodies 3C3 or 3G5 at indicated time points.
Figure 25A:
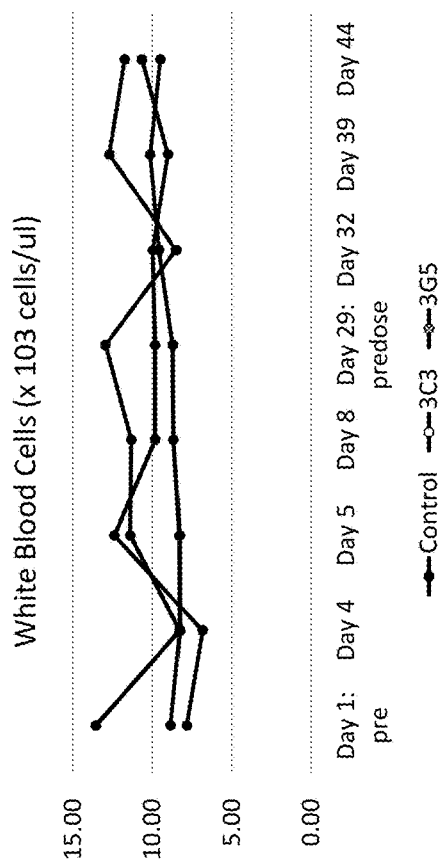
Figure 25C:
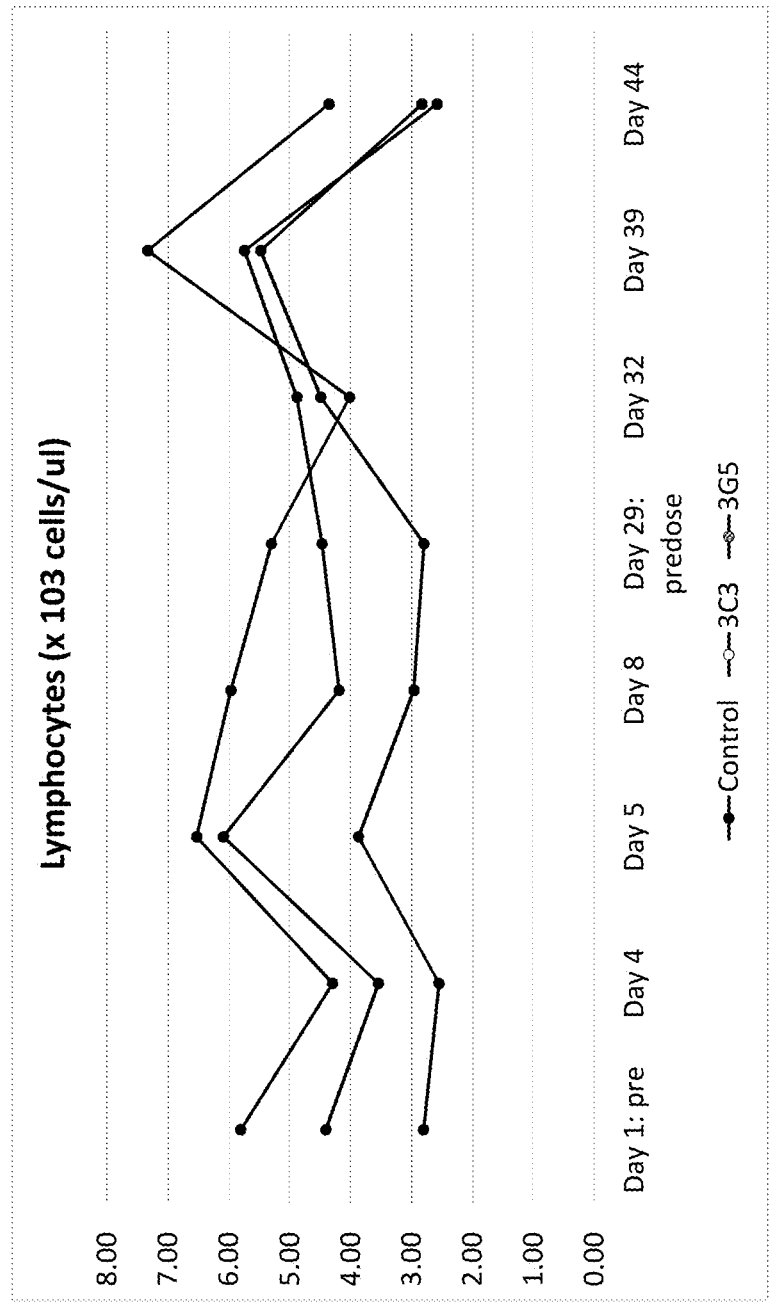
Figure 26:
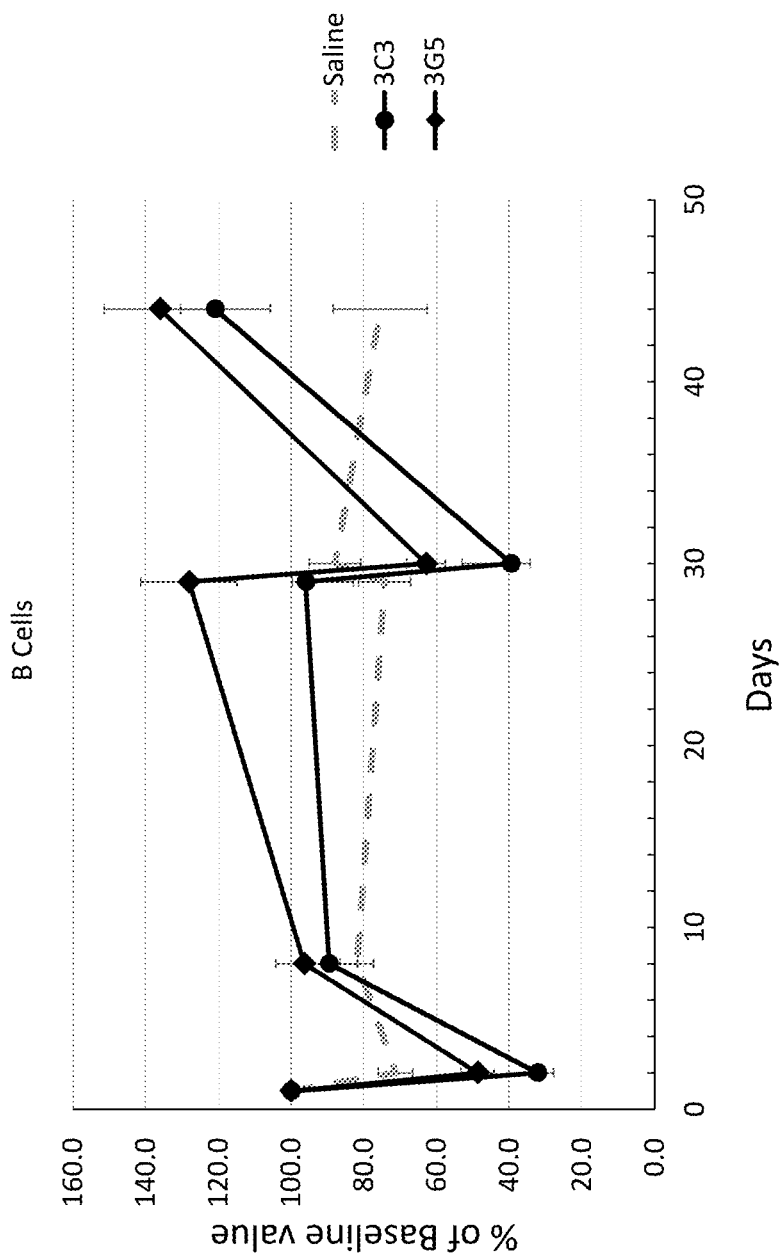
FIG. 26 is a graph showing the percentage change from baseline of amount of B cells in monkeys treated with CD40 antibodies 3C3 or 3G5 over time (days).
Figure 27:
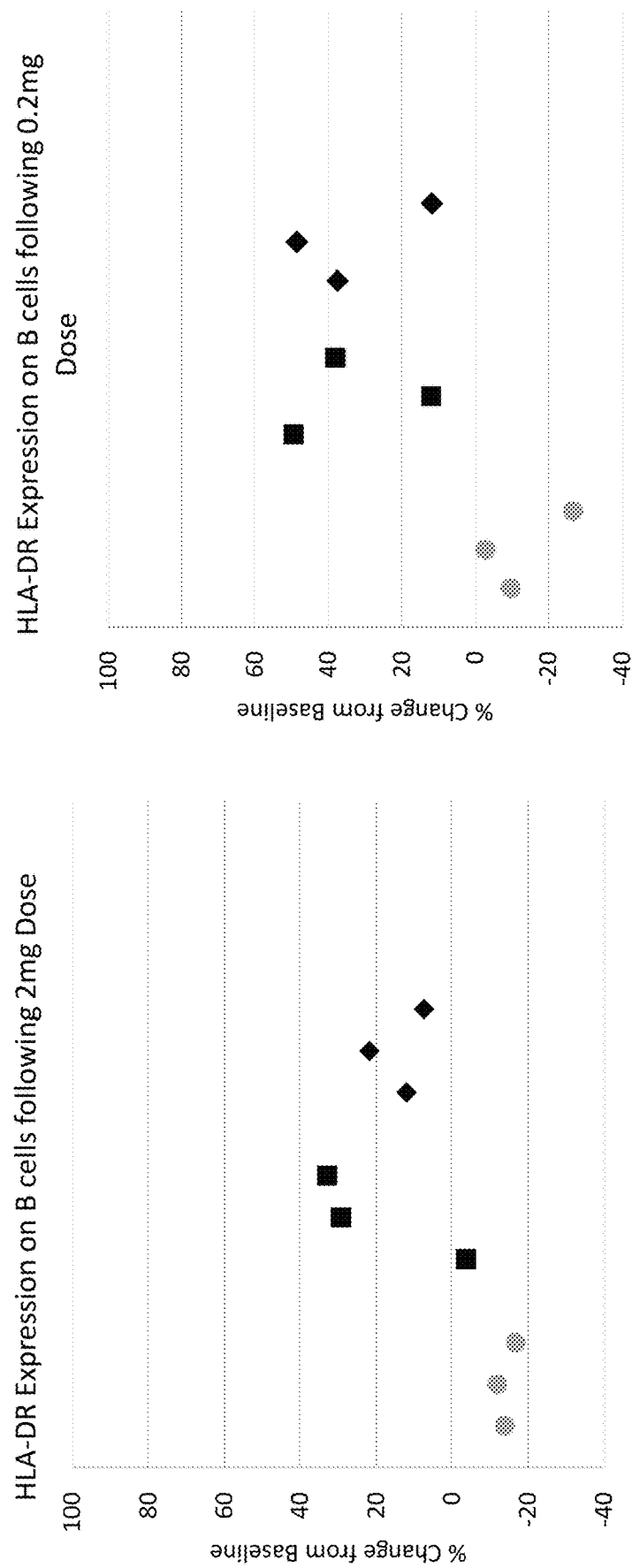
FIG. 27 provides graphs showing HLA-DR expression on B cells relative to baseline following 2 mg (left) or 0.2 mg (right) of CD40 antibody 3C3 (square), 3G5 (diamonds) or saline (circles).

Administration of 3C3 or 3G5 in this study was well tolerated in cynomolgus monkeys without any toxicity parameter being significantly outside of control levels. Of note was the minimal elevations of separate aminotransferase (AST), alanine aminotransferase (ALT) and creatinine kinase in monkeys dosed with 3C3 (FIGS. 23A-23C). Pharmacologic decreases in IL-12 (FIG. 24) white blood cells (FIG. 25A), neutrophils (FIG. 25B) and lymphocytes (FIG. 25C), were seen in both anti-CD40 dosed animals, with most significantly a transient decrease in B cells (FIGS. 26 and 27). In conclusion, 3C3 and 3G5 under the conditions of this showed minimal evidence of toxicity.

Example 19

B Cell Proliferation Independent of Fc Interaction

Figure 28:
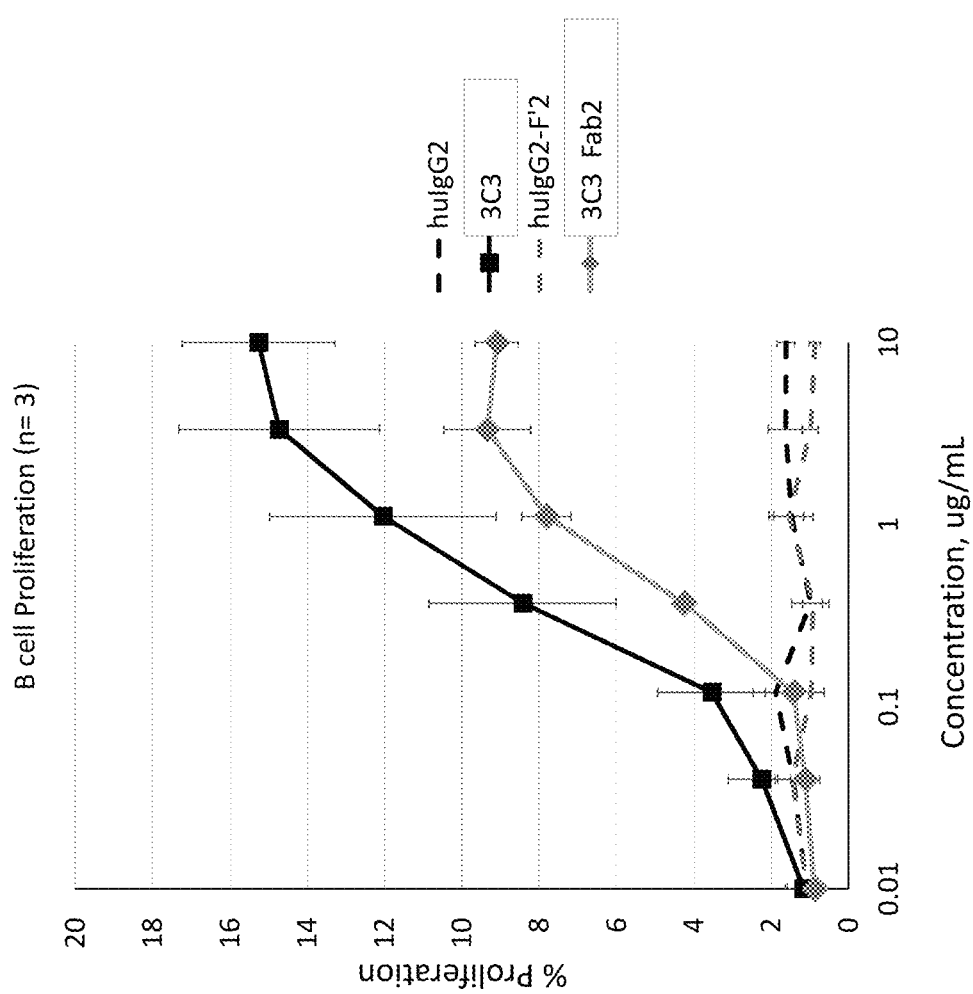
FIG. 28 provides a graph showing B-cell proliferation when cells were cultured in the presence of either the anti-CD40 mAb 3C3.

Human B cells were isolated from peripheral blood mononuclear cells by magnetic selection using CD19 beads. The cells were labeled with 0.5 uM carboxyfluorescein succinimidyl ester (CFSE) at room temperature while rotating for 5 minutes. The labeled cells were cultured in the presence of either the anti-CD40 mAb 3C3 or an isotype control (both whole IgG and F(ab')2 fragments) for 6 days. Cells were then harvested and analyzed by flow cytometry for proliferation. The results are shown in FIG. 28 and indicate that binding to the Fc receptor is not required for CD40 mediated proliferation with 3C3 because intact antibodies with Fc domains and their corresponding F(ab)'2 versions lacking Fc domains are both able to induce proliferation of B cells.

Example 20

Synergy with CD40L in Human B Cells

Figure 29:
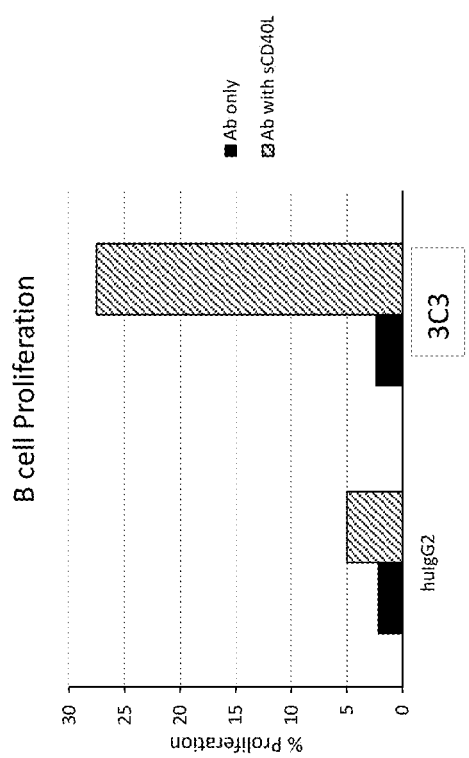
FIGS. 29 and 30 provide graphs showing synergistic effects of the combination of the anti-CD40 mAb 3C3 and CD40L in B-cells.

Human B cells were isolated and labeled as in Example 19. The anti-CD40 mAb 3C3 or an isotype control at 0.1 ug/mL were incubated with the cells for 6 days in the presence or absence of 0.1 ug/mL soluble CD40L (Immunex®). FIG. 29 shows that no significant proliferation is observed with either the 3C3 alone or the isotype control antibody combined with CD40L, however proliferation is induced when CD40L is combined with 3C3 in the culture.

Figure 30:
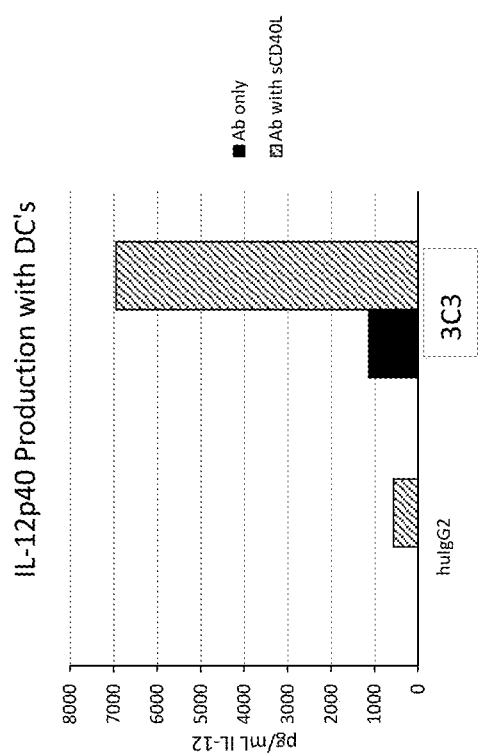

Dendritic cells were prepared and cultured with 0.5 ug/mL of 3C3 as in Example 7 either with or without 0.1 ug/mL soluble CD40L added. IL-12p40 production was measured by ELISA (R&D Systems). FIG. 30 shows that relative to the low level of production by 3C3 alone or the isotype control with CD40L, the combination of 3C3 and CD40L induced higher levels of IL-12p40.

Example 21

Cytokine Response in Whole Blood

Whole blood was incubated overnight with 10 ug/mL isotype control or 3C3, or LPS as a positive control. Next day, the plasma was collected and cytokines measured by ELISA (R&D Systems). The results are shown in FIG. 31 and indicate no significant production of inflammatory cytokines.

EQUIVALENTS

Those skilled in the art will recognize, or be able to ascertain using no more than routine experimentation, many equivalents of the specific embodiments of the invention described herein. Such equivalents are intended to be encompassed by the following claims.

SUMMARY OF SEQUENCE LISTING

| SEQ ID NO: | DESCRIPTION |
|---|---|
| 1 | Human CD40 (GenBank Accession No.: P25942)<br>MVRLPLQCVL WGCLLTAVHP EPPTACREKQ YLINSQCCSL CQPGQKLVSD CTEFTETECL<br>PCGESEFLDT WNRETHCHQH KYCDPNLGLR VQQKGTSETD TICTCEEGWH CTSEACESCV<br>LHRSCSPGFG VKQIATGVSD TICEPCPVGF FSNVSSAFEK CHPWTSCETK DLVVQQAGTN<br>KTDVVCGPQD RLRALVVIPI IFGILFAILL VLVFIKKVAK KPTNKAPHPK QEPQEINFPD<br>DLPGSNTAAP VQETLHGCQP VTQEDGKESR ISVQERQ |
| 2 | Human CD40L (GenBank Accession No.: NP_000065)<br>MIETYNQTSP RSAATGLPIS MKIFMYLLTV FLITQMIGSA LFAVYLHRRL DKIEDERNLH<br>EDFVFMKTIQ RCNTGERSLS LLNCEEIKSQ FEGFVKDIML NKEETKKENS FEMQKGDQNP<br>QIAAHVISEA SSKTTSVLQW AEKGYYTMSN NLVTLENGKQ LTVKRQGLYY IYAQVTFCSN<br>REASSQAPFI ASLCLKSPGR FERILLRAAN THSSAKPCGQ QSIHLGGVFE LQPGASVFVN<br>VTDPSQVSHG TGFTSFGLLK |
| 3 | 3G5-VH<br>QVQLVESGGGVVQPGKSLRLSCAASGFTFSSNGIHWVRQAPGKGLEWVAVIWSDGSNKFYADSVK<br>GRFTISRDNSKNTLYLQMNSLRAEDTAVYYCARASGSGSYYNFFDWGQGTLVTSS |
| 4 | 3G5-VL<br>EIVMTQSPATLSVSPGERATLSCRASQSVRSNLAWYQQKPGQAPRLLIYGASTRATGIPARFSGS<br>GSGTEFTLTINSLQSEDFAVYYCQQHNKWITFGQGTRLEIK |
| 5 | 3G5-VH CDR1 (KABAT)<br>SNGIH |
| 6 | 3G5-VH CDR1 (CHOTHIA)<br>GFTFSSN |
| 7 | 3G5-VH CDR2 (KABAT)<br>VIWSDGSNKFYADSVKG |
| 8 | 3G5-VH CDR2 (CHOTHIA)<br>WSDGSN |
| 9 | 3G5-VH CDR3 (KABAT)<br>ASGSGSYYNFFDY |
| 10 | 3G5-VH CDR3 (CHOTHIA)<br>ASGSGSYYNFFDY |
| 11 | 3G5-VL CDR1 (KABAT)<br>RASQSVRSNLA |
| 12 | 3G5-VL CDR1 (CHOTHIA)<br>RASQSVRSNLA |
| 13 | 3G5-VL CDR2 (KABAT)<br>GASTRAT |
| 14 | 3G5-VL CDR2 (CHOTHIA)<br>GASTRAT |
| 15 | 3G5-VL CDR3 (KABAT)<br>QQHNKWIT |
| 16 | 3G5-VL CDR3 (CHOTHIA)<br>QQHNKWIT |
| 17 | 3C3-VH<br>QVQLVESGGGVVQPGRSLRLSCAGSGFIFSRYGMYWVRQAPGKGLEWVAVIWYDGSYKYYADSVK<br>GRFTISRDNSKNTLYLQMNSLRAEDTAVYYCARESPWYYFDYWGQGTLVTSS |
| 18 | 3C3-VL<br>DIQMTQSPSSLSASVGDRVTITCRASQGISNYLAWYQQKPGKVPKLLIYAASTLQSGVPSRFSGS<br>GSGTDFTLTISSLQPEDVATYYCQKYKSAPFTFGPGTKVDIK |
| 19 | 3C3-VH CDR1 (KABAT)<br>RYGMY |
| 20 | 3C3-VH CDR1 (CHOTHIA)<br>GFIFSRY |
| 21 | 3C3-VH CDR2 (KABAT)<br>VIWYDGSYKYYADSVKG |
| 22 | 3C3-VH CDR2 (CHOTHIA)<br>WYDGSY |

-continued

```
                      SUMMARY OF SEQUENCE LISTING
SEQ ID NO:DESCRIPTION 23    3C3-VH CDR3 (KABAT)
          ESPWYYFDY 24    3C3-VH CDR3 (CHOTHIA)
          ESPWYYFDY 25    3C3-VL CDR1 (KABAT)
          RASQGISNYLA 26    3C3-VL CDR1 (CHOTHIA)
          RASQGISNYLA 27    3C3-VL CDR2 (KABAT)
          AASTLQS 28    3C3-VL CDR2 (CHOTHIA)
          AASTLQS 29    3C3-VL CDR3 (KABAT)
          QKYKSAPFT 30    3C3-VL CDR3 (CHOTHIA)
          QKYKSAPFT 31    3B6-VH
          EVQLLESGGGLVQPGGSLRLSCAASGFTFSSYAMSWVRQAPGKGLEWVSGITGTGGSTYYADSVK
          GRFTISRDNSKNTLYVQMNSLRAEDTAVYYCAKRAGGSFYYYYGMDVWGQGTTVTVSS 32    3B6-VL
          YLGSNRASGVPDRFNGSGSGTDFTLKISRVEAEDFGVYYCMQALQTPWTFGHGTKVEIK 33    3B6-VH CDR1 (KABAT)
          SYAMS 34    3B6-VH CDR1 (CHOTHIA)
          GFTFSSY 35    3B6-VH CDR2 (KABAT)
          GITGTGGSTYYADSVKG 36    3B6-VH CDR2 (CHOTHIA)
          TGTGGS 37    3B6-VH CDR3 (KABAT)
          RAGGSFYYYYGMDV 38    3B6-VH CDR3 (CHOTHIA)
          RAGGSFYYYYGMDV 39    3B6-VL CDR1 (KABAT)
          RSSQSLLHSTGYNYLD 40    3B6-VL CDR1 (CHOTHIA)
          RSSQSLLHSTGYNYLD 41    3B6-VL CDR2 (KABAT)
          LGSNRAS 42    3B6-VL CDR2 (CHOTHIA)
          LGSNRAS 43    3B6-VL CDR3 (KABAT)
          MQALQTPWT 44    3B6-VL CDR3 (CHOTHIA)
          MQALQTPWT 45    6H6-VH
          QVQLVESGGGVVQPGRSLRFSCAASGFTLSSYGMHWVRQAPGKGLEWVAVIWDDGSNKYYADSVK
          GRFTISRDNSKNTLYLQMNSLRAEDTAVYYCARAGGSGRYYNYFDYWGQGTLVTVSS 46    6H6-VL
          EIVMTQSPATLSVSPGERATLSCRASQSVRSNLAWYQQKPGQAPRLLIYGASTRATGIPARFSGS
          GSGTDFTLTISSLQSEDFAVYYCQQHNNWLTFGGGTKVEIK
```

-continued

| SUMMARY OF SEQUENCE LISTING | |
|---|---|
| SEQ ID NO: | DESCRIPTION |
| 47 | 6H6-VH CDR1 (KABAT)<br>SYGMH |
| 48 | 6H6-VH CDR1 (CHOTHIA)<br>GFTLSSY |
| 49 | 6H6-VH CDR2 (KABAT)<br>VIWDDGSNKYYADSVKG |
| 50 | 6H6-VH CDR2 (CHOTHIA)<br>WDDGSN |
| 51 | 6H6-VH CDR3 (KABAT)<br>AGGSGRYYNYFDY |
| 52 | 6H6-VH CDR3 (CHOTHIA)<br>AGGSGRYYNYFDY |
| 53 | 6H6-VL CDR1 (KABAT)<br>RASQSVRSNLA |
| 54 | 6H6-VL CDR1 (CHOTHIA)<br>RASQSVRSNLA |
| 55 | 6H6-VL CDR2 (KABAT)<br>GASTRAT |
| 56 | 6H6-VL CDR2 (CHOTHIA)<br>GASTRAT |
| 57 | 6H6-VL CDR3 (KABAT)<br>QQHNNWLT |
| 58 | 6H6-VL CDR3 (CHOTHIA)<br>QQHNNWLT |
| 59 | 1B4-VH<br>EVQLLESGGGLVQPGGSLRLSCAASGFTFSSYAMTWVRQVPGKGLEWVSGITGSGANTFYTDSVK<br>GRFTISRDNSNNSLYLQMNSLRADDTAVYYCAKRNGGSYYYYGMDVWGQGTTVTVSS |
| 60 | 1B4-VL<br>DIVMTQSPLSLPVTPGEPASISCRSSQSLLHSSGYNYLDWYLQKPGQSPQLLIYLGSNRASGVPD<br>RFSGSGSGTDFTLKISRVEAEDVGVYYCMQALQIPWTFGQGTKVEIK |
| 61 | 1B4-VH CDR1 (KABAT)<br>SYAMT |
| 62 | 1B4-VH CDR1 (CHOTHIA)<br>GFTFSSY |
| 63 | 1B4-VH CDR2 (KABAT)<br>GITGSGANTFYTDSVKG |
| 64 | 1B4-VH CDR2 (CHOTHIA)<br>TGSGAN |
| 65 | 1B4-VH CDR3 (KABAT)<br>RNGGSYYYYGMDV |
| 66 | 1B4-VH CDR3 (CHOTHIA)<br>RNGGSYYYYGMDV |
| 67 | 1B4-VL CDR1 (KABAT)<br>RSSQSLLHSSGYNYLD |
| 68 | 1B4-VL CDR1 (CHOTHIA)<br>RSSQSLLHSSGYNYLD |
| 69 | 1B4-VL CDR2 (KABAT)<br>LGSNRAS |
| 70 | 1B4-VL CDR2 (CHOTHIA)<br>LGSNRAS |

SUMMARY OF SEQUENCE LISTING

| SEQ ID NO: | DESCRIPTION |
|---|---|
| 71 | 1B4-VL CDR3 (KABAT)<br>MQALQIPWT |
| 72 | 1B4-VL CDR3 (CHOTHIA)<br>MQALQIPWT |
| 73 | 3B6-NS-VH<br>EVQLLESGGGLVQPGGSLRLSCAASGFTFSSYAMSWVRQAPGKGLEWVSGITGTGGSTYYADSVK<br>GRFTISRDNSKNTLYVQMNSLRAEDTAVYYCAKRAGGSFYYYGMDVWGQGTTVTVSS |
| 74 | 3B6-NS-VL<br>DIVMTQSPLSLPVTPGEPASISCRSSQSLLHSTGYNYLDWYLQKPGQSPQLLIYLGSNRASGVPD<br>RFSGSGSGTDFTLKISRVEAEDFGVYYCMQALQTPWTFGHGTKVEIK |
| 75 | 3B6-NS-VH CDR1 (KABAT)<br>SYAMS |
| 76 | 3B6-NS-VH CDR1 (CHOTHIA)<br>GFTFSSY |
| 77 | 3B6-NS-VH CDR2 (KABAT)<br>GITGTGGSTYYADSVKG |
| 78 | 3B6-NS-VH CDR2 (CHOTHIA)<br>TGTGGS |
| 79 | 3B6-NS-VH CDR3 (KABAT)<br>RAGGSFYYYGMDV |
| 80 | 3B6-NS-VH CDR3 (CHOTHIA)<br>RAGGSFYYYGMDV |
| 81 | 3B6-NS-VL CDR1 (KABAT)<br>RSSQSLLHSTGYNYLD |
| 82 | 3B6-NS-VL CDR1 (CHOTHIA)<br>RSSQSLLHSTGYNYLD |
| 83 | 3B6-NS-VL CDR2 (KABAT)<br>LGSNRAS |
| 84 | 3B6-NS-VL CDR2 (CHOTHIA)<br>LGSNRAS |
| 85 | 3B6-NS-VL CDR3 (KABAT)<br>MQALQTPWT |
| 86 | 3B6-NS-VL CDR3 (CHOTHIA)<br>MQALQTPWT |
| 87 | 2E1.2-VH<br>QVQLVESGGGVVQPGRSLRLSCAASGFTFSSYGMHWVRQAPGKGLEWVAVIWDDGSNKYYADSVK<br>GRFTISRDNSKNTLYLQMNSLRAEDTAVYYCARAGSSGRYYNYFDYWGQGTLVTVSS |
| 88 | 2E1.2-VL2<br>EIVMTQSPATLSVSPGERATLSCRASQSVRSNLAWYQQKPGQAPRLLIYGASTRATGIPDRFSGS<br>GSGTEFTLTISSLQSEDFAVYHCQQYNKWLIFGGGTKVEIK |
| 89 | 2E1.2-VH CDR1 (KABAT)<br>SYGMH |
| 90 | 2E1.2-VH CDR1 (CHOTHIA)<br>GFTFSSY |
| 91 | 2E1.2-VH CDR2 (KABAT)<br>VIWDDGSNKYYADSVKG |
| 92 | 2E1.2-VH CDR2 (CHOTHIA)<br>WDDGSN |
| 93 | 2E1.2-VH CDR3 (KABAT)<br>AGSSGRYYNYFDY |
| 94 | 2E1.2-VH CDR3 (CHOTHIA)<br>AGSSGRYYNYFDY |

SUMMARY OF SEQUENCE LISTING

| SEQ ID NO: | DESCRIPTION |
|---|---|
| 95 | 2E1.2-VL2 CDR1 (KABAT)<br>RASQSVRSNLA |
| 96 | 2E1.2-VL2 CDR1 (CHOTHIA)<br>RASQSVRSNLA |
| 97 | 2E1.2-VL2 CDR2 (KABAT)<br>GASTRAT |
| 98 | 2E1.2-VL2 CDR2 (CHOTHIA)<br>GASTRAT |
| 99 | 2E1.2-VL2 CDR3 (KABAT)<br>QQYNKWLI |
| 100 | 2E1.2-VL2 CDR3 (CHOTHIA)<br>QQYNKWLI |
| 101 | 1B5-NK-VH<br>QVQLVESGGGVVQPGRSLRLSCAASGFTFSSFGMEIWVRQAPGKGLEWVTLAVAGWYFDFWGRGT<br>LVTVSS |
| 102 | 1B5-NK-VL<br>DIQMTQSPSSLSASVGDRVTITCRASQGVRKYLAWYQQKPGKVPKLLIYAASTLQSGVPSRFSGS<br>GSGTDFTLTISSLQPEDVATYYCQKYFSAPYTFGQGTKLEIK |
| 103 | 1B5-NK-VH CDR1 (KABAT)<br>SFGMH |
| 104 | 1B5-NK-VH CDR1 (CHOTHIA)<br>GFTFSSF |
| 105 | 1B5-NK-VH CDR2 (KABAT)<br>LIWFDGSSKYYADSVKG |
| 106 | 1B5-NK-VH CDR2 (CHOTHIA)<br>WFDGSS |
| 107 | 1B5-NK-VH CDR3 (KABAT)<br>GFAAVAGWYFDF |
| 108 | 1B5-NK-VH CDR3 (CHOTHIA)<br>GFAAVAGWYFDF |
| 109 | 1B5-NK-VL CDR1 (KABAT)<br>RASQGVRKYLA |
| 110 | 1B5-NK-VL CDR1 (CHOTHIA)<br>RASQGVRKYLA |
| 111 | 1B5-NK-VL CDR2 (KABAT)<br>AASTLQS |
| 112 | 1B5-NK-VL CDR2 (CHOTHIA)<br>AASTLQS |
| 113 | 1B5-NK-VL CDR3 (KABAT)<br>QKYFSAPYT |
| 114 | 1B5-NK-VL CDR3 (CHOTHIA)<br>QKYFSAPYT |
| 115 | 3G5 VH with leader sequence underlined<br><u>Atggagtttgggctgacctggttttcctcgttgctcttttaagaggtgtccagtgt</u>caggtgca<br>gttggtggaatctGggggaggcgtggtccagcctggggaagtccctgagactctcctgtgcagcgt<br>ctggattcaccttcagtagcaatgGcattcactgggtccgccaggctccaggcaaggggctggag<br>tgggtggcagttatctggtctgatggaagtaataaAttctatgcagactccgtgaagggccgatt<br>caccatctccagagacaattccaagaacacgctatatctgcaaatgaAcagcctgagagccgagg<br>acacggctgtatattactgtgcgagagcctctggttcggggagttattataacttctttgactac<br>tggggccagggaaccctggtcaccgtctcctca |
| 116 | 3G5 VL with leader sequence underline<br><u>Atggaagccccagcgcagcttctcttcctcctgctactctggctcccagatagcactggagaaat</u><br>agtgatgacgcagTctccagccaccctgtctgtgtctccaggggaaagagccaccctctcctgca |

SUMMARY OF SEQUENCE LISTING

| SEQ ID NO: | DESCRIPTION |
|---|---|
| | gggccagtcagagtgttagaagtaacTtagcctggtaccagcagaaacctggccaggctcccagg<br>ctcctcatctatggtgcatccaccagggccactggtatccCagccaggttcagtggcagtgggtc<br>tgggacagagttcactctcaccatcaacagcctgcagtctgaagattttgcagtttattactgtc<br>agcagcataataagtggatcaccttcggccaagggacacgactggagattaaa |
| 117 | 3C3 VH with leader sequence underlined<br><u>Atggagtttgggctgagctgggttttccttcgttgctcttttt</u>aagaggtgtccagtgtcaggtgca<br>gctggtggagtctggGggaggcgtggtccagcctggaggtccctgagactctcctgtgcagggt<br>ctggattcatttttcagtcgctatggcatgTactgggtccgccaggctccaggcaaggggctggag<br>tgggtggcagttatatggtatgatggaagttataaatactatGcagactccgtgaagggccgatt<br>caccatctccagagacaattccaagaacacgctgtatctgcaaatgaacagcctgAgagccgagg<br>acacggctgtgtattactgtgcgagagaatcaccatggtactactttgactactggggccaggga<br>accctggtcaccgtctcctct |
| 118 | 3C3 VL with leader sequence underlined<br><u>Atggacatgagggtccctgctcagctcctggggactcctgctgctctggctcccagataccagatg</u><br><u>t</u>gacatccagatgacCcagtctccatcctccctgtctgcatctgtaggagacagagtcaccatca<br>cttgccgggcgagtcagggcattagcaattaTttagcctggtatcagcagaaaccagggaaagtt<br>cctaagctcctgatctatgctgcatccactttgcaatcagggtgtcccAtctcggttcagtggcag<br>tggatctgggacagatttcactctcaccatcagcagcctgcagcctgaagatgttgcaacttatt<br>actgtcaaaagtataagagtgccccattcactttcggccctgggaccaaagtggatatcaaa |
| 119 | 3B6 VH with leader sequence underlined<br><u>Atggagtttgggctgagctggcttttcttgtggctatttt</u>aaaaggtgtccagtgtgaggtgca<br>gctgttggagtctggggGaggcttggtacagcctggggggtccctgagactctcctgtgcagcct<br>ctggattcaccctttagcagctatgccatgagctGggtccgccaggctccagggaaggggccggtt<br>tgggtctcaggtataactggtactggtggtagcacatactacgcagActccgtgaagggccggtt<br>caccatctccagagacaattccaagaacacgctgtatgtgcaaatgaacagcctgagagcCgagg<br>acacggccgtatattactgtgcgaaaagggctggtgggagcttctactactactacggtatggac<br>gtctggggccaagggaccacggtcaccgtctcctca |
| 120 | 3B6 VL with leader sequence underlined<br><u>Atgaggctccctgctcagctcctggggctgctaatgctctggtctctgg</u>atccagtggggatat<br>tgtgatgactcagtctcCactctccctgcccgtcacccctggagagccggcctccatctcctgca<br>ggtctagtcagagcctcctgcatagtactggataCaactatttggattggtacctgcagaagcca<br>gggcagtctccacagctcctgatctatttgggttctaatcgggcctccgggGtccctgacaggtt<br>caatggcagtggatcaggcacagattttacactgaaaatcagcagagtggaggctgaggattttg<br>gggtttattactgcatgcaagctctacaaactccgtggacgttcggccacgggaccaaggtggaa<br>atcaaa |
| 121 | 6H6 VH with leader sequence underlined<br><u>Atggagtttgggctgagctgggtattccttcgttgctcttttt</u>aagaggtgtccagtgtcaggtgca<br>gctggtggagtctggggGaggcgtggtccagcctggaggtccctgagattctcctgtgcagggt<br>ctggattcacccctcagtagctatggcatgcactgGgtccgccaggctccaggcaaggggctggag<br>tgggtggcagttatatgggatgatggaagtaataaatactatgcagactCcgtgaagggccgatt<br>caccatctccagagacaattccaagaacacgctgtatctgcaaatgaacagcctgagagccgagg<br>Acacggctgtctattactgtgcgagagcggggggttcggggaggtattataactactttgactac<br>tggggccagggaaccctggtcaccgtctcctca |
| 122 | 6H6 VL with leader sequence underlined<br><u>Atggaagcccccagcgcagcttctcttcctcctgctactctggctcccagataccactggagaaat</u><br>agtgatgacgcagtctccAgccaccctgtctgtgtctccaggggaaagagccaccctctcctgca<br>gggccagtcagagtgttagaagcaacttagcctggTaccagcagaaacctggccaggctcccagg<br>ctcctcatctatggtgcatccaccagggccactggtatcccagccaggttcagTggcagtgggtc<br>tgggacagacttcactctcaccatcagcagcctgcagtctgaagattttgcagtttattactgtc<br>agcagcaTaataactggctcactttcggcggagggaccaaggtggagatcaaa |
| 123 | 1B4 VH with leader sequence underlined<br><u>Atggagtttgggctgagctggcttttcttgtggctatttt</u>aaaaggtgtccaatgtgaggtgca<br>gctgttggaatctggggGaGgcttggtacagcctggggggtccctgagactctcctgtgcggcct<br>ctggggttcacctttagcagctatgccatgacctgggtcCgccaggttccagggaaggggcctggag<br>tgggtctcaggtattactggtagtggtgctaacacattctacacagactccgtgaAgggccggtt<br>caccatttccagagacaattccaataattcgctgtatctgcaaatgaacagcctgagagccgatg<br>acacggcCgtatactactgtgcgaaaagaaatggtgggagttactactactacggcatggac<br>gtctggggccaagggaccacggtcaccgtgtcctca |
| 124 | 1B4 VL with leader sequence underlined<br><u>Atgaggctccctgctcagctcctggggctgctaatgctctggtctctgg</u>atccagtggggatat<br>tgtgatgactcagtctccacTctccctgcccgtcacccctggagagccggcctccatctcctgca<br>ggtcaagtcagagcctcctgcatagtagtggatacaactaTttggattggtacctgcagaagcca<br>gggcagtctccacaactcctgatctatttgggttctaatcgggcctccggggtccctgacAggtt<br>cagtggcagtggatcaggcacagattttacactgaaaatcagcagagtggaggctgaggatgttg<br>gggtttattactgcatgcaagctctacaaattccgtggacgttcggccaagggaccaaggtggaa<br>atcaaa |

SUMMARY OF SEQUENCE LISTING

| SEQ ID NO: | DESCRIPTION |
|---|---|
| 125 | 2E1.2 VH with leader sequence underlined<br>Atggagtttgggctgagctgggttttccttcgttgctcttttaagaggtgtccagtgtcaggtgca<br>gctggtggagtctggggggaggcgtggtCcagcctggggaggtccctgagactctcctgtgcagcgt<br>ctggattcaccttcagtagctatggcatgcactgggtccgccaggctccaggcAggggctggag<br>tgggtggcagttatatgggatgatggaagtaataaatactatgcagactccgtgaagggccgatt<br>caccatctcccagagAcaattccaagaacacgctgtatctgcaaatgaacagcctgagagccgagg<br>acacggctgtgtattactgtgcgagagcgggaagttcggggaggtattataactactttgactac<br>tggggccagggaaccctggtcaccgtctcctca |
| 126 | 2E1.2 VL2 with leader sequence underlined<br>Atggaagccccagcgcagcttctcttcctcctgctactctggctcccagataccactggagaaat<br>agtgatgacgcagtctccagccaccctgtctgtgtctccaggggaaagagccaccctctcctgca<br>gggccagtcagagtgttaggagcaacttagcctggtatcagcagaaacctggccaggctcccagg<br>ctcctcatctatggtgcatccaccagggccactgtatcccagacaggttcagtggcagtgggtc<br>tgggacagagttcactctcaccatcagcagcctgcagtctgaagattttgcagtttatcactgtc<br>agcagtataataagtggctcatttcggcggagggaccaaggtggagatcaaa |
| 127 | 1B5 VH with leader sequence underlined<br>Atggagtttgggctgagctgggttttccttcgttgctcttttaagaggtgtccagtgtcaggtgca<br>gctggtggagtctggggggaggcgtggtccagcCtggggaggtccctgagactctcctgtgcagcgt<br>ctggattcaccttcagtagctttggcatgcactgggtccgccaggctccaggcaaggggctggaG<br>tgggtgacacttatatggtttgatggaagttctaaatactatgcagactccgtgaagggccgatt<br>caccatctcccagagacaactccaacaacacGctgtatctgcaaatgaacagcctgagagccgagg<br>acacggctgtatattactgtgtgagaggttttgcagcagtggctgggtggtacttcgatttctgg<br>ggccgtggcaccctggtcactgtctcctca |
| 128 | 1B5 VL with leader sequence underlined<br>Atggacatgagggtccctgctcagctcctgggactcctgctgctctggctcccagataccagatg<br>tgacatccagatgacccagtctccatcctcccTgtctgcatctgtaggagacagagtcaccatca<br>cttgccgggcgagtcagggcgttagaaagtatttagcctggtatcagcagaaaccagggaaAgtt<br>cctaagctcctgatctatgctgcatccactttgcaatcaggggtcccatctcggttcagtggcag<br>tggatctgggacagatttcactctcaccaTcagcagcctgcagcctgaagatgttgcaacttatt<br>actgtcaaaagtatttcagtgcccgtacactttggccaggggaccaaactggagatcaaa |
| 129 | 3B6-NS VH with leader sequence underlined<br>Atggagtttgggctgagctggcttttttcttgtggctattttaaaggtgtccagtgtgaggtgca<br>gctgttggagtctggggggaggcttggtacagcctggggggtccctgagactctcctgtgcagcct<br>ctggattcacctttagcagctatgccatgagctgggtccgccaggctccagggaaggggctggag<br>tgggtctcaggtataactggtactggtggtagcacatactacgcagactccgtgaagggccgatt<br>caccatctcccagagacaattccaagaacacgctgtatgtgcaaatgaacagcctgagagccgagg<br>acacggccgtatattactgtgcgaaaagggctggtgggagcttctactactactacggtatggac<br>gtctggggccaagggaccacggtcaccgtctcctca |
| 130 | 3B6-NS VL with leader sequence underlined<br>atgaggctccctgctcagctcctggggctgctaatgctctgggtctctggatccagtggggatat<br>tgtgatgactcagtctccactctccctgcccgtcacccctggagagccggcctccatctcctgca<br>ggtctagtcagagcctcctgcatagtactggatacaactatttggattggtacctgcagaagcca<br>gggcagtctccacagctcctgatctatttgggttctaatcggcctccgggggtccctgacaggtt<br>cagtggcagtggatcaggcacagatttttacactgaaaatcagcagagtggaggctgaggattttg<br>gggtttattactgcatgcaagctctacaaactccgtggacgttcggccacgggaccaaggtggaa<br>atcaaa |
| 131 | 1B5-NK VH with leader sequence underlined<br>atggagtttgggctgagctgggttttccttcgttgctcttttaagaggtgtccagtgtcaggtgca<br>gctggtggagtctggggggaggcgtggtccagcctggggaggtccctgagactctcctgtgcagcgt<br>ctggattcaccttcagtagctttggcatgcactgggtccgccaggctccaggcaaggggctggag<br>tgggtgacacttatatggtttgatggaagttctaaatactatgcagactccgtgaagggccgatt<br>caccatctcccagagacaactccaagaacacgctgtatctgcaaatgaacagcctgagagccgagg<br>acacggctgtatattactgtgtgagaggttttgcagcagtggctgggtggtacttcgatttctgg<br>ggccgtggcaccctggtcactgtctcctca |
| 132 | 1B5-NK VL with leader sequence underlined<br>Atggacatgagggtccctgctcagctcctgggactcctgctgctctggctcccagataccagatg<br>tgacatccagatgacccagtctccatcctccctgtctgcatctgtaggagacagagtcaccatca<br>cttgccgggcgagtcagggcgttagaaagtatttagcctggtatcagcagaaaccagggaaagtt<br>cctaagctcctgatctatgctgcatccactttgcaatcaggggtcccatctcggttcagtggcag<br>tggatctgggacagatttcactctcaccatcagcagcctgcagcctgaagatgttgcaacttatt<br>actgtcaaaagtatttcagtgcccgtacactttggccaggggaccaaactggagatcaaa |
| 133 | Human CD40 Extracellular Domain<br>EPPTACREKQYLINSQCCSLCQPGQKLVSDCTEFTETECLPCGESEFLDTWNRETHCHQHKYCDP<br>NLGLRVQQKGTSETDTICTCEEGWHCTSEACESCVLHRSCSPGFGVKQIATGVSDTICEPCPVGF<br>FSNVSSAFEKCHPWTSCETKDLVVQQAGTNKTDVVCGPQDRLR |

SUMMARY OF SEQUENCE LISTING

| SEQ ID NO: | DESCRIPTION |
|---|---|
| 134 | Immunoglobulin heavy constant gamma 2 (IgHG2) (Uniprot P01859)<br>ASTKGPSVFPLAPCSRSTSESTAALGCLVKDYFPEPVTVSWNSGALTSGVHTFPAVLQSSGLYSL<br>SSVVTVPSSNFGTQTYTCNVDHKPSNTKVDKTVERKCCVECPPCPAPPVAGPSVFLFPPKPKDTL<br>MISRTPEVTCVVVDVSHEDPEVQFNWYVDGVEVHNAKTKPREEQFNSTFRVVSVLTVVHQDWLNG<br>KEYKCKVSNKGLPAPIEKTISKTKGQPREPQVYTLPPSREEMTKNQVSLTCLVKGFYPSDISVEW<br>ESNGQPENNYKTTPPMLDSDGSFFLYSKLTVDKSRWQQGNVFSCSVMHEALHNHYTQKSLSLSPG<br>K |
| 135 | 3C3 heavy chain with variable region in italics and constant domain in bold<br>*QVQLVESGGGVVQPGRSLRLSCAGSGFIFSRYGMYWVRQAPGKGLEWVAVIWYDGSYKYYADSVK<br>GRFTISRDNSKNTLYLQMNSLRAEDTAVYYCARESPWYYDFYWGQGTLVTVSS*ASTKGPSVFPLA<br>PCSRSTSESTAALGCLVKDYFPEPVTVSWNSGALTSGVHTFPAVLQSSGLYSLSSVVTVPSSNFG<br>TQTYTCNVDHKPSNTKVDKTVERKCCVECPPCPAPPVAGPSVFLFPPKPKDTLMISRTPEVTCVV<br>VDVSHEDPEVQFNWYVDGVEVHNAKTKPREEQFNSTFRVVSVLTVVHQDWLNGKEYKCKVSNKGL<br>PAPIEKTISKTKGQPREPQVYTLPPSREEMTKNQVSLTCLVKGFYPSDIAVEWESNGQPENNYKT<br>TPPMLDSDGSFFLYSKLTVDKSRWQQGNVFSCSVMHEALHNHYTQKSLSLPG |
| 136 | 3C3 light chain with variable region in italics and constant domain in bold<br>*DIQMTQSPSSLSASVGDRVTITCRASQGISNYLAWYQQKPGKVPKLLIYAASTLQSGVPSRFSGS<br>GSGTDFTLTISSLQPEDVATYYCQKYKSAPFTFGPGTKVDIK*RTVAAPSVFIFPPSDEQLKSGTA<br>SVVCLLNNFYPREAKVQWKVDNALQSGNSQESVTEQDSKDSTYSLSSTLTLSKADYEKHKVYACE<br>VTHQGLSSPVTKSFNRGEC |
| 137 | 3C3 heavy chain with leader sequence underlined, variable region in italics and constant domain in bold<br><u>MEFGLSWVFLVALLRGVQC</u>*QVQLVESGGGVVQPGRSLRLSCAGSGFIFSRYGMYWVRQAPGKGLE<br>WVAVIWYDGSYKYYADSVKGRFTISRDNSKNTLYLQMNSLRAEDTAVYYCARESPWYYDFYWGQG<br>TLVTVSS*ASTKGPSVFPLAPCSRSTSESTAALGCLVKDYFPEPVTVSWNSGALTSGVHTFPAVLQ<br>SSGLYSLSSVVTVPSSNFGTQTYTCNVDHKPSNTKVDKTVERKCCVECPPCPAPPVAGPSVFLFP<br>PKPKDTLMISRTPEVTCVVVDVSHEDPEVQFNWYVDGVEVHNAKTKPREEQFNSTFRVVSVLTVV<br>HQDWLNGKEYKCKVSNKGLPAPIEKTISKTKGQPREPQVYTLPPSREEMTKNQVSLTCLVKGFYP<br>SDIAVEWESNGQPENNYKTTPPMLDSDGSFFLYSKLTVDKSRWQQGNVFSCSVMHEALHNHYTQK<br>SLSLSPG |
| 138 | 3C3 light chain with leader sequence underlined, variable region in italics and constant domain in bold<br><u>MGWSCIILFLVATATGVHS</u>*DIQMTQSPSSLSASVGDRVTITCRASQGISNYLAWYQQKPGKVPKL<br>LIYAASTLQSGVPSRFSGSGSGTDFTLTISSLQPEDVATYYCQKYKSAPFTFGPGTKVDIK*RTVA<br>APSVFIFPPSDEQLKSGTASVVCLLNNFYPREAKVQWKVDNALQSGNSQESVTEQDSKDSTYSLS<br>STLTLSKADYEKHKVYACEVTHQGLSSPVTKSFNRGEC |

---

The invention claimed is:

1. An isolated nucleic acid encoding the variable region of a light chain, heavy chain, or both light and heavy chains of an antibody which binds to human CD40, wherein the heavy and/or light chain variable regions comprise the amino acid sequence set forth in SEQ ID NOs: 17 and 18, respectively.

2. An expression vector comprising the nucleic acid of claim 1.

3. A cell transformed with an expression vector of claim 2.

4. An isolated nucleic acid encoding the variable region of a light chain, heavy chain, or both light and heavy chains of an antibody which binds to human CD40, wherein the heavy and/or light chain variable regions comprise the CDR sequences from the heavy and/or light chain variable regions comprising the amino acid sequences set forth in SEQ ID NOs: 17 and 18, respectively.

5. An expression vector comprising the nucleic acid of claim 4.

6. A cell transformed with an expression vector of claim 5.

7. An isolated nucleic acid encoding the variable region of a light chain, heavy chain, or both light and heavy chains of an antibody which binds to human CD40, wherein the heavy chain variable region comprises the CDR1, CDR2, and CDR3 sequences set forth in SEQ ID NOs: 19, 21, and 23, respectively, and the light chain variable region comprises the CDR1, CDR2, and CDR3 sequences set forth in SEQ ID NOs: 25, 27, and 29, respectively.

8. An expression vector comprising the nucleic acid of claim 7.

9. A cell transformed with an expression vector of claim 8.

10. A method of producing an antibody comprising culturing the cell of claim 3, wherein the antibody is produced.

11. A method of producing an antibody comprising culturing the cell of claim 6, wherein the antibody is produced.

* * * * *

SEQUENCE LISTING

<160> NUMBER OF SEQ ID NOS: 147

<210> SEQ ID NO 1
<211> LENGTH: 277
<212> TYPE: PRT
<213> ORGANISM: Homo sapiens
<220> FEATURE:
<221> NAME/KEY: misc_feature
<223> OTHER INFORMATION: Human CD40

<400> SEQUENCE: 1

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

```
Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
            130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Val Ala Lys Lys Pro Thr Asn
            210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
            245                 250                 255

Gly Cys Gln Pro Val Thr Gln Glu Asp Gly Lys Glu Ser Arg Ile Ser
            260                 265                 270

Val Gln Glu Arg Gln
            275

<210> SEQ ID NO 2
<211> LENGTH: 260
<212> TYPE: PRT
<213> ORGANISM: Homo sapiens
<220> FEATURE:
<221> NAME/KEY: misc_feature
<223> OTHER INFORMATION: Human CD40L

<400> SEQUENCE: 2

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
            50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
            130                 135                 140

Tyr Tyr Thr Met Ser Asn Asn Leu Val Thr Leu Glu Asn Gly Lys Gln
```

```
                145                 150                 155                 160
Leu Thr Val Lys Arg Gln Gly Leu Tyr Tyr Ile Tyr Ala Gln Val Thr
                    165                 170                 175

Phe Cys Ser Asn Arg Glu Ala Ser Ser Gln Ala Pro Phe Ile Ala Ser
                    180                 185                 190

Leu Cys Leu Lys Ser Pro Gly Arg Phe Glu Arg Ile Leu Leu Arg Ala
                    195                 200                 205

Ala Asn Thr His Ser Ser Ala Lys Pro Cys Gly Gln Gln Ser Ile His
                    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                    245                 250                 255

Gly Leu Leu Lys
            260

<210> SEQ ID NO 3
<211> LENGTH: 122
<212> TYPE: PRT
<213> ORGANISM: Artificial Sequence
<220> FEATURE:
<223> OTHER INFORMATION: Synthetic: 3G5 VH

<400> SEQUENCE: 3

Gln Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Ser Ser Asn
                20                  25                  30

Gly Ile His Trp Val Arg Gln Ala Pro Gly Lys Gly Leu Glu Trp Val
            35                  40                  45

Ala Val Ile Trp Ser Asp Gly Ser Asn Lys Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ser Gly Ser Gly Ser Tyr Tyr Asn Phe Phe Asp Tyr Trp
            100                 105                 110

Gly Gln Gly Thr Leu Val Thr Val Ser Ser
        115                 120

<210> SEQ ID NO 4
<211> LENGTH: 106
<212> TYPE: PRT
<213> ORGANISM: Artificial Sequence
<220> FEATURE:
<223> OTHER INFORMATION: Synthetic: 3G5 VL

<400> SEQUENCE: 4

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60
```

Ser Gly Ser Gly Thr Glu Phe Thr Leu Thr Ile Asn Ser Leu Gln Ser
 65                  70                  75                  80

Glu Asp Phe Ala Val Tyr Tyr Cys Gln Gln His Asn Lys Trp Ile Thr
                 85                  90                  95

Phe Gly Gln Gly Thr Arg Leu Glu Ile Lys
            100                 105

<210> SEQ ID NO 5
<211> LENGTH: 5
<212> TYPE: PRT
<213> ORGANISM: Artificial Sequence
<220> FEATURE:
<223> OTHER INFORMATION: Synthetic: 3G5 VH CDR1 (KABAT)

<400> SEQUENCE: 5

Ser Asn Gly Ile His
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic: 3G5 VH CDR1 (CHOTHIA)

<400> SEQUENCE: 6

Gly Phe Thr Phe Ser Ser Asn
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic: 3G5 VH CDR2 (KABAT)

<400> SEQUENCE: 7

Val Ile Trp Ser Asp Gly Ser Asn Lys Phe Tyr Ala Asp Ser Val Lys
1               5                   10                  15

Gly

<210> SEQ ID NO 8
<211> LENGTH: 6
<212> TYPE: PRT
<213> ORGANISM: Artificial Sequence
<220> FEATURE:
<223> OTHER INFORMATION: Synthetic: 3G5 VH CDR2 (CHOTHIA)

<400> SEQUENCE: 8

Trp Ser Asp Gly Ser Asn
1               5

<210> SEQ ID NO 9
<211> LENGTH: 13
<212> TYPE: PRT
<213> ORGANISM: Artificial Sequence
<220> FEATURE:
<223> OTHER INFORMATION: Synthetic: 3G5 VH CDR3 (KABAT)

<400> SEQUENCE: 9

Ala Ser Gly Ser Gly Ser Tyr Tyr Asn Phe Phe Asp Tyr
1               5                   10

<210> SEQ ID NO 10
<211> LENGTH: 13

```
<212> TYPE: PRT
<213> ORGANISM: Artificial Sequence
<220> FEATURE:
<223> OTHER INFORMATION: Synthetic: 3G5  VH CDR3 (CHOTHIA)

<400> SEQUENCE: 10

Ala Ser Gly Ser Gly Ser Tyr Tyr Asn Phe Phe Asp Tyr
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic: 3G5  VL CDR1 (KABAT)

<400> SEQUENCE: 11

Arg Ala Ser Gln Ser Val Arg Ser Asn Leu Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic: 3G5  VL CDR1 (CHOTHIA)

<400> SEQUENCE: 12

Arg Ala Ser Gln Ser Val Arg Ser Asn Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic: 3G5  VL CDR2 (KABAT)

<400> SEQUENCE: 13

Gly Ala Ser Thr Arg Ala Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic: 3G5  VL CDR2 (CHOTHIA)

<400> SEQUENCE: 14

Gly Ala Ser Thr Arg Ala Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic: 3G5  VL CDR3 (KABAT)

<400> SEQUENCE: 15

Gln Gln His Asn Lys Trp Ile Thr
1               5

<210> SEQ ID NO 16
<211> LENGTH: 8
<212> TYPE: PRT
```

<213> ORGANISM: Artificial Sequence
<220> FEATURE:
<223> OTHER INFORMATION: Synthetic: 3G5 VL CDR3 (CHOTHIA)

<400> SEQUENCE: 16

Gln Gln His Asn Lys Trp Ile Thr
1               5

<210> SEQ ID NO 17
<211> LENGTH: 118
<212> TYPE: PRT
<213> ORGANISM: Artificial Sequence
<220> FEATURE:
<223> OTHER INFORMATION: Synthetic: 3C3 VH

<400> SEQUENCE: 17

Gln Val Gln Leu Val Glu Ser Gly Gly Val Val Gln Pro Gly Arg
1               5                   10                  15

Ser Leu Arg Leu Ser Cys Ala Gly Ser Gly Phe Ile Phe Ser Arg Tyr
                20                  25                  30

Gly Met Tyr Trp Val Arg Gln Ala Pro Gly Lys Gly Leu Glu Trp Val
            35                  40                  45

Ala Val Ile Trp Tyr Asp Gly Ser Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Pro Trp Tyr Tyr Phe Asp Tyr Trp Gly Gln Gly Thr
            100                 105                 110

Leu Val Thr Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: Synthetic: 3C3 - VL

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Lys Ser Ala Pro Phe
                85                  90                  95

Thr Phe Gly Pro Gly Thr Lys Val Asp Ile Lys
            100                 105

<210> SEQ ID NO 19
<211> LENGTH: 5
<212> TYPE: PRT
<213> ORGANISM: Artificial Sequence

```
<220> FEATURE:
<223> OTHER INFORMATION: Synthetic: 3C3  VH CDR1 (KABAT)

<400> SEQUENCE: 19

Arg Tyr Gly Met Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic: 3C3  VH CDR1 (CHOTHIA)

<400> SEQUENCE: 20

Gly Phe Ile Phe Ser Arg Tyr
1               5

<210> SEQ ID NO 21
<211> LENGTH: 17
<212> TYPE: PRT
<213> ORGANISM: Artificial Sequence
<220> FEATURE:
<223> OTHER INFORMATION: Synthetic: 3C3  VH CDR2 (KABAT)

<400> SEQUENCE: 21

Val Ile Trp Tyr Asp Gly Ser Tyr Lys Tyr Tyr Ala Asp Ser Val Lys
1               5                   10                  15

Gly

<210> SEQ ID NO 22
<211> LENGTH: 6
<212> TYPE: PRT
<213> ORGANISM: Artificial Sequence
<220> FEATURE:
<223> OTHER INFORMATION: Synthetic: 3C3  VH CDR2 (CHOTHIA)

<400> SEQUENCE: 22

Trp Tyr Asp Gly Ser Tyr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic: 3C3  VH CDR3 (KABAT)

<400> SEQUENCE: 23

Glu Ser Pro Trp Tyr Tyr Phe Asp Tyr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic: 3C3  VH CDR3 (CHOTHIA)

<400> SEQUENCE: 24

Glu Ser Pro Trp Tyr Tyr Phe Asp Tyr
1               5

<210> SEQ ID NO 25
<211> LENGTH: 11
<212> TYPE: PRT
```

```
<213> ORGANISM: Artificial Sequence
<220> FEATURE:
<223> OTHER INFORMATION: Synthetic: 3C3  VL CDR1 (KABAT)

<400> SEQUENCE: 25

Arg Ala Ser Gln Gly Ile Ser Asn Tyr Leu Ala
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic: 3C3  VL CDR1 (CHOTHIA)

<400> SEQUENCE: 26

Arg Ala Ser Gln Gly Ile Ser Asn Tyr Leu Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic: 3C3  VL CDR2 (KABAT)

<400> SEQUENCE: 27

Ala Ala Ser Thr Leu Gln Ser
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic: 3C3  VL CDR2 (CHOTHIA)

<400> SEQUENCE: 28

Ala Ala Ser Thr Leu Gln Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic: 3C3  VL CDR3 (KABAT)

<400> SEQUENCE: 29

Gln Lys Tyr Lys Ser Ala Pro Phe Thr
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic: 3C3  VL CDR3 (CHOTHIA)

<400> SEQUENCE: 30

Gln Lys Tyr Lys Ser Ala Pro Phe Thr
1               5

<210> SEQ ID NO 31
<211> LENGTH: 123
<212> TYPE: PRT
<213> ORGANISM: Artificial Sequence
```

```
<220> FEATURE:
<223> OTHER INFORMATION: Synthetic: 3B6  VH

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Asn Ser Leu Arg Ala Glu Asp Thr Ala Val Tyr Tyr Cys
                85                  90                  95

Ala Lys Arg Ala Gly Gly Ser Phe Tyr Tyr Tyr Tyr Gly Met Asp Val
            100                 105                 110

Trp Gly Gln Gly Thr Thr Val Thr Val Ser Ser
        115                 120

<210> SEQ ID NO 32
<211> LENGTH: 112
<212> TYPE: PRT
<213> ORGANISM: Artificial Sequence
<220> FEATURE:
<223> OTHER INFORMATION: Synthetic: 3B6  VL

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Asn Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Ala
                85                  90                  95

Leu Gln Thr Pro Trp Thr Phe Gly His Gly Thr Lys Val Glu Ile Lys
            100                 105                 110

<210> SEQ ID NO 33
<211> LENGTH: 5
<212> TYPE: PRT
<213> ORGANISM: Artificial Sequence
<220> FEATURE:
<223> OTHER INFORMATION: Synthetic: 3B6  VH CDR1 (KABAT)

<400> SEQUENCE: 33

Ser Tyr Ala Met Ser
1               5

<210> SEQ ID NO 34
<211> LENGTH: 7
<212> TYPE: PRT
<213> ORGANISM: Artificial Sequence
<220> FEATURE:
```

<223> OTHER INFORMATION: Synthetic: 3B6  VH CDR1 (CHOTHIA)

<400> SEQUENCE: 34

Gly Phe Thr Phe Ser Ser Tyr
1               5

<210> SEQ ID NO 35
<211> LENGTH: 17
<212> TYPE: PRT
<213> ORGANISM: Artificial Sequence
<220> FEATURE:
<223> OTHER INFORMATION: Synthetic: 3B6  VH CDR2 (KABAT)

<400> SEQUENCE: 35

Gly Ile Thr Gly Thr Gly Gly Ser Thr Tyr Tyr Ala Asp Ser Val Lys
1               5                   10                  15

Gly

<210> SEQ ID NO 36
<211> LENGTH: 6
<212> TYPE: PRT
<213> ORGANISM: Artificial Sequence
<220> FEATURE:
<223> OTHER INFORMATION: Synthetic: 3B6  VH CDR2 (CHOTHIA)

<400> SEQUENCE: 36

Thr Gly Thr Gly Gly Ser
1               5

<210> SEQ ID NO 37
<211> LENGTH: 14
<212> TYPE: PRT
<213> ORGANISM: Artificial Sequence
<220> FEATURE:
<223> OTHER INFORMATION: Synthetic: 3B6  VH CDR3 (KABAT)

<400> SEQUENCE: 37

Arg Ala Gly Gly Ser Phe Tyr Tyr Tyr Gly Met Asp Val
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic: 3B6  VH CDR3 (CHOTHIA)

<400> SEQUENCE: 38

Arg Ala Gly Gly Ser Phe Tyr Tyr Tyr Gly Met Asp Val
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Synthetic: 3B6  VL CDR1 (KABAT)

<400> SEQUENCE: 39

Arg Ser Ser Gln Ser Leu Leu His Ser Thr Gly Tyr Asn Tyr Leu Asp
1               5                   10                  15

<210> SEQ ID NO 40
<211> LENGTH: 16
<212> TYPE: PRT
<213> ORGANISM: Artificial Sequence

```
<220> FEATURE:
<223> OTHER INFORMATION: Synthetic: 3B6  VL CDR1 (CHOTHIA)

<400> SEQUENCE: 40

Arg Ser Ser Gln Ser Leu Leu His Ser Thr Gly Tyr Asn Tyr Leu Asp
1               5                   10                  15

<210> SEQ ID NO 41
<211> LENGTH: 7
<212> TYPE: PRT
<213> ORGANISM: Artificial Sequence
<220> FEATURE:
<223> OTHER INFORMATION: Synthetic: 3B6  VL CDR2 (KABAT)

<400> SEQUENCE: 41

Leu Gly Ser Asn Arg Ala Ser
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic: 3B6  VL CDR2 (CHOTHIA)

<400> SEQUENCE: 42

Leu Gly Ser Asn Arg Ala Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic: 3B6  VL CDR3 (KABAT)

<400> SEQUENCE: 43

Met Gln Ala Leu Gln Thr Pro Trp Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic: 3B6  VL CDR3 (CHOTHIA)

<400> SEQUENCE: 44

Met Gln Ala Leu Gln Thr Pro Trp Thr
1               5

<210> SEQ ID NO 45
<211> LENGTH: 122
<212> TYPE: PRT
<213> ORGANISM: Artificial Sequence
<220> FEATURE:
<223> OTHER INFORMATION: Synthetic: 6H6 - VH

<400> SEQUENCE: 45

Gln Val Gln Leu Val Glu Ser Gly Gly Gly Val Val Gln Pro Gly Arg
1               5                   10                  15

Ser Leu Arg Phe Ser Cys Ala Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45
```

Ala Val Ile Trp Asp Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Gly Gly Ser Gly Arg Tyr Tyr Asn Tyr Phe Asp Tyr Trp
            100                 105                 110

Gly Gln Gly Thr Leu Val Thr Val Ser Ser
            115                 120

<210> SEQ ID NO 46
<211> LENGTH: 106
<212> TYPE: PRT
<213> ORGANISM: Artificial Sequence
<220> FEATURE:
<223> OTHER INFORMATION: Synthetic: 6H6 - VL

<400> SEQUENCE: 46

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln His Asn Asn Trp Leu Thr
                 85                  90                  95

Phe Gly Gly Gly Thr Lys Val Glu Ile Lys
            100                 105

<210> SEQ ID NO 47
<211> LENGTH: 5
<212> TYPE: PRT
<213> ORGANISM: Artificial Sequence
<220> FEATURE:
<223> OTHER INFORMATION: Synthetic: 6H6 VH CDR1 (KABAT)

<400> SEQUENCE: 47

Ser Tyr Gly Met His
 1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic: 6H6 VH CDR1 (CHOTHIA)

<400> SEQUENCE: 48

Gly Phe Thr Leu Ser Ser Tyr
 1               5

<210> SEQ ID NO 49
<211> LENGTH: 17
<212> TYPE: PRT
<213> ORGANISM: Artificial Sequence
<220> FEATURE:
<223> OTHER INFORMATION: Synthetic: 6H6 VH CDR2 (KABAT)

```
<400> SEQUENCE: 49

Val Ile Trp Asp Asp Gly Ser Asn Lys Tyr Tyr Ala Asp Ser Val Lys
1               5                   10                  15

Gly

<210> SEQ ID NO 50
<211> LENGTH: 6
<212> TYPE: PRT
<213> ORGANISM: Artificial Sequence
<220> FEATURE:
<223> OTHER INFORMATION: Synthetic: 6H6  VH CDR2 (CHOTHIA)

<400> SEQUENCE: 50

Trp Asp Asp Gly Ser Asn
1               5

<210> SEQ ID NO 51
<211> LENGTH: 13
<212> TYPE: PRT
<213> ORGANISM: Artificial Sequence
<220> FEATURE:
<223> OTHER INFORMATION: Synthetic: 6H6  VH CDR3 (KABAT)

<400> SEQUENCE: 51

Ala Gly Gly Ser Gly Arg Tyr Tyr Asn Tyr Phe Asp Tyr
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic: 6H6  VH CDR3 (CHOTHIA)

<400> SEQUENCE: 52

Ala Gly Gly Ser Gly Arg Tyr Tyr Asn Tyr Phe Asp Tyr
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic: 6H6  VL CDR1 (KABAT)

<400> SEQUENCE: 53

Arg Ala Ser Gln Ser Val Arg Ser Asn Leu Ala
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic: 6H6  VL CDR1 (CHOTHIA)

<400> SEQUENCE: 54

Arg Ala Ser Gln Ser Val Arg Ser Asn Leu Ala
1               5                   10

<210> SEQ ID NO 55
<211> LENGTH: 7
<212> TYPE: PRT
<213> ORGANISM: Artificial Sequence
<220> FEATURE:
```

<223> OTHER INFORMATION: Synthetic: 6H6 VL CDR2 (KABAT)

<400> SEQUENCE: 55

Gly Ala Ser Thr Arg Ala Thr
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic: 6H6 VL CDR2 (CHOTHIA)

<400> SEQUENCE: 56

Gly Ala Ser Thr Arg Ala Thr
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic: 6H6 VL CDR3 (KABAT)

<400> SEQUENCE: 57

Gln Gln His Asn Asn Trp Leu Thr
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic: 6H6 VL CDR3 (CHOTHIA)

<400> SEQUENCE: 58

Gln Gln His Asn Asn Trp Leu Thr
1               5

<210> SEQ ID NO 59
<211> LENGTH: 123
<212> TYPE: PRT
<213> ORGANISM: Artificial Sequence
<220> FEATURE:
<223> OTHER INFORMATION: Synthetic: 1B4 - VH

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Val Pro Gly Lys Gly Leu Glu Trp Val
        35                  40                  45

Ser Gly Ile Thr Gly Ser Gly Ala Asn Thr Phe Tyr Thr Asp Ser Val
    50                  55                  60

Lys Gly Arg Phe Thr Ile Ser Arg Asp Asn Ser Asn Ser Leu Tyr
65                  70                  75                  80

Leu Gln Met Asn Ser Leu Arg Ala Asp Asp Thr Ala Val Tyr Tyr Cys
                85                  90                  95

Ala Lys Arg Asn Gly Gly Ser Tyr Tyr Tyr Tyr Gly Met Asp Val
            100                 105                 110

Trp Gly Gln Gly Thr Thr Val Thr Val Ser Ser
        115                 120

```
<210> SEQ ID NO 60
<211> LENGTH: 112
<212> TYPE: PRT
<213> ORGANISM: Artificial Sequence
<220> FEATURE:
<223> OTHER INFORMATION: Synthetic: 1B4 - VL

<400> SEQUENCE: 60

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Ser Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ile Pro Trp Thr Phe Gly Gln Gly Thr Lys Val Glu Ile Lys
            100                 105                 110

<210> SEQ ID NO 61
<211> LENGTH: 5
<212> TYPE: PRT
<213> ORGANISM: Artificial Sequence
<220> FEATURE:
<223> OTHER INFORMATION: Synthetic: 1B4  VH CDR1 (KABAT)

<400> SEQUENCE: 61

Ser Tyr Ala Met Thr
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic: 1B4  VH CDR1 (CHOTHIA)

<400> SEQUENCE: 62

Gly Phe Thr Phe Ser Ser Tyr
1               5

<210> SEQ ID NO 63
<211> LENGTH: 17
<212> TYPE: PRT
<213> ORGANISM: Artificial Sequence
<220> FEATURE:
<223> OTHER INFORMATION: Synthetic: 1B4  VH CDR2 (KABAT)

<400> SEQUENCE: 63

Gly Ile Thr Gly Ser Gly Ala Asn Thr Phe Tyr Thr Asp Ser Val Lys
1               5                   10                  15

Gly

<210> SEQ ID NO 64
<211> LENGTH: 6
<212> TYPE: PRT
<213> ORGANISM: Artificial Sequence
<220> FEATURE:
```

```
<223> OTHER INFORMATION: Synthetic: 1B4  VH CDR2 (CHOTHIA)

<400> SEQUENCE: 64

Thr Gly Ser Gly Ala Asn
1               5

<210> SEQ ID NO 65
<211> LENGTH: 14
<212> TYPE: PRT
<213> ORGANISM: Artificial Sequence
<220> FEATURE:
<223> OTHER INFORMATION: Synthetic: 1B4  VH CDR3 (KABAT)

<400> SEQUENCE: 65

Arg Asn Gly Gly Ser Tyr Tyr Tyr Tyr Gly Met Asp Val
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Synthetic: 1B4  VH CDR3 (CHOTHIA)

<400> SEQUENCE: 66

Arg Asn Gly Gly Ser Tyr Tyr Tyr Tyr Gly Met Asp Val
1               5                   10

<210> SEQ ID NO 67
<211> LENGTH: 16
<212> TYPE: PRT
<213> ORGANISM: Artificial Sequence
<220> FEATURE:
<223> OTHER INFORMATION: Synthetic: 1B4  VL CDR1 (KABAT)

<400> SEQUENCE: 67

Arg Ser Ser Gln Ser Leu Leu His Ser Ser Gly Tyr Asn Tyr Leu Asp
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetic: 1B4  VL CDR1 (CHOTHIA)

<400> SEQUENCE: 68

Arg Ser Ser Gln Ser Leu Leu His Ser Ser Gly Tyr Asn Tyr Leu Asp
1               5                   10                  15

<210> SEQ ID NO 69
<211> LENGTH: 7
<212> TYPE: PRT
<213> ORGANISM: Artificial Sequence
<220> FEATURE:
<223> OTHER INFORMATION: Synthetic: 1B4  VL CDR2 (KABAT)

<400> SEQUENCE: 69

Leu Gly Ser Asn Arg Ala Ser
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic: 1B4  VL CDR2 (CHOTHIA)
```

<400> SEQUENCE: 70

Leu Gly Ser Asn Arg Ala Ser
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic: 1B4 VL CDR3 (KABAT)

<400> SEQUENCE: 71

Met Gln Ala Leu Gln Ile Pro Trp Thr
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic: 1B4 VL CDR3 (CHOTHIA)

<400> SEQUENCE: 72

Met Gln Ala Leu Gln Ile Pro Trp Thr
1               5

<210> SEQ ID NO 73
<211> LENGTH: 123
<212> TYPE: PRT
<213> ORGANISM: Artificial Sequence
<220> FEATURE:
<223> OTHER INFORMATION: Synthetic: 3B6-NS VH

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Asn Ser Leu Arg Ala Glu Asp Thr Ala Val Tyr Tyr Cys
                85                  90                  95

Ala Lys Arg Ala Gly Gly Ser Phe Tyr Tyr Tyr Gly Met Asp Val
            100                 105                 110

Trp Gly Gln Gly Thr Thr Val Thr Val Ser Ser
        115                 120

<210> SEQ ID NO 74
<211> LENGTH: 112
<212> TYPE: PRT
<213> ORGANISM: Artificial Sequence
<220> FEATURE:
<223> OTHER INFORMATION: Synthetic: 3B6-NS VL

<400> SEQUENCE: 74

Asp Ile Val Met Thr Gln Ser Pro Leu Ser Leu Pro Val Thr Pro Gly
1               5                   10                  15

```
Glu Pro Ala Ser Ile Ser Cys Arg Ser Ser Gln Ser Leu His Ser
            20                  25                  30

Thr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Ala
                85                  90                  95

Leu Gln Thr Pro Trp Thr Phe Gly His Gly Thr Lys Val Glu Ile Lys
            100                 105                 110

<210> SEQ ID NO 75
<211> LENGTH: 5
<212> TYPE: PRT
<213> ORGANISM: Artificial Sequence
<220> FEATURE:
<223> OTHER INFORMATION: Synthetic: 3B6-NS  VH CDR1 (KABAT)

<400> SEQUENCE: 75

Ser Tyr Ala Met Ser
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic: 3B6-NS  VH CDR1 (CHOTHIA)

<400> SEQUENCE: 76

Gly Phe Thr Phe Ser Ser Tyr
1               5

<210> SEQ ID NO 77
<211> LENGTH: 17
<212> TYPE: PRT
<213> ORGANISM: Artificial Sequence
<220> FEATURE:
<223> OTHER INFORMATION: Synthetic: 3B6-NS  VH CDR2 (KABAT)

<400> SEQUENCE: 77

Gly Ile Thr Gly Thr Gly Gly Ser Thr Tyr Tyr Ala Asp Ser Val Lys
1               5                   10                  15

Gly

<210> SEQ ID NO 78
<211> LENGTH: 6
<212> TYPE: PRT
<213> ORGANISM: Artificial Sequence
<220> FEATURE:
<223> OTHER INFORMATION: Synthetic: 3B6-NS  VH CDR2 (CHOTHIA)

<400> SEQUENCE: 78

Thr Gly Thr Gly Gly Ser
1               5

<210> SEQ ID NO 79
<211> LENGTH: 14
<212> TYPE: PRT
<213> ORGANISM: Artificial Sequence
<220> FEATURE:
<223> OTHER INFORMATION: Synthetic: 3B6-NS  VH CDR3 (KABAT)
```

<400> SEQUENCE: 79

Arg Ala Gly Gly Ser Phe Tyr Tyr Tyr Gly Met Asp Val
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Synthetic: 3B6-NS  VH CDR3 (CHOTHIA)

<400> SEQUENCE: 80

Arg Ala Gly Gly Ser Phe Tyr Tyr Tyr Gly Met Asp Val
1               5                   10

<210> SEQ ID NO 81
<211> LENGTH: 16
<212> TYPE: PRT
<213> ORGANISM: Artificial Sequence
<220> FEATURE:
<223> OTHER INFORMATION: Synthetic: 3B6-NS  VL CDR1 (KABAT)

<400> SEQUENCE: 81

Arg Ser Ser Gln Ser Leu Leu His Ser Thr Gly Tyr Asn Tyr Leu Asp
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Synthetic: 3B6-NS  VL CDR1 (CHOTHIA)

<400> SEQUENCE: 82

Arg Ser Ser Gln Ser Leu Leu His Ser Thr Gly Tyr Asn Tyr Leu Asp
1               5                   10                  15

<210> SEQ ID NO 83
<211> LENGTH: 7
<212> TYPE: PRT
<213> ORGANISM: Artificial Sequence
<220> FEATURE:
<223> OTHER INFORMATION: Synthetic: 3B6-NS  VL CDR2 (KABAT)

<400> SEQUENCE: 83

Leu Gly Ser Asn Arg Ala Ser
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic: 3B6-NS  VL CDR2 (CHOTHIA)

<400> SEQUENCE: 84

Leu Gly Ser Asn Arg Ala Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic: 3B6-NS  VL CDR3 (KABAT)

```
<400> SEQUENCE: 85

Met Gln Ala Leu Gln Thr Pro Trp Thr
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic: 3B6-NS  VL CDR3 (CHOTHIA)

<400> SEQUENCE: 86

Met Gln Ala Leu Gln Thr Pro Trp Thr
1               5

<210> SEQ ID NO 87
<211> LENGTH: 122
<212> TYPE: PRT
<213> ORGANISM: Artificial Sequence
<220> FEATURE:
<223> OTHER INFORMATION: Synthetic: 2E1.2 - VH

<400> SEQUENCE: 87

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Ser Ser Gly Arg Tyr Tyr Asn Tyr Phe Asp Tyr Trp
            100                 105                 110

Gly Gln Gly Thr Leu Val Thr Val Ser Ser
        115                 120

<210> SEQ ID NO 88
<211> LENGTH: 106
<212> TYPE: PRT
<213> ORGANISM: Artificial Sequence
<220> FEATURE:
<223> OTHER INFORMATION: Synthetic: 2E1.2  VL2

<400> SEQUENCE: 88

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr His Cys Gln Gln Tyr Asn Lys Trp Leu Ile
                85                  90                  95
```

Phe Gly Gly Gly Thr Lys Val Glu Ile Lys
            100                 105

<210> SEQ ID NO 89
<211> LENGTH: 5
<212> TYPE: PRT
<213> ORGANISM: Artificial Sequence
<220> FEATURE:
<223> OTHER INFORMATION: Synthetic: 2E1.2 - VH CDR1 (KABAT)

<400> SEQUENCE: 89

Ser Tyr Gly Met His
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic: 2E1.2 - VH CDR1 (CHOTHIA)

<400> SEQUENCE: 90

Gly Phe Thr Phe Ser Ser Tyr
1               5

<210> SEQ ID NO 91
<211> LENGTH: 17
<212> TYPE: PRT
<213> ORGANISM: Artificial Sequence
<220> FEATURE:
<223> OTHER INFORMATION: Synthetic: 2E1.2 - VH CDR2 (KABAT)

<400> SEQUENCE: 91

Val Ile Trp Asp Asp Gly Ser Asn Lys Tyr Tyr Ala Asp Ser Val Lys
1               5                   10                  15

Gly

<210> SEQ ID NO 92
<211> LENGTH: 6
<212> TYPE: PRT
<213> ORGANISM: Artificial Sequence
<220> FEATURE:
<223> OTHER INFORMATION: Synthetic: 2E1.2 - VH CDR2 (CHOTHIA)

<400> SEQUENCE: 92

Trp Asp Asp Gly Ser Asn
1               5

<210> SEQ ID NO 93
<211> LENGTH: 13
<212> TYPE: PRT
<213> ORGANISM: Artificial Sequence
<220> FEATURE:
<223> OTHER INFORMATION: Synthetic: 2E1.2 - VH CDR3 (KABAT)

<400> SEQUENCE: 93

Ala Gly Ser Ser Gly Arg Tyr Tyr Asn Tyr Phe Asp Tyr
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Synthetic: 2E1.2 - VH CDR3 (CHOTHIA)

```
<400> SEQUENCE: 94

Ala Gly Ser Ser Gly Arg Tyr Tyr Asn Tyr Phe Asp Tyr
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Synthetic: 2E1.2  VL2 CDR1 (KABAT)

<400> SEQUENCE: 95

Arg Ala Ser Gln Ser Val Arg Ser Asn Leu Ala
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Synthetic: 2E1.2  VL2 CDR1 (CHOTHIA)

<400> SEQUENCE: 96

Arg Ala Ser Gln Ser Val Arg Ser Asn Leu Ala
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Synthetic: 2E1.2  VL2 CDR2 (KABAT)

<400> SEQUENCE: 97

Gly Ala Ser Thr Arg Ala Thr
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic: 2E1.2  VL2 CDR2 (CHOTHIA)

<400> SEQUENCE: 98

Gly Ala Ser Thr Arg Ala Thr
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic: 2E1.2 VL2 CDR3 (KABAT)

<400> SEQUENCE: 99

Gln Gln Tyr Asn Lys Trp Leu Ile
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic: 2E1.2  VL2 CDR3 (CHOTHIA)

<400> SEQUENCE: 100
```

```
Gln Gln Tyr Asn Lys Trp Leu Ile
1               5
```

<210> SEQ ID NO 101
<211> LENGTH: 121
<212> TYPE: PRT
<213> ORGANISM: Artificial Sequence
<220> FEATURE:
<223> OTHER INFORMATION: Synthetic: 1B5-NK - VH

<400> SEQUENCE: 101

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Thr Leu Ile Trp Phe Asp Gly Ser Ser Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Phe Ala Ala Val Ala Gly Trp Tyr Phe Asp Phe Trp Gly
            100                 105                 110

Arg Gly Thr Leu Val Thr Val Ser Ser
        115                 120
```

<210> SEQ ID NO 102
<211> LENGTH: 107
<212> TYPE: PRT
<213> ORGANISM: Artificial Sequence
<220> FEATURE:
<223> OTHER INFORMATION: Synthetic: 1B5-NK  VL

<400> SEQUENCE: 102

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Arg Lys Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Phe Ser Ala Pro Tyr
                85                  90                  95

Thr Phe Gly Gln Gly Thr Lys Leu Glu Ile Lys
            100                 105
```

<210> SEQ ID NO 103
<211> LENGTH: 5
<212> TYPE: PRT
<213> ORGANISM: Artificial Sequence
<220> FEATURE:
<223> OTHER INFORMATION: Synthetic: 1B5-NK - VH CDR1 (KABAT)

<400> SEQUENCE: 103

Ser Phe Gly Met His
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic: 1B5-NK - VH CDR1 (CHOTHIA)

<400> SEQUENCE: 104

Gly Phe Thr Phe Ser Ser Phe
1               5

<210> SEQ ID NO 105
<211> LENGTH: 17
<212> TYPE: PRT
<213> ORGANISM: Artificial Sequence
<220> FEATURE:
<223> OTHER INFORMATION: Synthetic: 1B5-NK - VH CDR2 (KABAT)

<400> SEQUENCE: 105

Leu Ile Trp Phe Asp Gly Ser Ser Lys Tyr Tyr Ala Asp Ser Val Lys
1               5                   10                  15

Gly

<210> SEQ ID NO 106
<211> LENGTH: 6
<212> TYPE: PRT
<213> ORGANISM: Artificial Sequence
<220> FEATURE:
<223> OTHER INFORMATION: Synthetic: 1B5-NK - VH CDR2 (CHOTHIA)

<400> SEQUENCE: 106

Trp Phe Asp Gly Ser Ser
1               5

<210> SEQ ID NO 107
<211> LENGTH: 12
<212> TYPE: PRT
<213> ORGANISM: Artificial Sequence
<220> FEATURE:
<223> OTHER INFORMATION: Synthetic: 1B5-NK - VH CDR3 (KABAT)

<400> SEQUENCE: 107

Gly Phe Ala Ala Val Ala Gly Trp Tyr Phe Asp Phe
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Synthetic: 1B5-NK - VH CDR3 (CHOTHIA)

<400> SEQUENCE: 108

Gly Phe Ala Ala Val Ala Gly Trp Tyr Phe Asp Phe
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic: 1B5-NK  VL CDR1 (KABAT)

<400> SEQUENCE: 109

Arg Ala Ser Gln Gly Val Arg Lys Tyr Leu Ala
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic: 1B5-NK VL CDR1 (CHOTHIA)

<400> SEQUENCE: 110

Arg Ala Ser Gln Gly Val Arg Lys Tyr Leu Ala
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Synthetic: 1B5-NK  VL CDR2 (KABAT)

<400> SEQUENCE: 111

Ala Ala Ser Thr Leu Gln Ser
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic: 1B5-NK  VL CDR2 (CHOTHIA)

<400> SEQUENCE: 112

Ala Ala Ser Thr Leu Gln Ser
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic: 1B5-NK VL CDR3 (KABAT)

<400> SEQUENCE: 113

Gln Lys Tyr Phe Ser Ala Pro Tyr Thr
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic: 1B5-NK  VL CDR3 (CHOTHIA)

<400> SEQUENCE: 114

Gln Lys Tyr Phe Ser Ala Pro Tyr Thr
1               5

<210> SEQ ID NO 115
<211> LENGTH: 423
<212> TYPE: DNA
<213> ORGANISM: Artificial Sequence
<220> FEATURE:
<223> OTHER INFORMATION: Synthetic: 3G5 VH

<400> SEQUENCE: 115

```
atggagtttg gctgaccctg gttttcctc gttgctcttt taagaggtgt ccagtgtcag    60
gtgcagttgg tggaatctgg gggaggcgtg gtccagcctg gaagtccct gagactctcc   120 tgtgcagcgt ctggattcac cttcagtagc aatggcattc actgggtccg ccaggctcca   180
ggcaaggggc tggagtgggt ggcagttatc tggtctgatg aagtaataa attctatgca   240 gactccgtga agggccgatt caccatctcc agagacaatt ccaagaacac gctatatctg   300
caaatgaaca gcctgagagc cgaggacacg gctgtatatt actgtgcgag agcctctggt   360
tcggggagtt attataactt ctttgactac tggggccagg gaaccctggt caccgtctcc   420
tca                                                                423

<210> SEQ ID NO 116
<211> LENGTH: 156
<212> TYPE: DNA
<213> ORGANISM: Artificial Sequence
<220> FEATURE:
<223> OTHER INFORMATION: Synthetic: 3G5 VL underline

<400> SEQUENCE: 116
atggaagccc cagcgcagct tctcttcctc ctgctactct ggctcccaga tagcactgga    60
gaaatagtga tgacgcagtc tccagccacc ctgtctgtgt ctccagggga aagagccacc   120
ctctcctgca gggccagtca gagtgttaga agtaac                            156

<210> SEQ ID NO 117
<211> LENGTH: 378
<212> TYPE: DNA
<213> ORGANISM: Artificial Sequence
<220> FEATURE:
<223> OTHER INFORMATION: Synthetic: 3C3 VH

<400> SEQUENCE: 117
atggaagccc cagcgcagct tctcttcctc ctgctactct ggctcccaga tagcactgga    60
gaaatagtga tgacgcagtc tccagccacc ctgtctgtgt ctccagggga aagagccacc   120
ctctcctgca gggccagtca gagtgttaga agtaacttag cctggtacca gcagaaacct   180
ggccaggctc ccaggctcct catctatggt gcatccacca gggccactgg tatcccagcc   240
aggttcagtg gcagtgggtc tgggacagag ttcactctca ccatcaacag cctgcagtct   300
gaagattttg cagtttatta ctgtcagcag cataataagt ggatcacctt cggccaaggg   360
acacgactgg agattaaa                                                378

<210> SEQ ID NO 118
<211> LENGTH: 387
<212> TYPE: DNA
<213> ORGANISM: Artificial Sequence
<220> FEATURE:
<223> OTHER INFORMATION: Synthetic: 3C3 VL

<400> SEQUENCE: 118
atggacatga gggtccctgc tcagctcctg ggactcctgc tgctctggct cccagatacc    60
agatgtgaca tccagatgac ccagtctcca tcctccctgt ctgcatctgt aggagacaga   120
gtcaccatca cttgccgggc gagtcagggc attagcaatt atttagcctg gtatcagcag   180
aaaccaggga aagttcctaa gctcctgatc tatgctgcat ccactttgca atcagggtc    240 ccatctcggt tcagtggcag tggatctggg acagatttca ctctcaccat cagcagcctg   300
cagcctgaag atgttgcaac ttattactgt caaaagtata agagtgcccc attcactttc   360
ggccctggga ccaaagtgga tatcaaa                                      387
```

<210> SEQ ID NO 119
<211> LENGTH: 426
<212> TYPE: DNA
<213> ORGANISM: Artificial Sequence
<220> FEATURE:
<223> OTHER INFORMATION: Synthetic: 3B6 VH

<400> SEQUENCE: 119

```
atggagtttg ggctgagctg gcttttcctt gtggctattt taaaaggtgt ccagtgtgag      60
gtgcagctgt tggagtctgg gggaggcttg gtacagcctg ggggtccct gagactctcc     120 tgtgcagcct ctggattcac ctttagcagc tatgccatga gctgggtccg ccaggctcca    180
gggaaggggc tggagtgggt ctcaggtata actggtactg gtggtagcac atactacgca    240
gactccgtga agggccggtt caccatctcc agagacaatt ccaagaacac gctgtatgtg    300
caaatgaaca gcctgagagc cgaggacacg gccgtatatt actgtgcgaa aagggctggt    360
gggagcttct actactacta cggtatggac gtctggggcc aagggaccac ggtcaccgtc    420
tcctca                                                              426
```

<210> SEQ ID NO 120
<211> LENGTH: 396
<212> TYPE: DNA
<213> ORGANISM: Artificial Sequence
<220> FEATURE:
<223> OTHER INFORMATION: Synthetic: 3B6 VL

<400> SEQUENCE: 120

```
atgaggctcc ctgctcagct cctggggctg ctaatgctct gggtctctgg atccagtggg      60
gatattgtga tgactcagtc tccactctcc ctgcccgtca cccctggaga gccggcctcc    120
atctcctgca ggtctagtca gagcctcctg catagtactg gatacaacta tttggattgg    180
tacctgcaga agccagggca gtctccacag ctcctgatct atttgggttc taatcgggcc    240
tccggggtcc ctgacaggtt caatggcagt ggatcaggca cagattttac actgaaaatc    300
agcagagtgg aggctgagga ttttggggtt tattactgca tgcaagctct acaaactccg    360
tggacgttcg gccacgggac caaggtggaa atcaaa                              396
```

<210> SEQ ID NO 121
<211> LENGTH: 423
<212> TYPE: DNA
<213> ORGANISM: Artificial Sequence
<220> FEATURE:
<223> OTHER INFORMATION: Synthetic: 6H6 VH

<400> SEQUENCE: 121

```
atggagtttg ggctgagctg ggtattcctc gttgctcttt taagaggtgt ccagtgtcag      60
gtgcagctgg tggagtctgg gggaggcgtg gtccagcctg ggaggtccct gagattctcc    120
tgtgcagcgt ctggattcac cctcagtagc tatggcatgc actgggtccg ccaggctcca    180
ggcaaggggc tggagtgggt ggcagttata tgggatgatg aagtaataa atactatgca    240 gactccgtga agggccgatt caccatctcc agagacaatt ccaagaacac gctgtatctg    300
caaatgaaca gcctgagagc cgaggacacg gctgtctatt actgtgcgag agcggggggt    360
tcggggaggt attataacta ctttgactac tggggccagg gaaccctggt caccgtctcc    420
tca                                                                  423
```

<210> SEQ ID NO 122

```
<211> LENGTH: 378
<212> TYPE: DNA
<213> ORGANISM: Artificial Sequence
<220> FEATURE:
<223> OTHER INFORMATION: Synthetic: 6H6 VL

<400> SEQUENCE: 122
atggaagccc cagcgcagct tctcttcctc ctgctactct ggctcccaga taccactgga      60
gaaatagtga tgacgcagtc tccagccacc ctgtctgtgt ctccagggga aagagccacc     120
ctctcctgca gggccagtca gagtgttaga agcaacttag cctggtacca gcagaaacct     180
ggccaggctc ccaggctcct catctatggt gcatccacca gggccactgg tatcccagcc     240
aggttcagtg gcagtgggtc tgggacagac ttcactctca ccatcagcag cctgcagtct     300
gaagattttg cagtttatta ctgtcagcag cataataact ggctcacttt cggcggaggg     360
accaaggtgg agatcaaa                                                    378

<210> SEQ ID NO 123
<211> LENGTH: 426
<212> TYPE: DNA
<213> ORGANISM: Artificial Sequence
<220> FEATURE:
<223> OTHER INFORMATION: Synthetic: 1B4 VH

<400> SEQUENCE: 123
atggagtttg ggctgagctg gcttttctt gtggctattt taaaaggtgt ccaatgtgag       60
gtgcagctgt tggaatctgg gggaggcttg gtacagcctg gggggtccct gagactctcc     120
tgtgcggcct ctgggttcac ctttagcagc tatgccatga cctgggtccg ccaggttcca     180
gggaagggcc tggagtgggt ctcaggtatt actggtagtg gtgctaacac attctacaca     240
gactccgtga agggccggtt caccatttcc agagacaatt ccataattc gctgtatctg     300 caaatgaaca gcctgagagc cgatgacacg gccgtatact actgtgcgaa agaaatggt     360 gggagttact actactacta cggcatggac gtctggggcc aagggaccac ggtcaccgtg     420
tcctca                                                                 426

<210> SEQ ID NO 124
<211> LENGTH: 396
<212> TYPE: DNA
<213> ORGANISM: Artificial Sequence
<220> FEATURE:
<223> OTHER INFORMATION: Synthetic: 1B4 VL

<400> SEQUENCE: 124
atgaggctcc ctgctcagct cctggggctg ctaatgctct gggtctctgg atccagtggg      60
gatattgtga tgactcagtc tccactctcc ctgcccgtca ccctggaga gccggcctcc     120 atctcctgca ggtcaagtca gagcctcctg catagtagtg gatacaacta tttggattgg     180
tacctgcaga agccagggca gtctccacaa ctcctgatct atttgggttc taatcgggcc     240
tccggggtcc ctgacaggtt cagtggcagt ggatcaggca cagattttac actgaaaatc     300
agcagagtgg aggctgagga tgttggggtt tattactgca tgcaagctct acaaattccg     360
tggacgttcg gccaagggac caaggtggaa atcaaa                                396

<210> SEQ ID NO 125
<211> LENGTH: 423
<212> TYPE: DNA
<213> ORGANISM: Artificial Sequence
<220> FEATURE:
<223> OTHER INFORMATION: Synthetic: 2E1.2 VH
```

<400> SEQUENCE: 125

```
atggagtttg ggctgagctg ggttttcctc gttgctcttt taagaggtgt ccagtgtcag     60
gtgcagctgg tggagtctgg gggaggcgtg gtccagcctg gaggtccct gagactctcc    120
tgtgcagcgt ctggattcac cttcagtagc tatggcatgc actgggtccg ccaggctcca   180
ggcaaggggc tggagtgggt ggcagttata tgggatgatg aagtaataa atactatgca    240
gactccgtga agggccgatt caccatctcc agagacaatt ccaagaacac gctgtatctg   300
caaatgaaca gcctgagagc cgaggacacg gctgtgtatt actgtgcgag agcgggaagt   360
tcggggaggt attataacta ctttgactac tggggccagg gaaccctggt caccgtctcc   420
tca                                                                 423
```

<210> SEQ ID NO 126
<211> LENGTH: 378
<212> TYPE: DNA
<213> ORGANISM: Artificial Sequence
<220> FEATURE:
<223> OTHER INFORMATION: Synthetic: 2E1.2 VL2

<400> SEQUENCE: 126

```
atggaagccc cagcgcagct tctcttcctc ctgctactct ggctcccaga taccactgga    60
gaaatagtga tgacgcagtc tccagccacc ctgtctgtgt ctccagggga aagagccacc   120
ctctcctgca gggccagtca gagtgttagg agcaacttag cctggtatca gcagaaacct   180
ggccaggctc ccaggctcct catctatggt gcatccacca gggccactgg tatcccagac   240
aggttcagtg gcagtgggtc tgggacagag ttcactctca ccatcagcag cctgcagtct   300
gaagattttg cagtttatca ctgtcagcag tataataagt ggctcatttt cggcggaggg   360
accaaggtgg agatcaaa                                                 378
```

<210> SEQ ID NO 127
<211> LENGTH: 420
<212> TYPE: DNA
<213> ORGANISM: Artificial Sequence
<220> FEATURE:
<223> OTHER INFORMATION: Synthetic: 1B5 VH

<400> SEQUENCE: 127

```
atggagtttg ggctgagctg ggttttcctc gttgctcttt taagaggtgt ccagtgtcag     60
gtgcagctgg tggagtctgg gggaggcgtg gtccagcctg gaggtccct gagactctcc    120
tgtgcagcgt ctggattcac cttcagtagc tttggcatgc actgggtccg ccaggctcca   180
ggcaaggggc tggagtgggt gacacttata tggtttgatg aagttctaa atactatgca    240
gactccgtga agggccgatt caccatctcc agagacaact ccaacaacac gctgtatctg   300
caaatgaaca gcctgagagc cgaggacacg gctgtatatt actgtgtgag aggttttgca   360
gcagtggctg gtggtactt cgatttctgg ggccgtggca ccctggtcac tgtctcctca    420
```

<210> SEQ ID NO 128
<211> LENGTH: 387
<212> TYPE: DNA
<213> ORGANISM: Artificial Sequence
<220> FEATURE:
<223> OTHER INFORMATION: Synthetic: 1B5 VL

<400> SEQUENCE: 128

```
atggacatga gggtccctgc tcagctcctg ggactcctgc tgctctggct cccagatacc     60
```

```
agatgtgaca tccagatgac ccagtctcca tcctccctgt ctgcatctgt aggagacaga    120
gtcaccatca cttgccgggc gagtcagggc gttagaaagt atttagcctg gtatcagcag    180
aaaccaggga aagttcctaa gctcctgatc tatgctgcat ccactttgca atcaggggtc    240
ccatctcggt tcagtggcag tggatctggg acagatttca ctctcaccat cagcagcctg    300
cagcctgaag atgttgcaac ttattactgt caaaagtatt tcagtgcccc gtacactttt    360
ggccagggga ccaaactgga gatcaaa                                        387

<210> SEQ ID NO 129
<211> LENGTH: 426
<212> TYPE: DNA
<213> ORGANISM: Artificial Sequence
<220> FEATURE:
<223> OTHER INFORMATION: Synthetic: 3B6-NS VH

<400> SEQUENCE: 129
atggagtttg ggctgagctg gcttttctt gtggctattt taaaaggtgt ccagtgtgag     60
gtgcagctgt tggagtctgg gggaggcttg gtacagcctg gggggtccct gagactctcc    120
tgtgcagcct ctggattcac ctttagcagc tatgccatga gctgggtccg ccaggctcca    180
gggaaggggc tggagtgggt ctcaggtata actggtactg gtggtagcac atactacgca    240
gactccgtga agggccggtt caccatctcc agagacaatt ccaagaacac gctgtatgtg    300
caaatgaaca gcctgagagc cgaggacacg gccgtatatt actgtgcgaa aagggctggt    360
gggagcttct actactacta cggtatggac gtctggggcc aagggaccac ggtcaccgtc    420
tcctca                                                               426

<210> SEQ ID NO 130
<211> LENGTH: 396
<212> TYPE: DNA
<213> ORGANISM: Artificial Sequence
<220> FEATURE:
<223> OTHER INFORMATION: Synthetic: 3B6-NS VL

<400> SEQUENCE: 130
atgaggctcc ctgctcagct cctggggctg ctaatgctct gggtctctgg atccagtggg     60
gatattgtga tgactcagtc tccactctcc ctgcccgtca cccctggaga gccggcctcc    120
atctcctgca ggtctagtca gagcctcctg catagtactg gatacaacta tttggattgg    180
tacctgcaga agccagggca gtctccacag ctcctgatct atttgggttc taatcgggcc    240
tccggggtcc ctgacaggtt cagtggcagt ggatcaggca cagatttac actgaaaatc    300 agcagagtgg aggctgagga ttttggggtt tattactgca tgcaagctct acaaactccg    360
tggacgttcg gccacgggac caaggtggaa atcaaa                              396

<210> SEQ ID NO 131
<211> LENGTH: 420
<212> TYPE: DNA
<213> ORGANISM: Artificial Sequence
<220> FEATURE:
<223> OTHER INFORMATION: Synthetic: 1B5-NK VH

<400> SEQUENCE: 131
atggagtttg ggctgagctg ggttttcctc gttgctcttt taagaggtgt ccagtgtcag     60
gtgcagctgg tggagtctgg gggaggcgtg gtccagcctg gaggtccct gagactctcc     120 tgtgcagcgt ctggattcac cttcagtagc tttggcatgc actgggtccg ccaggctcca    180
ggcaaggggc tggagtgggt gacacttata tggtttgatg gaagttctaa atactatgca    240
```

```
gactccgtga agggccgatt caccatctcc agagacaact ccaagaacac gctgtatctg    300
caaatgaaca gcctgagagc cgaggacacg gctgtatatt actgtgtgag aggttttgca    360
gcagtggctg gtggtactt cgatttctgg ggccgtggca ccctggtcac tgtctcctca     420
```

<210> SEQ ID NO 132
<211> LENGTH: 387
<212> TYPE: DNA
<213> ORGANISM: Artificial Sequence
<220> FEATURE:
<223> OTHER INFORMATION: Synthetic: 1B5-NK VL

<400> SEQUENCE: 132

```
atggacatga gggtccctgc tcagctcctg ggactcctgc tgctctggct cccagatacc    60
agatgtgaca tccagatgac ccagtctcca tcctccctgt ctgcatctgt aggagacaga    120
gtcaccatca cttgccgggc gagtcagggc gttagaaagt atttagcctg gtatcagcag    180
aaaccaggga aagttcctaa gctcctgatc tatgctgcat ccactttgca atcaggggtc    240
ccatctcggt tcagtggcag tggatctggg acagatttca ctctcaccat cagcagcctg    300
cagcctgaag atgttgcaac ttattactgt caaaagtatt tcagtgcccc gtacactttt    360
ggccagggga ccaaactgga gatcaaa                                        387
```

<210> SEQ ID NO 133
<211> LENGTH: 173
<212> TYPE: PRT
<213> ORGANISM: Homo sapiens
<220> FEATURE:
<221> NAME/KEY: misc_feature
<223> OTHER INFORMATION: Human CD40 Extracellular Domain

<400> SEQUENCE: 133

```
Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys His Pro Trp
    130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg
                165                 170
```

<210> SEQ ID NO 134
<211> LENGTH: 326
<212> TYPE: PRT

<213> ORGANISM: Homo sapiens
<220> FEATURE:
<221> NAME/KEY: misc_feature
<223> OTHER INFORMATION: Immunoglobulin heavy constant gamma 2 (IgHG2)

<400> SEQUENCE: 134

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 135
<211> LENGTH: 443
<212> TYPE: PRT
<213> ORGANISM: Artificial Sequence
<220> FEATURE:
<223> OTHER INFORMATION: Synthetic: 3C3 heavy chain

<400> SEQUENCE: 135

```
Gln Val Gln Leu Val Glu Ser Gly Gly Val Val Gln Pro Gly Arg
1               5                   10                  15

Ser Leu Arg Leu Ser Cys Ala Gly Ser Gly Phe Ile Phe Ser Arg Tyr
            20                  25                  30

Gly Met Tyr Trp Val Arg Gln Ala Pro Gly Lys Gly Leu Glu Trp Val
        35                  40                  45

Ala Val Ile Trp Tyr Asp Gly Ser Tyr Lys Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Pro Trp Tyr Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415
```

Gly Asn Val Phe Ser Cys Ser Val Met His Glu Ala Leu His Asn His
            420                 425                 430

Tyr Thr Gln Lys Ser Leu Ser Leu Ser Pro Gly
            435                 440

<210> SEQ ID NO 136
<211> LENGTH: 214
<212> TYPE: PRT
<213> ORGANISM: Artificial Sequence
<220> FEATURE:
<223> OTHER INFORMATION: Synthetic: 3C3 light chain

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Lys Ser Ala Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 137
<211> LENGTH: 462
<212> TYPE: PRT
<213> ORGANISM: Artificial Sequence
<220> FEATURE:
<223> OTHER INFORMATION: Synthetic: 3C3 heavy chain

<400> SEQUENCE: 137

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Gly Ser Gly Phe Ile Phe
        35                  40                  45

Ser Arg Tyr Gly Met Tyr Trp Val Arg Gln Ala Pro Gly Lys Gly Leu
    50                  55                  60

Glu Trp Val Ala Val Ile Trp Tyr Asp Gly Ser Tyr Lys Tyr Tyr Ala
65                  70                  75                  80

Asp Ser Val Lys Gly Arg Phe Thr Ile Ser Arg Asp Asn Ser Lys Asn
            85                  90                  95

Thr Leu Tyr Leu Gln Met Asn Ser Leu Arg Ala Glu Asp Thr Ala Val
            100                 105                 110

Tyr Tyr Cys Ala Arg Glu Ser Pro Trp Tyr Tyr Phe Asp Tyr Trp Gly
            115                 120                 125

Gln Gly Thr Leu Val Thr Val Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Asn Phe Gly Thr Gln Thr Tyr Thr Cys Asn Val Asp His
210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
            245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
            275                 280                 285

Val Gln Phe Asn Trp Tyr Val Asp Gly Val Glu Val His Asn Ala Lys
            290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
            325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
            355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
            405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly
450                 455                 460

<210> SEQ ID NO 138
<211> LENGTH: 233

```
<212> TYPE: PRT
<213> ORGANISM: Artificial Sequence
<220> FEATURE:
<223> OTHER INFORMATION: Synthetic: 3C3 light chain

<400> SEQUENCE: 138
```

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Gly Ile
        35                  40                  45

Ser Asn Tyr Leu Ala Trp Tyr Gln Gln Lys Pro Gly Lys Val Pro Lys
    50                  55                  60

Leu Leu Ile Tyr Ala Ala Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Val Ala Thr Tyr Tyr Cys Gln Lys Tyr Lys Ser
            100                 105                 110

Ala Pro Phe Thr Phe Gly Pro Gly Thr Lys Val Asp Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

```
<210> SEQ ID NO 139
<211> LENGTH: 173
<212> TYPE: PRT
<213> ORGANISM: Unknown
<220> FEATURE:
<223> OTHER INFORMATION: Monkey
<220> FEATURE:
<221> NAME/KEY: misc_feature
<223> OTHER INFORMATION: Monkey CD40 ECD amino acid sequence

<400> SEQUENCE: 139
```

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr Arg Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

```
Thr Ile Cys Thr Cys Glu Glu Gly Leu His Cys Thr Ser Glu Ser Cys
                85                  90                  95

Glu Ser Cys Val Pro His Arg Ser Cys Leu Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys Arg Pro Trp
    130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Gln Arg
                165                 170

<210> SEQ ID NO 140
<211> LENGTH: 94
<212> TYPE: PRT
<213> ORGANISM: Mus musculus

<400> SEQUENCE: 140

Gly Gln Cys Val Thr Cys Ser Asp Lys Gln Tyr Leu His Asp Gly Gln
1               5                   10                  15

Cys Cys Asp Leu Cys Gln Pro Gly Ser Arg Leu Thr Ser His Cys Thr
            20                  25                  30

Ala Leu Glu Lys Thr Gln Cys His Pro Cys Asp Ser Gly Glu Phe Ser
        35                  40                  45

Ala Gln Trp Asn Arg Glu Ile Arg Cys His Gln His Arg His Cys Glu
    50                  55                  60

Pro Asn Gln Gly Leu Arg Val Lys Lys Glu Gly Thr Ala Glu Ser Asp
65                  70                  75                  80

Thr Val Cys Thr Cys Lys Glu Gly Gln His Cys Thr Ser Lys
                85                  90

<210> SEQ ID NO 141
<211> LENGTH: 5
<212> TYPE: PRT
<213> ORGANISM: Artificial Sequence
<220> FEATURE:
<223> OTHER INFORMATION: Synthetic: consensus sequence

<400> SEQUENCE: 141

Asp Lys Gln Tyr Leu
1               5

<210> SEQ ID NO 142
<211> LENGTH: 5
<212> TYPE: PRT
<213> ORGANISM: Artificial Sequence
<220> FEATURE:
<223> OTHER INFORMATION: Synthetic: consensus sequence

<400> SEQUENCE: 142

Leu Cys Gln Pro Gly
1               5

<210> SEQ ID NO 143
<211> LENGTH: 4
<212> TYPE: PRT
<213> ORGANISM: Artificial Sequence
<220> FEATURE:
<223> OTHER INFORMATION: Synthetic: consensus sequence
```

```
<400> SEQUENCE: 143

Trp Asn Arg Glu
1

<210> SEQ ID NO 144
<211> LENGTH: 10
<212> TYPE: PRT
<213> ORGANISM: Artificial Sequence
<220> FEATURE:
<223> OTHER INFORMATION: Synthetic: consensus sequence

<400> SEQUENCE: 144

Cys His Gln His Lys His Cys Asp Pro Asn
1               5                   10

<210> SEQ ID NO 145
<211> LENGTH: 4
<212> TYPE: PRT
<213> ORGANISM: Artificial Sequence
<220> FEATURE:
<223> OTHER INFORMATION: Synthetic: consensus sequence

<400> SEQUENCE: 145

Gly Leu Arg Val
1

<210> SEQ ID NO 146
<211> LENGTH: 11
<212> TYPE: PRT
<213> ORGANISM: Artificial Sequence
<220> FEATURE:
<223> OTHER INFORMATION: Synthetic: consensus sequence

<400> SEQUENCE: 146

Gly Thr Ala Glu Ser Asp Thr Ile Cys Thr Cys
1               5                   10

<210> SEQ ID NO 147
<211> LENGTH: 4
<212> TYPE: PRT
<213> ORGANISM: Artificial Sequence
<220> FEATURE:
<223> OTHER INFORMATION: Synthetic: consensus sequence

<400> SEQUENCE: 147

His Cys Thr Ser
1
```